(12) United States Patent
Wagner et al.

(10) Patent No.: US 7,498,148 B2
(45) Date of Patent: Mar. 3, 2009

(54) METHOD FOR UNIVERSAL ENZYMATIC PRODUCTION OF BIOACTIVE PEPTIDES

(75) Inventors: Fred W. Wagner, Walton, NE (US); Peng Luan, Fishers, IN (US); Yuannan Xia, Lincoln, NE (US); Daniel Strydom, Lincoln, NE (US); Edwin H. Merrifield, Lynnwood, WA (US); Mary J. Bossard, Madison, AL (US); Barton Holmquist, Eagle, NE (US); Jin Seog Seo, Brampton (CA)

(73) Assignee: Restoragen, Inc., Lincoln, NE (US)

( * ) Notice: Subject to any disclaimer, the term of this patent is extended or adjusted under 35 U.S.C. 154(b) by 0 days.

(21) Appl. No.: 11/944,165

(22) Filed: Nov. 21, 2007

(65) Prior Publication Data

US 2008/0153129 A1    Jun. 26, 2008

Related U.S. Application Data

(60) Division of application No. 10/997,074, filed on Nov. 24, 2004, now Pat. No. 7,335,486, which is a continuation of application No. PCT/US03/16470, filed on May 23, 2003.

(60) Provisional application No. 60/383,380, filed on May 24, 2002.

(51) Int. Cl.
  *C12P 21/06* (2006.01)
(52) U.S. Cl. .................................... 435/68.1; 435/220
(58) Field of Classification Search ................ 435/68.1, 435/220
  See application file for complete search history.

(56) References Cited

U.S. PATENT DOCUMENTS

| | | | |
|---|---|---|---|
| 4,336,336 A | 6/1982 | Silhavy et al. | |
| 4,551,433 A | 11/1985 | DeBoer | |
| 4,689,406 A | 8/1987 | Banks et al. | |
| 4,738,921 A | 4/1988 | Belagaje et al. | |
| 4,745,056 A | 5/1988 | Guterman et al. | |
| 4,837,148 A | 6/1989 | Cregg | |
| 4,873,192 A | 10/1989 | Kunkel | |
| 4,876,197 A | 10/1989 | Burke et al. | |
| 4,880,734 A | 11/1989 | Burke et al. | |
| 4,929,555 A | 5/1990 | Cregg et al. | |
| 5,416,007 A | 5/1995 | Charette et al. | |
| 5,595,887 A | 1/1997 | Coolidge et al. | |
| 5,707,826 A | 1/1998 | Wagner et al. | |
| 5,728,543 A | 3/1998 | Dorschug et al. | |
| 6,130,063 A | 10/2000 | Lawlis | |
| 6,171,823 B1 | 1/2001 | Woldike et al. | |
| 6,316,224 B1 | 11/2001 | Xia | |
| 6,461,834 B1 * | 10/2002 | Dormady et al. | 435/68.1 |
| 7,335,486 B2 | 2/2008 | Wagner et al. | |
| 2005/0260701 A1 | 11/2005 | Wagner et al. | |
| 2006/0008870 A1 | 1/2006 | Wagner et al. | |

FOREIGN PATENT DOCUMENTS

| | | |
|---|---|---|
| EP | 036259 | 9/1981 |
| EP | 036776 | 9/1981 |
| EP | 063953 | 11/1982 |
| EP | 121775 | 10/1984 |
| EP | 127839 | 12/1984 |
| EP | 136829 | 4/1985 |
| EP | 136907 | 4/1985 |
| EP | 155476 | 9/1985 |
| EP | 267851 | 5/1988 |
| EP | 0978565 A1 | 2/2000 |
| WO | WO-840454 | 7/1982 |
| WO | WO-9517510 A1 | 6/1995 |
| WO | WO-9617941 A3 | 6/1996 |
| WO | WO-2000028067 A1 | 5/2000 |

OTHER PUBLICATIONS

"U.S. Appl. No. 10/997,061, Preliminary Amemdment mailed Nov. 24, 2004", 3 pgs.
"U.S. Appl. No. 10/997,061, Response filed May 4, 2007 to Restriction Requirement mailed Apr. 4, 2007", 12 pgs.
"U.S. Appl. No. 10/997,061, Restriction Requirement mailed Apr. 4, 2007", 5 pgs.
"U.S. Appl. No. 10/997,061, Non-Final Office Action mailed Feb. 14, 2008", 8 pgs.
"U.S. Appl. No. 10/997,061 Non-Final Office Action mailed Jul. 31, 2007", 11 pgs.
"U.S. Appl. No. 10/997,061 Response to Non-Final Office Action filed Oct. 31, 2007", 18 pgs.
"U.S. Appl. No. 10/997,074 Non-Final Office Action filed Dec. 15, 2006", 18 pgs.
"U.S. Appl. No. 10/997,074 Notice of Allowance mailed Sep. 21, 2007", 9 pgs.
"U.S. Appl. No. 10/997,074 Response to Non-Final Office Action filed Feb. 22, 2007", 20 pgs.
"International Application No. PCT/US03/16469 Demand filed Dec. 19, 2003", 6 pgs.
"International Application No. PCT/US03/16469 International Preliminary Examination Report mailed Feb. 9, 2005", 4 pgs.
"International Application No. PCT/US03/16469 International Search Report mailed Oct. 28, 2004", 3 pgs.
"International Application No. PCT/US03/16470 Demand filed Dec. 23, 2003", 6 pgs.

(Continued)

*Primary Examiner*—Tekchand Saidha
(74) *Attorney, Agent, or Firm*—Campbell Nelson Whipps LLC

(57) ABSTRACT

The invention provides methods for making peptides from a polypeptide containing at least one copy of the peptide using clostripain to excise the peptide from the polypeptide. The methods enable the use of a single, highly efficient enzymatic cleavage to produce any desired peptide sequence.

9 Claims, 13 Drawing Sheets

OTHER PUBLICATIONS

"International Application No. PCT/US03/16470 International Preliminary Examination Report mailed Jul. 6, 2005", 4 pgs.

"International Application No. PCT/US03/16470 International Search Report mailed Jul. 21, 2004", 2 pgs.

"International Application No. PCT/US03/16470 PCT Written Opinion mailed Sep. 29, 2004", 4 pgs.

"International Application No. PCT/US03/16649 Demand filed Dec. 24, 2003", 5 pgs.

"International Application No. PCT/US03/16649 International Preliminary Examination Report mailed May 15, 2007", 5 pgs.

"International Application No. PCT/US03/16649 International Search Report mailed Dec. 11, 2006", 7 pgs.

"Supplemental Partial European Search Report, Application No. 03734172.4-2405 PCT/US0316469", (Apr. 17, 2007), 4 pgs.

Catsimpoolas, N., et al., "Specific cleavage of cystine peptides by cyanide", *Journal of Biological Chemistry. 241*(8), (Apr. 25, 1966), 1790-6.

Dargatz, H., et al., "The Heterodimeric Protease Clostripain From Clostridium histolyticum is Encoded by a Single Gene", *Molecular & General Genetics*, 240 (1), (Jul. 1993), 140-145.

Dykes, C. W., et al., "Expression of atrial natriuretic factor as a cleavable fusion protein with chloramphenicol acetyltransferase in Escherichia coli.", *Eur J Biochem.*, 174(2), (Jun. 1, 1988), 411-6.

Forsberg, G., et al., "An evaluation of different enzymatic cleavage methods for recombinant fusion proteins, applied on des(1-3)insulin-like growth factor I.", *J Protein Chem.*, 11(2), (Apr. 1992), 201-11.

Forsberg, G., et al., "Comparison of two chemical cleavage methods for preparation of a truncated form of recombinant human insulin-like growth factor I from a secreted fusion protein.", *Biofactors*, 2(2), (Dec. 1989), 105-12.

Gram, H., et al., "A novel approach for high level production of a recombinant human parathyroid hormone fragment in Escherichia coli.", *Biotechnology* (N Y), 12(10), (Oct. 1994), 1017-23.

Knott, J. A., et al., "The isolation and characterisation of human atrial natriuretic factor produced as a fusion protein in Escherichia coli.", *Eur J Biochem.*, 174(2), (Jun. 1, 1988), 405-10.

Kunkel, T. A., "Rapid and Efficient Site-Specific Mutagenesis Without Phenotypic Selection", *Proc. Natl. Acad. Sci. USA*, 82, (1985), 488-492.

Labouesses, B., "L'Hydrolyse du Glucagon par la Clostripaine", *Bull. Soc. Chim. Biol.*, 42, (1960), 1293-1304.

Marcus, F., "Preferential cleavage at aspartyl-prolyl peptide bonds in dilute acid", *Int J Pept Protein Res.*, 25(5), (May 1985), 542-6.

Mitchell, W. M., "Cleavage at arginine residues by clostripain", *Methods Enzymol.*, 47, (1977), 165-70.

Mitchell, W. M., et al., "Purification and properties of clostridiopeptidase B (Clostripain).", *J Biol Chem.*, 243(18), (Sep. 25, 1968), 4683-92.

Moks, T., et al., "Expression of human insulin-like growth factor I in bacteria: use of optimized gene fusion vectors to facilitate protein purification", *Biochemistry*, 26(17), (Aug. 25, 1987), 5239-44.

Okamoto, K., et al., "Structural Characterization of Argingipain, a Novel Arginine-Specific Cysteine Proteinase as a Major Periodontal Pathogenic Factor from Porphyromonas gingivalis", *Archives of Biochemistry and Biophysics*, 316(2), (Feb. 1, 1995), 917-925.

Orskov, C., et al., "Biological effects and metabolic rates of glucagolike peptide-1 7-36 amide and glucagonlike peptide-1 7-37 in healthy subjects are indistinguishable", *Diabetes*, 42(5), (May 1993), 658-661.

Piers, K. L., et al., "Recombinant DNA procedures for producing small antimicrobial cationic peptides in bacteria", *Gene*, 134(1), (Nov. 30, 1993), 7-13.

Pilon, A., et al., "Ubiquitin fusion technology: bioprocessing of peptides.", *Biotechnol Prog.*, 14(4), (Jul.-Aug. 1997), 374-9.

Ray, M. V., et al., "Production of recombinant salmon calcitonin by in vitro amidation of an Escherichia coli produced precursor peptide.", *Biotechnology* (N Y), 11(1), (Jan. 1993), 64-70.

Schellenberger, V., et al., "Peptide production by a combination of gene expression, chemical synthesis, and protease-catalyzed conversion.", *Int J Pept Protein Res.*, 41(4), (Apr. 1993), 326-32.

Shen, S. H., "Multiple joined genes prevent product degradation in Escherichia coli.", *Proc Natl Acad Sci U S A.*, 81(15), (Aug. 1984), 4627-31.

Witte, V., et al., "Heterologous expression of the clostripain gene from Clostridium histolyticum in Escherichia coli and Bacillus subtilis: maturation of the clostripain precursor is coupled with self-activation.", *Microbiology*, 140 (Pt 5), (May 1994), 1175-82.

* cited by examiner

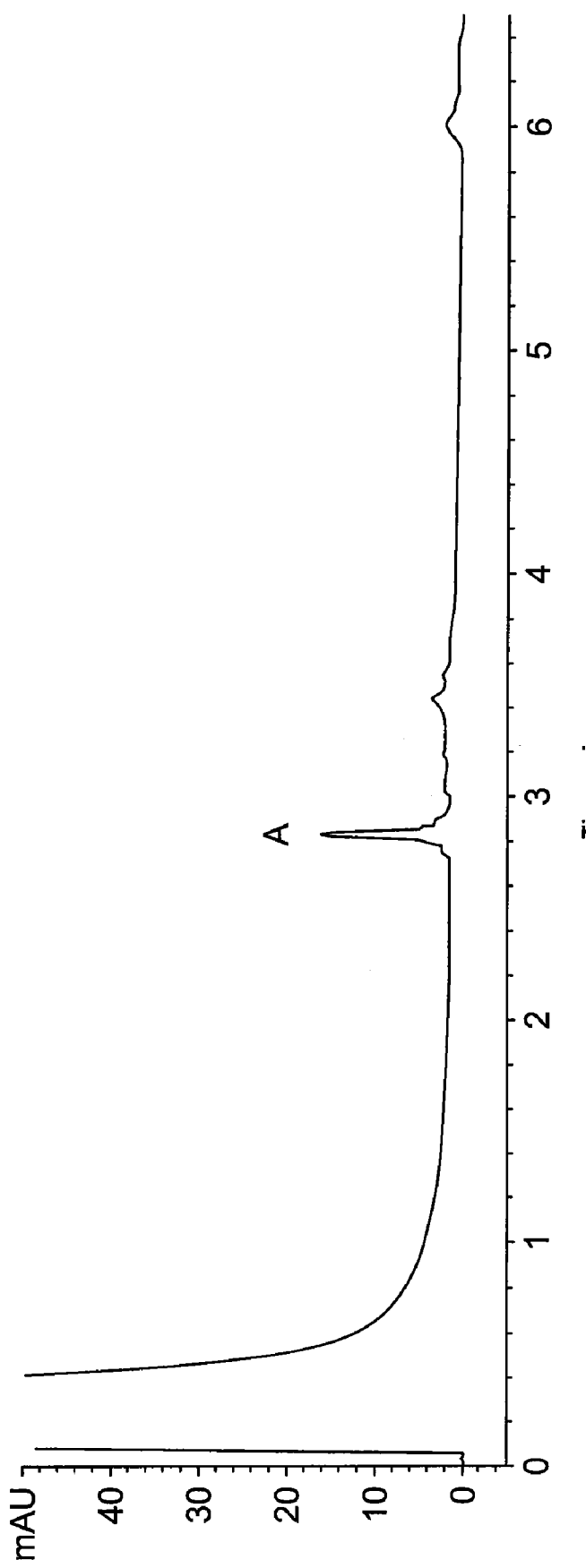

METHOD FOR UNIVERSAL ENZYMATIC PRODUCTION OF BIOACTIVE PEPTIDES

CROSS-REFERENCE TO RELATED APPLICATIONS

This application is a Division of U.S. application Ser. No. 10/997,074, filed on Nov. 24, 2004, now U.S. Pat. No. 7,335, 486, which is a Continuation under 35 U.S.C. 111(a) of PCT/US03/16470, filed on May 23, 2003 and published on Dec. 4, 2003 as WO 03/099848 A2, which claims priority under 35 U.S.C 119(e) of U.S. Provisional Application No. 60/383, 380, filed on May 24, 2002, which applications and publication are incorporated herein by reference.

BACKGROUND OF THE INVENTION

Although bioactive peptides can be produced chemically by a variety of synthesis strategies, recombinant technology offers the potential for inexpensive, large-scale production of peptides without the use of organic solvents, highly reactive reagents or potentially toxic chemicals. However, expression of short peptides in *Escherichia coli* and other microbial systems can sometimes be problematic. For example, short peptides are often degraded by the proteolytic and metabolic enzymes present in microbial host cells. Use of a fusion protein to carry the peptide of interest may help avoid cellular degradation processes because the leader protein is large enough to protect the peptide from proteolytic cleavage. Moreover, certain fusion proteins can direct the peptide to specific cellular compartments, i.e. cytoplasm, periplasm, inclusion bodies or media, thereby helping to avoid cellular degradation processes. However, while use of a fusion protein may solve certain problems, cleavage and purification of the peptide away from the fusion protein can give rise to a whole new set of problems.

Preparation of a peptide from a fusion protein in pure form requires that the peptide be released and recovered from the fusion protein by some mechanism. In many cases, the peptide of interest forms only a small portion of the fusion protein. For example, many peptidyl moieties are fused with β-galactosidase that has a molecular weight of about 100,000 daltons. A peptide with a molecular weight of about 3000 daltons would only form about 3% of the total mass of the leader protein. Also, separate isolation or purification procedures (e.g. affinity purification procedures) are generally required for each type of peptide released from a fusion protein. Release of the peptide from the fusion protein generally involves use of specific chemical or enzymatic cleavage sites that link the carrier protein to the desired peptide [Forsberg et al., *Int. J. Protein Chem.*, 11: 201-211, (1992)]. Chemical or enzymatic cleavage agents employed for such cleavages generally recognize a specific sequence. However, if that cleavage sequence is present in the peptide of interest, then a different cleavage agent must usually be employed. Use of a complex fusion partner (e.g. β-galactosidase) that may have many cleavage sites produces a complex mixture of products and complicates isolation and purification of the peptide of interest.

Chemical cleavage reagents in general recognize single or paired amino acid residues that may occur at multiple sites along the primary sequence, and therefore may be of limited utility for release of large peptides or protein domains which contain multiple internal recognition sites. However, recognition sites for chemical cleavage can be useful at the junction of short peptides and carrier proteins. Chemical cleavage reagents include cyanogen bromide, which cleaves at methionine residues [Piers et al., *Gene*, 134: 7, (1993)], N-chloro succinimide [Forsberg et al., *Biofactors*, 2: 105-112, (1989)] or BNPS-skatole [Knott et al., *Eur. J. Biochem.*, 174: 405-410, (1988); Dykes et al., *Eur. J. Biochem.*, 174: 411-416, (1988)] which cleave at tryptophan residues, dilute acid which cleaves aspartyl-prolyl bonds [Gram et al., *Bio/Technology*, 12: 1017-1023, (1994); Marcus, *Int. J. Peptide Protein Res.*, 25: 542-546, (1985)], and hydroxylamine which cleaves asparagine-glycine bonds at pH 9.0 [Moks et al., *Bio/Technology*, 5: 379-382, (1987)]. Forsberg et al., *Int. J. Protein Chem.*, 11: 201-211, (1992)

For example, Shen describes bacterial expression of a fusion protein encoding pro-insulin and β-galactosidase within insoluble inclusion bodies where the inclusion bodies were first isolated and then solubilized with formic acid prior to cleavage with cyanogen bromide. [Shen, *Proc. Nat'l. Acad. Sci.* (*USA*), 281: 4627 (1984)]. Dykes et al. describes soluble intracellular expression of a leader protein encoding α-human atrial natriuretic peptide and chloramphenicol acetyl-transferase in *E. coli* where the fusion protein was chemically cleaved with 2-(2-nitrophenylsulphenyl)-methyl-3'-bromoindolenine to release peptide. [Dykes et al., *Eur. J. Biochem.*, 174: 411 (1988)]. Ray et al. describes soluble intracellular expression in *E. coli* of a fusion protein encoding salmon calcitonin and glutathione-S-transferase where the fusion protein was cleaved with cyanogen bromide. [Ray et al., *Bio/Technology*, 11: 64 (1993)]

Proteases can provide gentler cleavage conditions and sometimes even greater cleavage specificity than chemical cleavage reagents because a protease will often cleave a specific site defined by the flanking amino acids and the protease can often perform the cleavage under physiological conditions. For example, Schellenberger et al. describes expression of a fusion protein encoding a substance P peptide (11 amino acids) and β-galactosidase within insoluble inclusion bodies, where the inclusion bodies were first isolated and then treated with chymotrypsin to cleave the leader protein. [Schellenberger et al., *Int. J. Peptide Protein Res.*, 41: 326 (1993)]. Pilon et al. describe soluble intracellular expression in *E. coli* of a leader protein encoding a peptide and ubiquitin where the fusion protein was cleaved with a ubiquitin specific protease, UCH-L3. [Pilon et al., *Biotechnol. Prog.*, 13, 374-379 (1997)]. U.S. Pat. No. 5,595,887 to Coolidge et al. discloses generalized methods of cloning and isolating peptides. U.S. Pat. No. 5,707,826 to Wagner et al. describes an enzymatic method for modification of recombinant polypeptides.

While the specificity of some proteases is understood, not all proteases have been fully characterized and there are factors that can subtly influence the specificity and efficiency of protease activity. Hence, with currently available processes cleavage of different polypeptide substrates with different proteases requires establishment of unique conditions and/or pre- or post-manipulation of the polypeptides to acquire the desired polypeptide or peptide product. Hence, improved and simplified methods for making peptides are needed. In particular, a method for making peptides is needed which can be universally applied irrespective of the amino acid sequence of the peptide.

SUMMARY OF THE INVENTION

These and other needs are achieved by the present invention which is directed to a site specific clostripain cleavage of single and multicopy polypeptides. In particular, the present invention is directed to a method that surprisingly selects a particular clostripain cleavage site from among several that may be present in a single or multicopy polypeptide. The result of this surprising characteristic of the method of the invention is the development of a versatile procedure for wide-ranging production of desired polypeptides from single and multicopy polypeptides.

An especially preferred method according to the invention involves the production of any desired peptide through recombinant techniques. This feature is accomplished through use of a single copy polypeptide having a discardable sequence ending in arginine joined to the N-terminus of the desired peptide. The cleavage of that designated arginine according to the invention is so selective that the desired peptide may contain any sequence of amino acids. The cleavage produces a single copy of the desired peptide. Thus, the method according to the invention enables the production of polypeptides having C-terminal acidic, aliphatic or aromatic amino acid residues and the production of a GLP-2(1-34) peptide. Some of the salient details of this method of the invention are summarized in the following passages.

The invention provides a method for making desired peptides using clostripain cleavage of a larger polypeptide that has at least one copy of the desired peptide. According to the invention, clostripain recognizes a site within a polypeptide as indicated in formula I and cleaves a peptide bond between amino acids $Xaa_2$ and $Xaa_3$:

$Xaa_1$-$Xaa_2$-$Xaa_3$    Formula I wherein $Xaa_1$ and $Xaa_3$ may be any non-acidic amino acid residue, $Xaa_2$ is arginine and $Xaa_1$, $Xaa_2$, $Xaa_3$ are amino acid residues within the polypeptide sequence.

Preferably, clostripain selectively recognizes a site as indicated in formula I and cleaves the peptide bond between amino acids $Xaa_2$ and $Xaa_3$ wherein $Xaa_1$ is an amino acid residue with an acidic side chain such as aspartic acid or glutamic acid or a neutral side chain such as glycine or proline; $Xaa_2$ is arginine; and $Xaa_3$ is not an acidic amino acid. Also, through the control of any one or more of pH, time, temperature and reaction solvent involved in the cleavage reaction, the rate and selectivity of the clostripain cleavage may be manipulated.

Clostripain will eventually cleave the peptide bond on the carboxyl side of any arginine or lysine appearing in an amino acid sequence irrespective of the amino acid residues adjacent arginine. Surprisingly, it has been discovered that the rate of clostripain cleavage of a polypeptide can be dramatically altered by specifically altering amino acids immediately on the N-terminal and C-terminal side of an arginine residue that acts as a clostripain cleavage site. In particular, according to the invention, this preferred clostripain cleavage of an arginine-amino acid residue peptide bond can be manipulated to be highly selective through use of an acidic amino acid residue bonded to the amino side of arginine, eg. $Xaa_1$ of foregoing Formula I. According to the invention, it has also been discovered that by manipulation of any one or more of pH, time, temperature and solvent character, the rate of clostripain cleavage can be manipulated to affect cleavage of a selected $Xaa_2$-$Xaa_3$ peptide bond of following Formula I. Combinations of these factors will enable selection of particular arginine-amino acid residue bonds from among several differing such bonds that may be present in the precursor polypeptide. Also by manipulation of the cleavage medium to include ammonia or a selected single amino acid or multi-amino acid sequence, clostripain can function as a transpeptidation enzyme so as to form a C-terminus amide or add another amino acid residue or multi-amino acid fragment to the C-terminus by peptide bond formation. Clostripain could also be used in conjunction with alcohols to form carboxyl-terminal esters.

In one aspect, the invention provides a method for producing a desired peptide from a polypeptide by cleaving at least one peptide bond within the polypeptide using clostripain. The clostripain cleaves a peptide bond between amino acids $Xaa_2$ and $Xaa_3$ of a polypeptide having the Formula II:

($Xaa_3$-Peptide$_1$-$Xaa_1$-$Xaa_2$)$_n$-$Xaa_3$-Peptide$_1$-$Xaa_1$-$Xaa_2$    Formula II In this aspect of the invention, the desired peptide has the Formula $Xaa_3$-Peptide$_1$-$Xaa_1$-$Xaa_2$. Also in this aspect of the invention, n is an integer ranging from 0 to 50. $Xaa_1$ is aspartic acid, glycine, proline or glutamic acid. $Xaa_2$ is arginine. $Xaa_3$ is not an acidic amino acid.

In another aspect, the invention provides a method for producing a desired peptide having a C-terminal acidic, aliphatic or aromatic amino acid from a polypeptide. Such a method involves cleaving with clostripain a peptide bond between amino acids $Xaa_2$ and $Xaa_3$ within a polypeptide of Formula III:

(Linker-$Xaa_3$-Peptide$_1$)$_n$-Linker-$Xaa_3$-Peptide$_1$    Formula III

In this aspect of the invention, the desired peptide has the Formula: $Xaa_3$-Peptide$_1$, wherein n is an integer ranging from 0 to 50. $Xaa_3$ is not an acidic amino acid. Linker is a cleavable peptide linker having Formula IV:

(Peptide$_5$)$_m$-$Xaa_1$-$Xaa_2$    Formula IV m is an integer ranging from 0 to 50. $Xaa_1$ is aspartic acid, glycine, proline or glutamic acid. $Xaa_2$ is arginine. Peptide$_5$ is any single or multi amino acid sequence not containing the sequence $Xaa_1$-$Xaa_2$, including but not limited to an inclusion body leader partner, discussed more fully below.

The invention further provides a method of producing a GLP peptide. The method involves the steps of (a) recombinantly producing a polypeptide of the Formula VI:

Tag-Linker-[GLP]$_q$    Formula VI wherein Tag is a sequence having SEQ ID NO:17 or 18; Linker is a cleavable peptide linker of Formula IV described above; GLP has any of the sequences given in following Table 1; and q is 0 or an integer of about 2 to about 20; (b) isolating the polypeptide of Formula VI; and (c) cleaving at least one peptide bond within the polypeptide of Formula VI using clostripain, wherein clostripain cleaves a peptide bond on the C-terminal side of $Xaa_2$.

shows the absorbance chromatogram at A280 nm. Panel (C) shows the mass of peak 1 of panel (A) which correlated to GLP-2(21-33). Panel (D) shows the mass of peak 2 of panel (A) which corresponds to GLP-2(1-33)A2G-PGDR. Panel (E) shows the mass of peak 3 in panel (A) which corresponds to GLP-2(1-33)A2G.

Figure 6A:
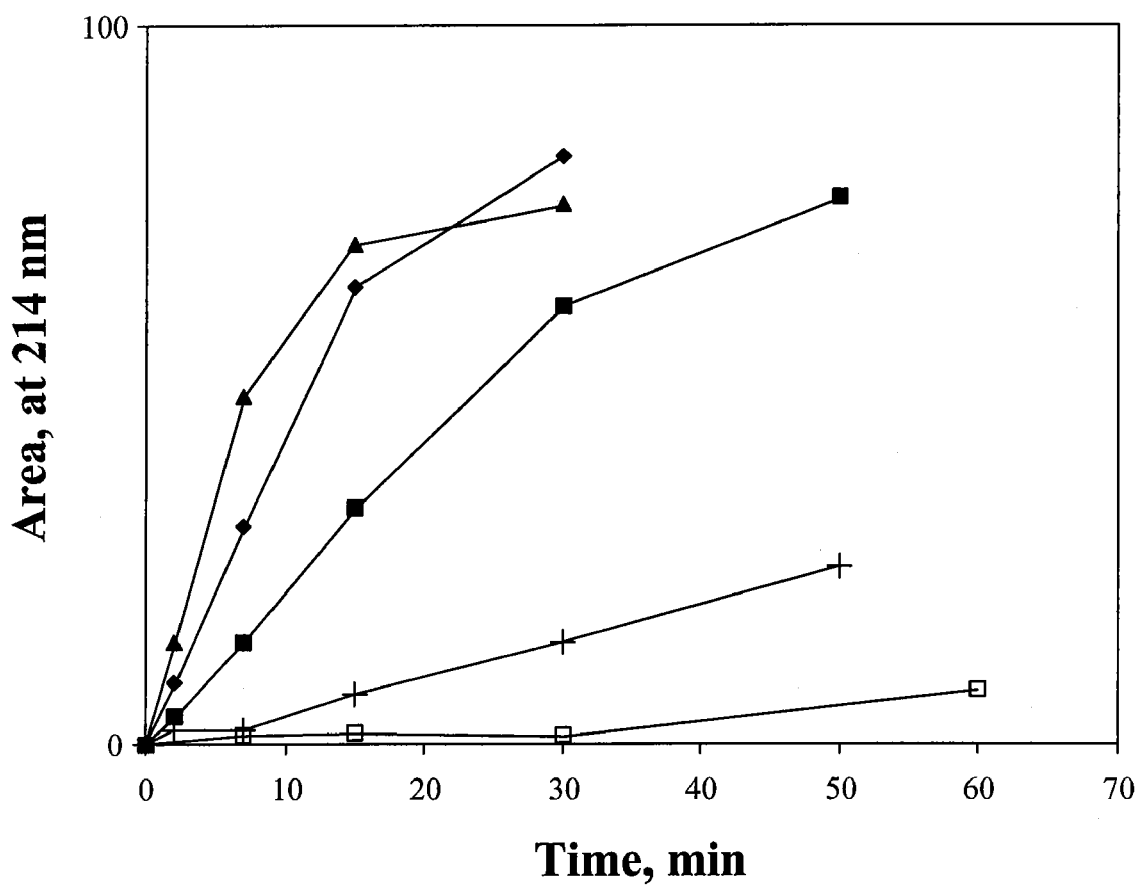
Figure 6B:
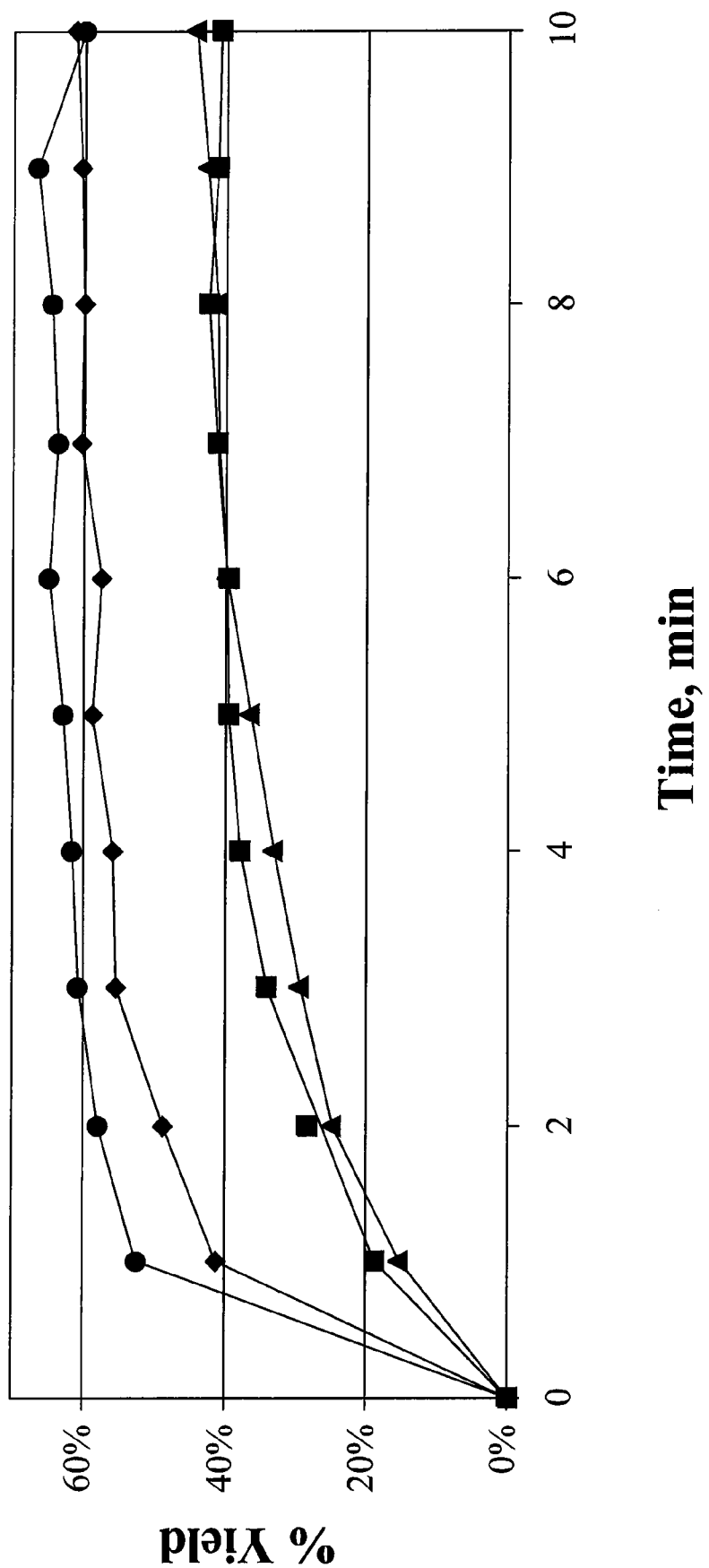

FIG. 6A: shows a plot of peak area of GLP-2(1-34) produced from the cleavage reaction as a function of time under different pH conditions; (closed triangles) pH 6.0; (closed diamonds) pH 6.5; (closed squares) pH 7.05; (+ signs) pH 7.63; (open squares) pH 8.0; FIG. 6B: shows a plot of percent yield of GLP-2(1-34) produced from the cleavage reaction as a function of time under different urea concentrations; (closed circles) 0 M; (closed diamonds) 0.5 M; (closed squares) 1.0 M; (closed triangles) 1.5 M urea.

Figure 7A:
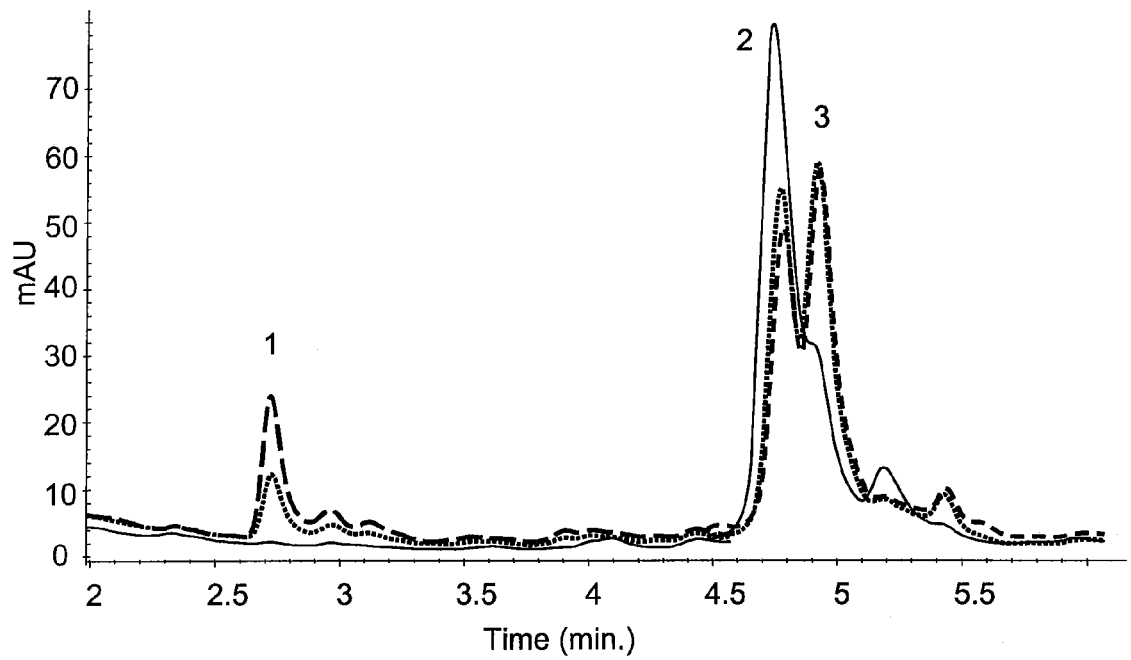
Figure 7B:
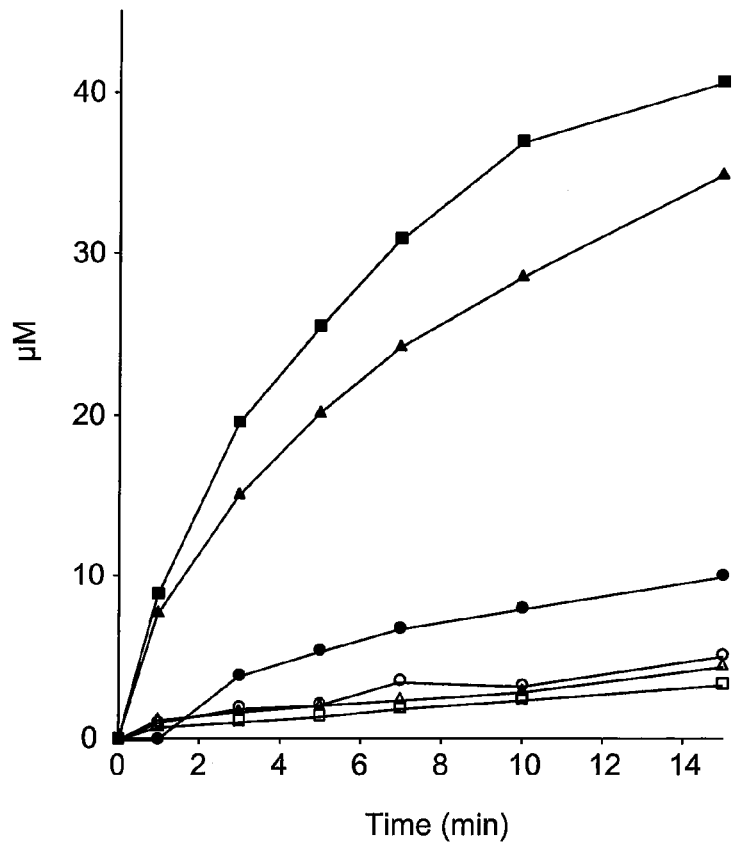

FIGS. 7A and 7B illustrate the effect of organic solvents on the rate and extent of cleavage of a precursor polypeptide T7tag-Vg-VDDR-GLP-2(1-33,A2G) by clostripain. FIG. 7A: (dashed line is 10% ethanol) (dotted line is 20% ethanol) (solid line is 35% ethanol). Peak 1 is GLP-2(21-33), Peak 2 is GLP-2(1-33,A2G) and Peak 3 is the T7tag-Vg-VDDR-GLP-2(1-33,A2G) precursor polypeptide. FIG. 7B: (closed square) rate of formation of GLP-2(1-33,A2G) in 30% ethanol; (closed triangle) rate of formation of GLP-2(1-33,A2G) in 30% acetonitrile; (closed circle) rate of formation of GLP-2(1-33,A2G) in the absence of organic solvent; (open circle) rate of formation of GLP-2(21-33) in the absence of an organic solvent; (open triangle) rate of formation of GLP-2 (21-33) in 30% acetonitrile; (open square) rate of formation of GLP-2(21-33) in 30% ethanol.

Figure 8A:
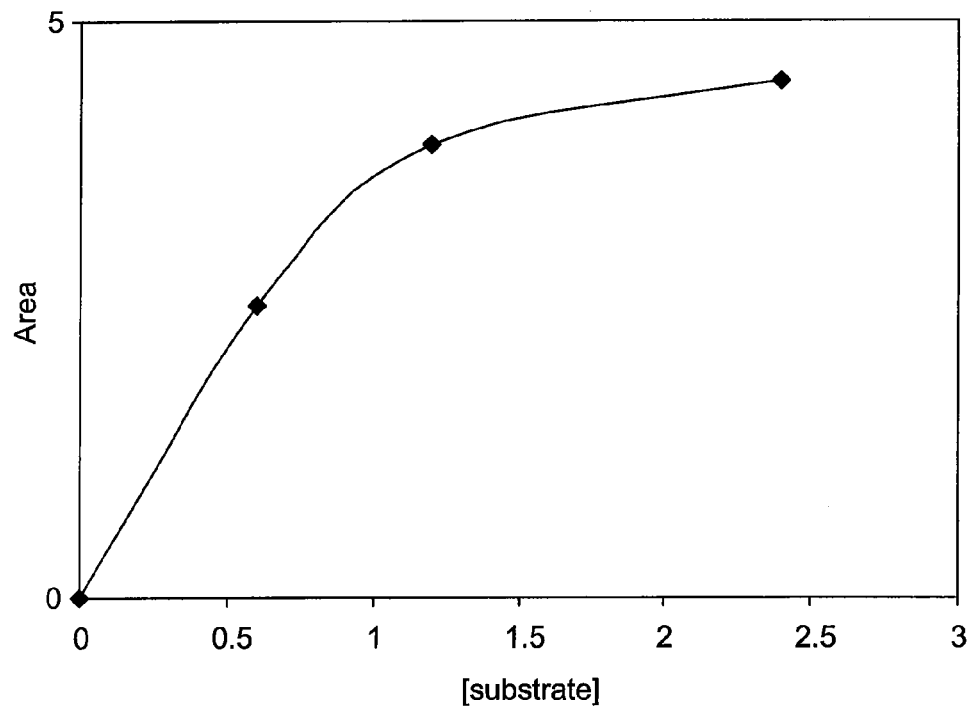
Figure 8B:
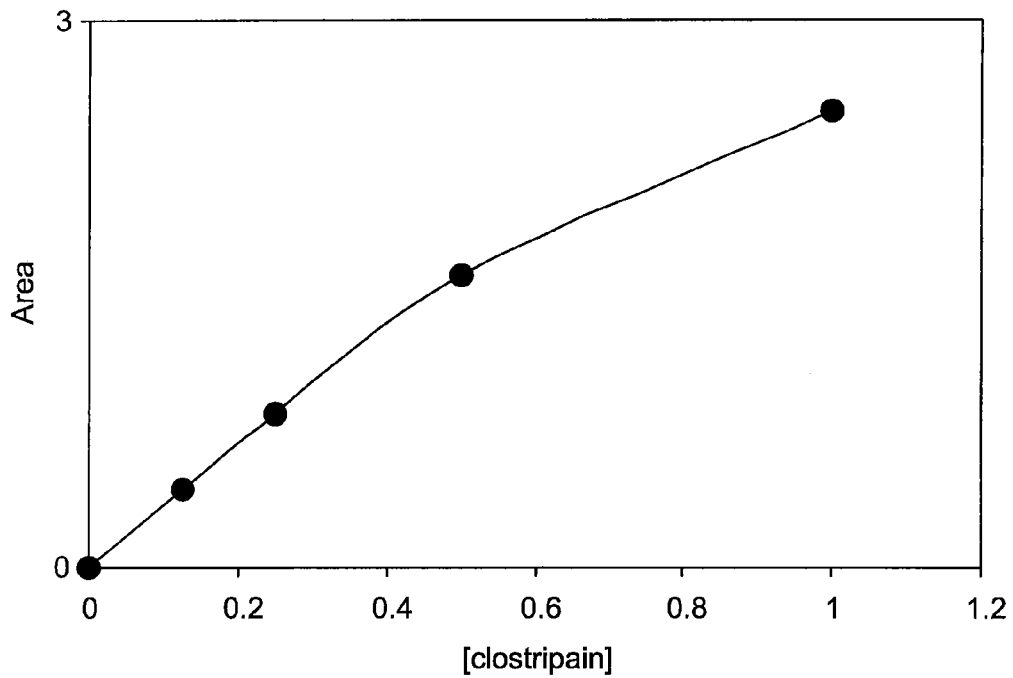

FIG. 8A shows the effect of precursor polypeptide concentration on the rate of cleavage by clostripain. FIG. 8B shows the effect of clostripain concentration on the rate of cleavage of a precursor polypeptide. Area was computed by integrating the HPLC peak area detected at 280 nm.

Figure 9:
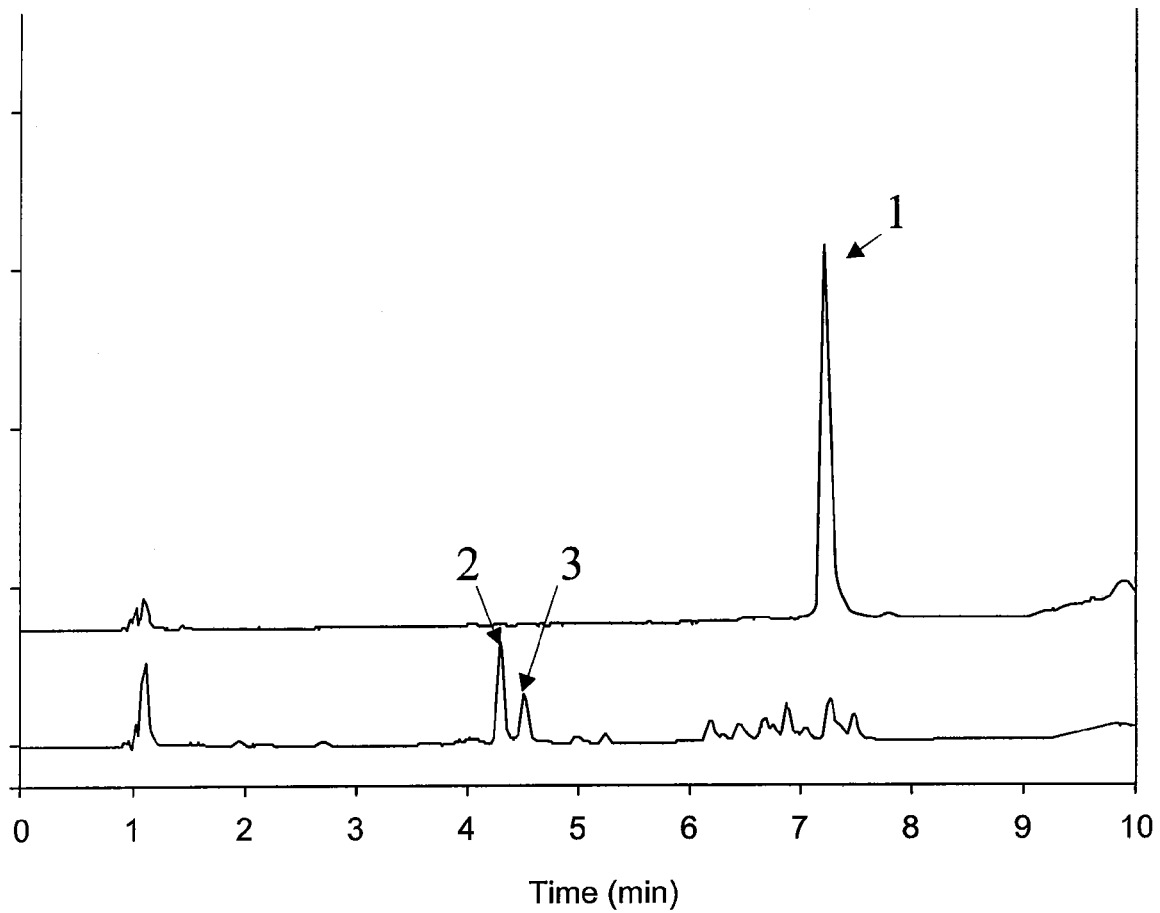

FIG. 9 illustrates the production of C-terminal amidated cleavage product GLP-1(7-36)-NH$_2$. Peak (1) is T7tag-GS-[GPGDR-GLP-1(7-36)-AFL]$_3$ at time 0. Peak (2) is GLP-1 (7-36)-NH$_2$ at 180 minutes, Peak (3) is GLP-1(7-36)-OH at time 180 minutes.

FIG. 10 shows the production of GLP-1(7-37) as identified by LC/MS analysis.

DEFINITIONS OF THE INVENTION

Abbreviations: LC-MS: liquid chromatography-mass spectroscopy; TFA: trifloroacetic acid; DTT: dithiothreitol; DTE: dithioerythritol; NMM: N-methyl-morpholine.

An "Amino acid analog" includes amino acids that are in the D rather than L form, as well as other well known amino acid analogs, e.g., N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, N-methyl-alanine, para-benzoyl-phenylalanine, phenylglycine, propargylglycine, sarcosine, N-acetylserine, N-formylmethionine, 3-methyl-histidine, 5-hydroxylysine, norleucine, norvaline, orthonitro-phenylglycine and other similar amino acids.

The terms, "cells," "cell cultures", "Recombinant host cells", "host cells", and other such terms denote, for example, microorganisms, insect cells, and mammalian cells, that can be, or have been, used as recipients for nucleic acid constructs or expression cassettes, and include the progeny of the original cell which has been transformed. It is understood that the progeny of a single parental cell may not necessarily be completely identical in morphology or in genomic or total DNA complement as the original parent, due to natural, accidental, or deliberate mutation. Many cells are available from ATCC and commercial sources. Many mammalian cell lines are known in the art and include, but are not limited to, Chinese hamster ovary (CHO) cells, HeLa cells, baby hamster kidney (BHK) cells, monkey kidney cells (COS), and human hepatocellular carcinoma cells (e.g., Hep G2). Many prokaryotic cells are known in the art and include, but are not limited to, *Escherichia coli* and *Salmonella typhimurium*. [Sambrook and Russell, Molecular Cloning: A Laboratory Manual, 3rd edition (Jan. 15, 2001) Cold Spring Harbor Laboratory Press, ISBN: 0879695765]. Many insect cells are known in the art and include, but are not limited to, silkworm cells and mosquito cells. [Franke and Hruby, *J. Gen. Virol.*, 66:2761 (1985); Marumoto et al., *J. Gen. Virol.*, 68:2599 (1987)].

A "conservative amino acid" refers to an amino acid that is functionally similar to a second amino acid. Such amino acids may be substituted for each other in a polypeptide with minimal disturbance to the structure or function of the polypeptide. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Neutral: Asparagine (N), Glutamine (Q). Examples of other synthetic and non-genetically encoded amino acid types are provided herein.

A "cleavable peptide linker" refers to a peptide sequence having a clostripain cleavage recognition sequence.

A "coding sequence" is a nucleic acid sequence that is translated into a polypeptide, such as a preselected polypeptide, usually via mRNA. The boundaries of the coding sequence are determined by a translation start codon at the 5'-terminus and a translation stop codon at the 3'-terminus of an mRNA. A coding sequence can include, but is not limited to, cDNA, and recombinant nucleic acid sequences.

The term "gene" is used broadly to refer to any segment of nucleic acid that encodes a preselected polypeptide. Thus, a gene may include a coding sequence for a preselected polypeptide and/or the regulatory sequences required for expression. A gene can be obtained from a variety of sources. For example, a gene can be cloned or PCR amplified from a source of interest, or it can be synthesized from known or predicted sequence information.

An "inclusion body" is an amorphous polypeptide deposit in the cytoplasm of a cell. In general, inclusion bodies comprise aggregated protein that is improperly folded or inappropriately processed.

An "inclusion body leader partner" is a peptide that causes a polypeptide to which it is attached to form an inclusion body when expressed within a bacterial cell. The inclusion body leader partners of the invention can be altered to confer isolation enhancement onto an inclusion body that contains the altered inclusion body leader partner.

The term "lysate" as used herein refers to the product resulting from the breakage of cells. Such cells include both prokaryotic and eukaryotic cells. For example, bacteria may be lysed though a large number of art recognized methods. Such methods include, but are not limited to, treatment of cells with lysozyme, French press, treatment with urea, organic acids, and freeze thaw methods. Methods for lysing cells are known and have been described. (Sambrook and Russell, Molecular Cloning: A Laboratory Manual, 3rd edition (Jan. 15, 2001) Cold Spring Harbor Laboratory Press, ISBN: 0879695765; Stratagene, La Jolla, Calif.).

An "open reading frame" (ORF) is a region of a nucleic acid sequence that encodes a polypeptide.

"Operably-linked" refers to the association of nucleic acid sequences or amino acid sequences on a single nucleic acid fragment or a single amino acid sequence so that the function of one is affected by the other. For example, a regulatory DNA sequence is said to be "operably linked to" or "associated with" a DNA sequence that codes for an RNA if the two sequences are situated such that the regulatory DNA sequence affects expression of the coding DNA sequence (i.e., that the coding sequence or functional RNA is under the transcriptional control of the promoter). In an example related to amino acid sequences, an inclusion body leader partner is said to be operably linked to a preselected amino acid sequence when the inclusion body leader partner causes a protein construct to form an inclusion body. In another example, a signal sequence is said to be operably linked to a preselected amino acid when the signal sequence directs the protein construct to a specific location in a cell.

The term "polypeptide" refers to a polymer of amino acids and does not limit the size to a specific length of the product. However, as used herein, a polypeptide is generally longer than a peptide and may include one or more copies of a peptide of interest (the terms "peptide of interest" and "desired peptide" are used synonymously herein). This term also optionally includes post expression modifications of the polypeptide, for example, glycosylations, acetylations, phosphorylations and the like. Included within the definition are, for example, polypeptides containing one or more analogues of an amino acid or labeled amino acids.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence. Promoters may be derived in their entirety from a native gene, or be composed of different elements derived from different promoters found in nature, or even be comprised of synthetic DNA segments. A promoter may also contain DNA segments that are involved in the binding of protein factors that control the effectiveness of transcription initiation in response to physiological or environmental conditions.

The term "purification stability" refers to the isolation characteristics of an inclusion body formed from a polypeptide having an inclusion body leader partner operably linked to a polypeptide. High purification stability indicates that an inclusion body can be isolated from a cell in which it was produced. Low purification stability indicates that the inclusion body is unstable during purification due to dissociation of the polypeptides forming the inclusion body.

When referring to a polypeptide or nucleic acid, "isolated" means that the polypeptide or nucleic acid has been removed from its natural source. An isolated polypeptide or nucleic acid may be present within a non-native host cell and so the polypeptide or nucleic acid is therefore not necessarily "purified."

The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

"Regulated promoter" refers to a promoter that directs gene expression in a controlled manner rather than in a constitutive manner. Regulated promoters include inducible promoters and repressable promoters. Such promoters may include natural and synthetic sequences as well as sequences that may be a combination of synthetic and natural sequences. Different promoters may direct the expression of a gene in response to different environmental conditions. Typical regulated promoters useful in the invention include, but are not limited to, promoters used to regulate metabolism (e.g. an IPTG-inducible lac promoter) heat-shock promoters (e.g. an SOS promoter), and bacteriophage promoters (e.g. a T7 promoter).

A "ribosome-binding site" is a DNA sequence that encodes a site on an mRNA at which the small and large subunits of a ribosome associate to form an intact ribosome and initiate translation of the mRNA. Ribosome binding site consensus sequences include AGGA or GAGG and are usually located some 8 to 13 nucleotides upstream (5') of the initiator AUG codon on the mRNA. Many ribosome-binding sites are known in the art. [Shine et al., *Nature*, 254: 34, (1975); Steitz et al., "Genetic signals and nucleotide sequences in messenger RNA", in: Biological Regulation and Development: Gene Expression (ed. R. F. Goldberger) (1979)].

A "selectable marker" is generally encoded on the nucleic acid being introduced into the recipient cell. However, co-transfection of selectable marker can also be used during introduction of nucleic acid into a host cell. Selectable markers that can be expressed in the recipient host cell may include, but are not limited to, genes which render the recipient host cell resistant to drugs such as actinomycin $C_1$, actinomycin D, amphotericin, ampicillin, bleomycin, carbenicillin, chloramphenicol, geneticin, gentamycin, hygromycin B, kanamycin monosulfate, methotrexate, mitomycin C, neomycin B sulfate, novobiocin sodium salt, penicillin G sodium salt, puromycin dihydrochloride, rifampicin, streptomycin sulfate, tetracycline hydrochloride, and erythromycin. [Davies et al., *Ann. Rev. Microbiol.*, 32: 469, 1978]. Selectable markers may also include biosynthetic genes, such as those in the histidine, tryptophan, and leucine biosynthetic pathways. Upon transfection or tranformation of a host cell, the cell is placed into contact with an appropriate selection marker.

The term "self-adhesion" refers to the association between polypeptides that have an inclusion body leader partner to form an inclusion body. Self-adhesion may affect the purification stability of an inclusion body formed from the polypeptide. Self-adhesion that is too great produces inclusion bodies having polypeptides that are so tightly associated with each other that it is difficult to separate individual polypeptides from an isolated inclusion body. Self-adhesion that is too low produces inclusion bodies that are unstable during isolation due to dissociation of the polypeptides that form the inclusion body. Self-adhesion can be regulated by altering the amino acid sequence of an inclusion body leader partner.

A "Signal sequence" is a region in a protein or polypeptide responsible for directing an operably linked polypeptide to a cellular location or compartment designated by the signal sequence. For example, signal sequences direct operably linked polypeptides to the inner membrane, periplasmic space, and outer membrane in bacteria. The nucleic acid and amino acid sequences of such signal sequences are well known in the art and have been reported. [Watson, Molecular Biology of the Gene, 4th edition, Benjamin/Cummings Publishing Company, Inc., Menlo Park, Calif. (1987); Masui et al., in: Experimental Manipulation of Gene Expression, (1983); Ghrayeb et al., *EMBO J.*, 3: 2437 (1984); Oka et al., *Proc. Natl. Acad. Sci. USA*, 82: 7212 (1985); Palva et al., *Proc. Natl. Acad. Sci. USA*, 79: 5582 (1982); U.S. Pat. No. 4,336,336].

Signal sequences, preferably for use in insect cells, can be derived from genes for secreted insect or baculovirus proteins, such as the baculovirus polyhedrin gene [Carbonell et al., *Gene*, 73: 409 (1988)]. Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, signal sequences of non-insect origin, such as those derived from genes encoding human ∀-interferon [Maeda et al., *Nature*, 315:592 (1985)], human gastrin-releasing peptide [Lebacq-Verheyden et al., *Mol. Cell. Biol.*, 8: 3129 (1988)], human IL-2 [Smith et al., *Proc. Natl. Acad. Sci. USA*, 82: 8404 (1985)], mouse IL-3 [Miyajima et al., *Gene*, 58: 273 (1987)] and human glucocerebrosidase [Martin et al., *DNA*, 7: 99 (1988)], can also be used to provide for secretion in insects.

The term "solubility" refers to the amount of a substance that can be dissolved in a unit volume of solvent. For example, solubility as used herein refers to the ability of a polypeptide to be resuspended in a volume of solvent, such as a biological buffer.

A "Tag" sequence refers to an amino acid sequence that is operably linked to a peptide or protein. Such tag sequences may provide for the increased expression of a desired peptide or protein. Such tag sequences may also form a cleavable peptide linker when they are operably linked to another peptide or protein. Examples of tag sequences include, but are not limited to, the sequences indicated in SEQ ID NOs: 17 and 18.

A "transcription terminator sequence" is a signal within DNA that functions to stop RNA synthesis at a specific point along the DNA template. A transcription terminator may be either rho factor dependent or independent. An example of a transcription terminator sequence is the T7 terminator. Transcription terminators are known in the art and may be isolated from commercially available vectors according to recombinant methods known in the art. (Sambrook and Russell, Molecular Cloning: A Laboratory Manual, 3rd edition (Jan. 15, 2001) Cold Spring Harbor Laboratory Press, ISBN: 0879695765; Stratagene, La Jolla, Calif.).

"Transformation" refers to the insertion of an exogenous nucleic acid sequence into a host cell, irrespective of the method used for the insertion. For example, direct uptake, transduction, f-mating or electroporation may be used to introduce a nucleic acid sequence into a host cell. The exogenous nucleic acid sequence may be maintained as a non-integrated vector, for example, a plasmid, or alternatively, may be integrated into the host genome.

A "translation initiation sequence" refers to a DNA sequence that codes for a sequence in a transcribed mRNA that is optimized for high levels of translation initiation. Numerous translation initiation sequences are known in the art. A translation inititation sequence may include an optimized ribosome-binding site. In the present invention, bacterial translational start sequences are preferred. Such translation initiation sequences are available in the art and may be obtained from bacteriophage T7, bacteriophage 10, and the gene encoding ompT. Those of skill in the art can readily obtain and clone translation initiation sequences from a variety of commercially available plasmids, such as the pET (plasmid for expression of T7 RNA polymerase) series of plasmids. (Stratagene, La Jolla, Calif.).

A "unit" of clostripain activity is defined as the amount of enzyme required to transform 1 mole of benzolyl-L-arginine ethyl ester (BAEE) to benzoyl-L-arginine per minute at 25° C. under defined reaction conditions. The transformation is measured spectroscopically at 253 nm. The assay solution contained 0.25 mM BAEE, 10 mM HEPES (pH 7.6), 2 mM $CaCl_2$, and 2.5 mM DTT.

A "variant" polypeptide is intended to be a polypeptide derived from the reference polypeptide by deletion, substitution or addition of one or more amino acids to the N-terminal and/or C-terminal end of the native polypeptide; deletion or addition of one or more amino acids at one or more sites in the native protein; or substitution of one or more amino acids at one or more sites in the reference protein. Such substitutions or insertions are preferably conservative amino acid substitutions. Methods for such manipulations are generally known in the art. [Kunkel, *Proc. Natl. Acad. Sci. USA*, 82:488, (1985); Kunkel et al., *Methods in Enzymol.*, 154:367 (1987); U.S. Pat. No. 4,873,192; Walker and Gaastra, eds. (1983) *Techniques in Molecular Biology* (MacMillan Publishing Company, New York] and the references cited therein. Guidance as to appropriate amino acid substitutions that do not affect biological activity of the protein of interest may be found in the model of Dayhoff et al. [(1978) *Atlas of Protein Sequence and Structure* (Natl. Biomed. Res. Found., Washington, D.C.)].

DETAILED DESCRIPTION OF THE INVENTION

The invention provides methods for efficiently making peptides. The peptides are made using recombinant and proteolytic procedures. The invention enables the wide-ranging use of a single cleavage enzyme whose selectivity can be manipulated. In particular, the enzyme, clostripain, can be manipulated to cleave a particular site when the same primary cleavage site appears elsewhere in the peptide. Although limited to initial cleavage at a C-terminal side of arginine residues, the method provides versatility. The versatility arises from the surprising ability to manipulate clostripain so that it will cleave at a selected arginine even though arginine or lysine appears elsewhere within the peptide sequence.

The need to avoid reassimilation of an expressed, desired peptide by host expression cells dictates that the desired peptide should have a significantly high molecular weight and varied amino acid sequence. Such peptide features are desirable when recombinant peptides are being produced. This need means that the expressed polypeptide be formed either as a multicopy of the desired peptide or as a combination of the desired peptide be linked to a discardable peptide sequence. Use of the former multicopy scheme provides multiple copies of the desired peptide under certain circumstances and the desired peptide with several additional amino acid residues at its N and C termini under all other circumstances. Use of the latter single copy scheme provides at least a single copy of the desired peptide.

According to the invention, the latter scheme may be employed to produce virtually any desired peptide. The discardable sequence is manipulated according to the invention in part to have arginine as its carboxyl end. The arginine is in turn coupled by its peptide bond to the N-terminus of the desired peptide. The cleavage of that designated arginine according to the invention is so selective that the desired peptide may contain virtually any sequence of amino acids. The cleavage produces a single copy of the desired peptide.

Although it is not to be regarded as a limitation of the invention, the selectivity of this enzymatic cleavage is believed to be the result of the influence of secondary binding sites of the substrate with the enzyme, clostripain. These secondary sites are adjacent to the primary cleavage site and are known as the P and P' sites. There may be one or multiple P and P' sites. The P sites align with the amino acid residues on the amino side of the scissile bond while the P' sites align with the amino acid residues on the carboxyl side of the scissile bond. Thus, the scissile bond resides between the P and the P' bond. The corresponding sites of the enzyme are termed S and S' sites. It is believed that the side chain character of the P and P' amino acid residues immediately adjacent the primary cleavage residue have significant influence upon the ability of the enzyme to bind with and cleave the peptide bond at the primary cleavage site.

For clostripain, it has been discovered that an acidic amino acid residue occupying the $P_2$ site (amino side) immediately adjacent to the $P_1$ primary cleavage amino acid residue, arginine, causes highly selective, rapid attack of clostripain upon that particular primary cleavage site. It has also been discovered that an acidic amino acid residue occupying the $P_1'$ site (carboxyl side) immediately adjacent the primary cleavage site causes repulsion of, and extremely slow attack of; clostripain upon the primary cleavage site.

Thus, according to a preferred method of the invention, a polypeptide that has at least one copy of a peptide of interest may be recombinantly produced. The production may be of a soluble polypeptide or, as described in the copending applications filed on even date herewith and having attorney docket numbers 1627.009PRV and 1627.010PRV, the disclosures of which are incorporated herein by reference, an inclusion body preparation containing at least a substantially insoluble mass of polypeptide. Next, the polypeptide is proteolytically cleaved using clostripain to produce the peptide of interest. By manipulating the polypeptide and/or the cleavage conditions, peptides having any C-terminal residue can be produced. Further, under the method of the present invention or by combining the method of this invention with those disclosed in the copending patent applications with attorney docket numbers 1627.011PRV, 1627.012PRV, 1627.013PRV and 1627.026PRV filed on even date herewith, the disclosures of which are incorporated herein by reference, peptides having any C-terminal residue amide can be produced. For example GLP-2(1-33)-$NH_2$ can be produced from GLP-2(1-33)CH through use of the method disclosed in those copending applications.

The Clostripain Cleavage Process According to the Invention

According to the invention, clostripain is used in a selective manner to affect preferential cleavage at a selected arginine site. As explained below, clostripain is recognized to cleave at the carboxyl side of arginine and lysine residues in peptides. One of the surprising features of the present invention is the discovery of the ability to provide a selective cleavage site for clostripain so that it will preferentially cleave at a designated arginine even though other arginine or lysine residues are present within the peptide. Multicopy polypeptides having arginine residues at the inchoate C-termini of the desired peptide product copies within the polypeptide and also having arginine or lysine residues within the desired peptide sequence can be efficiently and selectively cleaved according to the invention to produce the desired peptide product.

Moreover, the enzymatic cleavage, precursor polypeptide and desired peptide product can be manipulated so that the C-terminus of the peptide product may be any amino acid residue. This feature is surprising in view of the cleavage preference of clostripain toward arginine. This feature is accomplished through use of a discardable sequence ending in arginine and joined to the N-terminus of the desired peptide. The cleavage of that designated arginine according to the invention is so selective that the desired peptide may contain any sequence of amino acids. The cleavage produces a single copy of the desired peptide.

Traditional Clostripain Cleavage Conditions

Clostripain (EC 3.4.22.8) is an extracellular protease from Clostridia that can be recovered from the culture filtrate of *Clostridium histolyticum*. Clostripain has both proteolytic and amidase/esterase activity. [Mitchell, W. M, Harrington, W. F., *J. of Biol. Chem.*, 243 (18): 4683-4692 (1968)]. Clostripain is a heterodimer with a molecular weight of about 50,000 and an isoelectric point of pH 4.8 to 4.9. Clostripain proteolytic activity is inhibited, for example, by tosyl-L-lysine chloromethyl ketone, hydrogen peroxide, $Co^{++}$, $Cu^{++}$ or $Cd^{++}$ ions, citrate, or $Ca^{++}$ chelators, such as EGTA and EDTA. Examples of clostripain activators include cysteine, mercaptoethanol, dithiothreitol and calcium ions.

Clostripain is generally understood to have specificity for cleavage of Arg-Xaa linkages, though some cleavage can occur at lysine residues under certain reaction conditions. Thus, in the isolated B chain of insulin, clostripain cleaves the Arg-Gly linkage 500 times more rapidly than the Lys-Ala linkage. In glucagon, only the Arg-Arg, the Arg-Ala and the Lys-Tyr sites are cleaved. The relative initial rates of hydrolysis of these three bonds are 1, $\frac{1}{7}$ and $\frac{1}{300}$. [Labouesses B., *Bull. Soc. Chim. Biol.*, 42: 1293, (1960)].

Clostripain Cleavage According to the Invention

According to the invention, amino acids flanking arginine can strongly influence clostripain cleavage. In particular, clostripain has a strong preference for a polypeptide having a cleavage site as shown in Formula I, where the cleavage occurs at a peptide bond after amino acid $Xaa_2$:

$$Xaa_1\text{-}Xaa_2\text{-}Xaa_3 \qquad (I)$$

wherein
$Xaa_1$ aspartic acid, glycine, proline or glutamic acid;
$Xaa_2$ is arginine; and
$Xaa_3$ is not an acidic amino acid.

According to the method of the invention, a precursor polypeptide containing at least one copy of a desired peptide is first recombinantly produced. The production may be of a soluble precursor polypeptide or may be an inclusion body preparation containing at least a substantially insoluble mass of precursor polypeptide. Next, the precursor polypeptide is proteolytically cleaved using clostripain to produce the desired peptide. The proteolytic reaction can be performed on the solubilized cellular contents in situations where the precursor polypeptide is soluble. Or, it may be performed on crude preparations of inclusion bodies. In either situation, separation steps prior to or following the enzymatic cleavage may be employed. Use of varying concentrations of urea in the medium containing the crude cellular contents or inclusion bodies in optional combination with such separation steps may also be employed. A reaction vessel can also be used that permits continuous recovery and separation of the peptide away from the uncleaved precursor polypeptide and the clostripain. Use of such a method produces large amounts of pure peptide in essentially one step, eliminating numerous processing steps typically used in currently available procedures.

Clostripain can be used to cleave purified or impure preparations of the precursor polypeptide. The precursor polypeptide can be in solution or it can be an insoluble mass. For example, the precursor polypeptide can be in a preparation of inclusion bodies that becomes soluble in the reaction mixture. According to the invention, clostripain is active in high levels of reagents that are commonly used to solubilize proteins. For example, clostripain is active in high levels of urea. Therefore, concentrations of urea ranging up to about 8M can readily be used in the clostripain cleavage reaction.

Little purification of the precursor polypeptide is required when an inclusion body preparation of the precursor polypeptide is used as a substrate for clostripain cleavage. Essentially, host cells having a recombinant nucleic acid encoding the precursor polypeptide are grown under conditions that permit expression of the precursor polypeptide. Cells are grown to high cell densities, then collected, washed and broken open, for example, by sonication. Inclusion bodies are then collected, washed in water and employed without further purification.

Up to about 8 M urea can be used to solubilize insoluble precursor polypeptides, for example, inclusion body preparations of precursor polypeptides. The amount of urea employed can vary depending on the precursor polypeptide.

For example, about 0 M to about 8 M urea can be employed in the clostripain reaction mixture to solubilize the precursor polypeptide. Preferred concentrations of urea are about 4 M urea to about 8 M urea.

Urea can also be used in the clostripain reaction. Concentrations of up to 8 M urea can be used in the clostripain cleavage. Preferred concentrations of urea are about 0.0 to about 4 M urea. More preferred concentrations of urea are about 0.0 to about 1.0 urea. Even more preferred concentrations of urea are about 0.0 to about 0.5 M urea.

In some cases, it may be preferable to remove the urea before cleavage with clostripain. In such cases, urea may be removed by dialysis, gel filtration, tangential flow filtration (TFF), a multiplicity of chromatographic procedures and the like.

Moreover, according to the invention, the cleavage reaction conditions can be modified so that clostripain will have an even stronger preference for cleavage at sites having formula I. Several factors can be modified or implemented to obtain the desired product. Thus, by adjusting the pH and adding organic solvents, such as ethanol or acetonitrile, or by using a selected amount of enzyme relative to precursor polypeptide and/or by using selected reaction times and/or by continuously removing the peptide as it is formed, cleavage at undesired sites can be avoided.

Appropriate inorganic or organic buffers can be used to control the pH of the cleavage reaction. Such buffers include phosphate, Tris, glycine, HEPES and the like. The pH of the reaction can vary between pH 4 and pH 12. However, a pH range between pH 6 and pH 10 is preferred. For amidation, a pH range between 8.5 and 10.5 is preferred. While for hydrolysis, a pH range between 6 and 7 is preferred. When the cleavage is performed on precursor polypeptides in the absence or presence of significant amounts of urea, pH values ranging from about 6.0 to about 6.9 are preferred.

The activity of the clostripain enzyme has surprisingly been found to be influenced by the presence of organic solvents. For example, ethanol and acetonitrile are shown herein to increase the rate of substrate cleavage as well as the overall yield of product formed from the cleavage of a precursor polypeptide (FIG. 7). Another surprising result is that organic solvents influence the cleavage specificity of clostripain. Thus, the presence of an organic solvent can dramatically influence the preferential hydrolysis of one cleavage site in a precursor polypeptide relative to another cleavage site within the same precursor polypeptide. This characteristic of clostripain can be exploited to design precursor polypeptides that are rapidly and preferentially cleaved at specific sites within the precursor polypeptide.

The clostripain enzyme can be activated at similar pH ranges. A suitable buffer substance, for example phosphate, Tris, HEPES, glycine and the like, can be added to maintain the pH.

The concentration of the precursor polypeptide employed during the cleavage is, for example, between 0.01 mg/ml and 100 mg/ml, preferably between 0.1 mg/ml and 20 mg/ml. The ratio of polypeptide to clostripain is, in mg to units about 1:0.01 to about 1:1,000, preferably about 1:0.1 to about 1:50.

The temperature of the reaction can also be varied over a wide range and may depend upon the selected reaction conditions. Such a range can be between 0° C. and +80° C. A preferred temperature range is generally between +5° C. and +60° C. Amidation is preferably conducted at a temperature between 5° C. and 60° C., and is more preferably conducted at a temperature between 35° C. and 60° C., and is most preferably conducted at 45° C. Hydrolysis is preferably conducted at a temperature between 20° C. and 30° C., and more preferably is conducted at 25° C.

The time required for the conversion of the precursor polypeptides into the peptides of interest can vary and one of skill in the art can readily ascertain an appropriate reaction time. For example, the reaction time can vary between about 1 min and 48 h. However, a reaction time of between 0.5 h and 6 h is preferred. A reaction time of 0.5 h and 2 hours is more preferred. In some embodiments, the reaction mixture is preferably placed in a reaction vessel that permits continuous removal of the peptide product. For example, the reaction vessel can have a filter that permits the peptide product of interest to pass through but that retains the precursor polypeptide and the clostripain. An example of an appropriate filtration system is tangential flow filtration (TFF). Reaction buffer, substrate and other components of the reaction mixture can be added batchwise or continuously as the peptide is removed and the reaction volume is lost.

The enzyme can be activated before use in a suitable manner in the presence of a mercaptan. Mercaptans suitable for activation are compounds containing SH groups. Examples of such activating compounds include DTT, DTE, mercaptoethanol, thioglycolic acid or cysteine. Cysteine is preferably used. The concentration of the mercaptan can also vary. In general, concentrations between about 0.01 mM and 50 mM are useful. Preferred mercaptan concentrations include concentrations between about 0.05 mM and 5 mM. More preferred mercaptan concentrations are between about 0.5 mM and 2 mM. The activation temperature can be between 0° C. and 80° C. Preferably the activation temperature can be between 0° C. and 40° C., more preferably the activation temperature is between 0° C. and 30° C. Most preferably, the activation temperature is between 15° C. and 25° C.

Clostripain can be purchased from commercially available sources or it can be prepared from microorganisms. Natural and recombinant clostripain is available. For example, natural clostripain can be prepared from *Clostridia* bacteria by cultivating the bacteria until clostripain accumulates in the nutrient medium. *Clostridia* used for producing clostripain include, for example, *Clostridium histolyticum*, especially *Clostridium histolyticum* DSM 627. Culturing is carried out anaerobically, singly or in mixed culture, for example, in non-agitated culture in the absence of oxygen or in fermenters. Where appropriate nitrogen, inert gases or other gases apart from oxygen can be introduced into the culture. The fermentation is carried out in a temperature range from about 10° to 45° C., preferably about 25° to 40° C., especially 30° to 38° C. Fermentation takes place in a pH range between 5 and 8.5, preferably between 5.5 and 8. Under these conditions, the culture broth generally shows a detectable accumulation of the enzyme after 1 to 3 days. The synthesis of clostripain starts in the late log phase and reaches its maximum in the stationary phase of growth. The production of the enzyme can be followed by means of activity assays [Mitchell W., *Meth. of Enzymol.*, 47: 165-170 (1977)].

The nutrient solution used for producing clostripain can contain 0.2 to 6%, preferably 0.5 to 3%, of organic nitrogen compounds, and inorganic salts. Suitable organic nitrogen compounds are: amino acids, peptones, also meat extracts, milled seeds, for example of corn, wheat, beans, soybean or the cotton plant, distillation residues from alcohol production, meat meals or yeast extracts. Examples of inorganic salts that the nutrient solution can contain are chlorides, carbonates, sulfates or phosphates of the alkali metals or alkaline earth metals, iron, zinc and manganese, but also ammonium salts and nitrates.

Clostripain can be purified by classical processes, for example by ammonium sulfate precipitation, ion exchange, affinity chromatography or gel permeation chromatography.

Clostripain can also be made recombinantly as described in copending patent application having attorney docket number 1627.008PRV, the disclosure of which is incorporated herein by reference.

Peptides of Interest Serving as Substrates According to the Invention

Almost any peptide can be formed by the methods of the invention. Peptides with an arginine at their C-terminus can readily be cleaved from a polypeptide containing end-to-end copies of the peptide. Peptides with one or more internal arginine residues can also be made by employing the teachings of the invention on which arginine-containing sites are favored for cleavage. Peptides having C-terminal amino acids other than arginine can be produced by placing a clostripain cleavage site within the polypeptide at the N-terminus of the peptide of interest. This latter technique produces the single copy desired peptide and employs a recombinantly expressed polypeptide having a discardable peptide sequence at the N-terminal side of the desired peptide.

Clostripain is generally perceived to be an "arginine" or an "arginine/lysine" protease, meaning that clostripain cleaves polypeptides on the carboxyl side of arginine and/or lysine amino acid residues. However, according to the invention, clostripain has even greater specificity, particularly under the reaction conditions provided herein. Hence, peptides with internal lysine and arginine residues can be made by the procedures of the invention.

Moreover, the construction of the polypeptide can be manipulated so that the peptide of interest is present at the C-terminus of the polypeptide and a clostripain cleavage site is at the N-terminus of the peptide of interest. Hence, when cleavage is performed on a polypeptide containing such a C-terminal peptide, the peptide is readily released. Using such a precursor polypeptide, peptides with any C-terminal residue can be formed.

According to the invention, peptides having one or more internal arginine residues can still be selectively cleaved at their termini so that a functional, full-length peptide can be recovered. This enhanced selectivity is achieved by recognition that clostripain preferentially cleaves a polypeptide having a cleavage site as shown in Formula I, where the cleavage occurs at a peptide bond after amino acid $Xaa_2$:

$$Xaa_1\text{-}Xaa_2\text{-}Xaa_3 \qquad (I)$$

wherein
- $Xaa_1$ aspartic acid, glycine, proline or glutamic acid;
- $Xaa_2$ is arginine; and
- $Xaa_3$ is not an acidic amino acid.

Hence, a peptide of the Formula: $Xaa_3$-$Peptide_1$-$Xaa_1$-$Xaa_2$, can readily be excised from a polypeptide having end-to-end concatemers of the peptide, when $Xaa_1$, $Xaa_2$, and $Xaa_3$ are as described above. $Peptide_1$ refers to a peptidyl entity that is unique to the selected peptide of interest. Hence, $Peptide_1$ has any amino acid sequence that is selected by one of skill in the art. An example of such a polypeptide with end-to-end concatemers of the peptide of interest has Formula II:

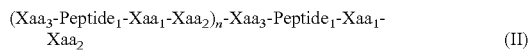

$$(Xaa_3\text{-}Peptide_1\text{-}Xaa_1\text{-}Xaa_2)_n\text{-}Xaa_3\text{-}Peptide_1\text{-}Xaa_1\text{-}Xaa_2 \qquad (II)$$

wherein
- the peptide comprises $Xaa_3$-$Peptide_1$-$Xaa_1$-$Xaa_2$;
- n is an integer ranging from 0 to 50;
- $Xaa_1$ is aspartic acid, glycine, proline or glutamic acid;
- $Xaa_2$ is arginine; and
- $Xaa_3$ is not an acidic amino acid.

However, the invention is not limited to cleavage of polypeptides having end-to-end concatemers of a peptide of interest. The invention also provides methods of making large amounts of a peptide that is present as a single copy within a polypeptide. This aspect of the invention enables the production of a single copy desired peptide having virtually any amino acid sequence and one not having an arginine at the C-terminus. That is, the invention provides methods of making large amounts of peptides of the Formula, $Xaa_3$-$Peptide_1$, which do not have a C-terminal lysine or arginine. A cleavable peptide linker can be attached onto the peptide (e.g. Linker-$Xaa_3$-$Peptide_1$) to generate an N-terminal cleavage site for generating peptides of interest that have no C-terminal arginine or lysine. The Linker has a C-terminal $Xaa_1$-$Xaa_2$ sequence that directs cleavage to the junction between the C-terminal $Xaa_2$ residue of the Linker and the $Xaa_3$ N-terminal residue of the peptide. Hence, peptides of the Formula, $Xaa_3$-$Peptide_1$, that have C-terminal acidic, aliphatic or aromatic amino acids can readily be made by the present methods.

Cleavage of a peptide of the Formula, $Xaa_3$-$Peptide_1$, from a polypeptide having at least one copy of the peptide relies upon the presence of a site that has Formula I ($Xaa_1$-$Xaa_2$-$Xaa_3$) at the junction between the peptide and the attached Linker or polypeptide. The $Xaa_3$ amino acid forms the N-terminal end of the peptide and is not an acidic amino acid. Polypeptides of Formula III can readily be cleaved by clostripain:

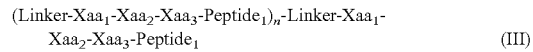

$$(\text{Linker-}Xaa_1\text{-}Xaa_2\text{-}Xaa_3\text{-}Peptide_1)_n\text{-}\text{Linker-}Xaa_1\text{-}Xaa_2\text{-}Xaa_3\text{-}Peptide_1 \qquad (III)$$

wherein
- the desired peptide comprises $Xaa_3$-$Peptide_1$
- n is an integer ranging from 0 to 50;
- $Xaa_1$ is aspartic acid, glycine, proline or glutamic acid;
- $Xaa_2$ is arginine; and
- $Xaa_3$ is not an acidic amino acid.

Cleavage of a polypeptide of Formula III yields one molar equivalent of the $Xaa_3$-$Peptide_1$ and n molar equivalents of a polypeptide of the following structure: $Xaa_3$-$Peptide_1$-Linker-$Xaa_1$-$Xaa_2$. While this polypeptide may not have a specific utility after cleavage, many "unused" parts of the linker or the polypeptide do have specific purposes. For example, the $Xaa_1$-$Xaa_2$ amino acids in the polypeptide are recognized by and direct clostripain to cleave the $Xaa_2$-$Xaa_3$ peptide bond with specificity. As described in the section entitled "Precursor polypeptides," other parts of the polypeptide or the linker have specific functions relating to the recombinant expression, translation, sub-cellular localization, etc. of the polypeptide within the host cell.

Almost any peptide of interest to one of skill in the art can be made by the methods of the invention. Peptides of interest include, for example, any glucagon-like peptide (GLP). Different types of GLPs exist, for example, the GLP-1 or GLP-2 peptides. Different types of GLP-1 and GLP-2 peptides exist as well. Types of GLPs that can be made by the methods of the invention include, for example, GLP-1(7-36) (SEQ ID NO:1), GLP-1 (7-36)amide (SEQ ID NO:2), GLP-1 (7-37) (SEQ ID NO:3), GLP-1 (7-37)amide (SEQ ID NO:4), GLP-1 (7-36) K26R (SEQ ID NO:5), GLP-1(7-36) K26R-$NH_2$ (SEQ ID NO:6), GLP-1 (7-37) K26R (SEQ ID NO:7), GLP-1(7-37) K26R-$NH_2$ (SEQ ID NO:8), GLP-2 (1-34) (SEQ ID NO:9), GLP-2 (1-34)amide (SEQ ID NO:10), GLP-2 (1-33) (SEQ ID NO:11), GLP-2 (1-33)amide (SEQ ID NO:12), GLP-2 (1-33) A2G (SEQ ID NO:13), GLP-2 (1-33) A2G amide (SEQ ID NO:14), GLP-2 (1-34)A2G (SEQ ID NO:15), GLP-2 (1-34) A2G amide (SEQ ID NO:16), and the like. The sequences of such GLPs are provided in Table 1 along with their names and SEQ ID NO: ("NO:").

TABLE 1

| Name | Sequence | NO: |
|---|---|---|
| GLP-1(7-36) | HAEGTFTSDVSSYLEGQAAKEFIAWLVKGR | 1 |
| GLP-1(7-36)NH$_2$ | HAEGTFTSDVSSYLEGQAAKEFIAWLVKGR-NH$_2$ | 2 |
| GLP-1(7-37) | HAEGTFTSDVSSYLEGQAAKEFIAWLVKGRG | 3 |
| GLP-1(7-37)NH$_2$ | HAEGTFTSDVSSYLEGQAAKEFIAWLVKGRG-NH$_2$ | 4 |
| GLP-1(7-36) K26R | HAEGTFTSDVSSYLEGQAAREFIAWLVKGR | 5 |
| GLP-1(7-36) K26R-NH$_2$ | HAEGTFTSDVSSYLEGQAAREFIAWLVKGR-NH$_2$ | 6 |
| GLP-1(7-37) K26R | HAEGTFTSDVSSYLEGQAAREFIAWLVKGRG | 7 |
| GLP-1(7-37) K26R-NH$_2$ | HAEGTFTSDVSSYLEGQAAREFIAWLVKGRG-NH$_2$ | 8 |
| GLP-2(1-34) | HADGSFSDGMNTILDNLAARDFINWLIQTKITDR | 9 |
| GLP-2(1-34)-NH$_2$ | HADGSFSDGMNTILDNLAARDFINWLIQTKITDR-NH$_2$ | 10 |
| GLP-2(1-33) | HADGSFSDGMNTILDNLAARDFINWLIQTKITD | 11 |
| GLP-2(1-33)-NH$_2$ | HADGSFSDGMNTILDNLAARDFINWLIQTKITD)-NH$_2$ | 12 |
| GLP-2(1-33)A2G | HGDGSFSDGMNTILDNLAARDFINWLIQTKITD | 13 |
| GLP-2(1-33)A2G-NH$_2$ | HGDGSFSDGMNTILDNLAARDFINWLIQTKITD-NH$_2$ | 14 |
| GLP-2(1-34)A2G | HGDGSFSDGMNTILDNLAARDFINWLIQTKITDR | 15 |
| GLP-2(1-34)A2G-NH$_2$ | HGDGSFSDGMNTILDNLAARDFINWLIQTKITDR-NH$_2$ | 16 |

The peptide GLP-1 (7-36) (SEQ ID NO:1) is numbered 7-36 for historical reasons. The original sequencing studies indicated that GLP-1 was the product of a gene that encoded thirty-seven amino acids. However, it was subsequently found that the active peptide did not have residues 1-6, and that the glycine at position 37 was degraded to form an amide at position 36.

The invention also contemplates peptide variants derivatives of the GLP peptides described herein. Derivative and variant peptides of the invention are derived from the reference peptide by deletion or addition of one or more amino acids to the N-terminal and/or C-terminal end; deletion or addition of one or more amino acids at one or more sites within the peptide; or substitution of one or more amino acids at one or more sites within the peptide. Thus, the peptides of the invention may be altered in various ways including amino acid substitutions, deletions, truncations, and insertions.

Such variant and derivative polypeptides may result, for example, from human manipulation. Methods for such manipulations are generally known in the art. For example, amino acid sequence variants of the polypeptides can be prepared by mutations in the DNA. Methods for mutagenesis and nucleotide sequence alterations are well known in the art. [See, for example, Kunkel, *Proc. Natl. Acad. Sci. USA*, 82: 488 (1985); Kunkel et al., *Methods in Enzymol.*, 154: 367 (1987); U.S. Pat. No. 4,873,192; Walker and Gaastra, eds., Techniques in Molecular Biology, MacMillan Publishing Company, New York (1983) and the references cited therein.] Guidance as to appropriate amino acid substitutions that do not affect biological activity of the protein of interest may be found in the model of Dayhoff et al., Atlas of Protein Sequence and Structure, Natl. Biomed. Res. Found., Washington, C.D. (1978), herein incorporated by reference.

Precursor Polypeptides

Any precursor polypeptide containing one or more copies of a peptide of interest (desired peptide) and a Formula I sequence at one or both ends of that peptide can be utilized as a substrate for the clostripain cleavage methods of the invention. One of skill in the art can readily design many such precursor polypeptides. While the peptide of interest may form a substantial portion of the precursor polypeptide, the polypeptide may also have additional peptide segments unrelated to the peptide sequence of interest. Additional peptide segments can provide any function desired by one of skill in the art.

One example of an additional peptide segment that can be present in the precursor polypeptide is a "Tag" that provides greater levels of precursor polypeptide production in cells. Numerous tag sequences are known in the art. In the present invention, bacterial tag sequences are preferred. Such tag sequences may be obtained from gene 108 bacteriophage T7 and the gene encoding ompT. In one embodiment, a T7tag is used that has the amino acid sequence, ASMTGGQQMGR (SEQ ID NO:17), or MASMTGGQQMGR (SEQ ID NO:18).

The precursor polypeptide can also encode an "inclusion body leader partner" that is operably linked to the peptide of interest. Such an inclusion body leader partner may be linked to the amino-terminus, the carboxyl-terminus or both termini of a precursor polypeptide. In one example, the inclusion body leader partner has an amino acid sequence corresponding to: GSGQGQAQYLSASCVVFTNYSGDTASQVD (SEQ ID NO:19). In another embodiment, the inclusion body leader partner is a part of the *Drosophila* vestigial polypeptide ("Vg"), having sequence GSGQGQAQYLAASLVVF TNYSGDTASQ VDVNGPRAMVD (SEQ ID NO:20). In another embodiment, the inclusion body leader partner is a part of polyhedrin polypeptide ("Ph"), having sequence GSAEEEEILLEVSLVFKVKEFAPDAPLFTGPAYVD (SEQ ID NO:21). Other inclusion body leader partners that can be used include a part of the lactamase polypeptide, having sequence SIQHFRVALIPFFAAFSLPVFA (SEQ ID NO:22). Upon expression of the polypeptide, an attached inclusion body leader partner causes the polypeptide to form inclusion bodies within the bacterial host cell. Other inclusion body leader partners can be identified, for example, by linking a test inclusion body leader partner to a polypeptide construct. The resulting inclusion body leader partner-polypeptide construct then would be tested to determine whether it will form an inclusion body within a cell.

The amino acid sequence of an inclusion body leader partner can be altered to produce inclusion bodies that facilitate isolation of inclusion bodies that are formed, thereby allowing an attached polypeptide to be purified more easily. For example, the inclusion body leader partner may be altered to produce inclusion bodies that are more or less soluble under a certain set of conditions. Those of skill in the art realize that solubility is dependent on a number of variables that include, but are not limited to, pH, temperature, salt concentration, protein concentration and the hydrophilicity or hydrophobicity of the amino acids in the protein. Thus, an inclusion body leader partner of the invention may be altered to produce an inclusion body having desired solubility under differing conditions.

An inclusion body leader partner may also be altered to produce inclusion bodies that contain polypeptide constructs having greater or lesser self-association. Self-association refers to the strength of the interaction between two or more polypeptides that form an inclusion body. Such self-association may be determined though use of a variety of known methods used to measure protein-protein interactions. Such methods are known in the art and have been described. Freifelder, Physical Biochemistry: Applications to Biochemistry and Molecular Biology, W.H. Freeman and Co., 2nd edition, New York, N.Y. (1982).

Self-adhesion can be used to produce inclusion bodies that exhibit varying stability to purification. For example, greater self-adhesion may be desirable to stabilize inclusion bodies against dissociation in instances where harsh conditions are used to isolate the inclusion bodies from a cell. Such conditions may be encountered if inclusion bodies are being isolated from cells having thick cell walls. However, where mild conditions are used to isolate the inclusion bodies, less self-adhesion may be desirable as it may allow the polypeptide constructs composing the inclusion body to be more readily solubilized or processed. Accordingly, an inclusion body leader partner of the invention may be altered to provide a desired level of self-adhesion for a given set of conditions.

The precursor polypeptide can also encode one or more "cleavable peptide linkers" that can flank one or more copies of the peptide of interest. Such a cleavable peptide linker provides a convenient clostripain cleavage site adjacent to a peptide of interest, and allows a peptide that does not naturally begin or end with an arginine or lysine to be excised with clostripain. Convenient cleavable peptide linkers include short peptidyl sequences having a C-terminal $Xaa_1$-$Xaa_2$ sequence, for example, a Linker-$Xaa_1$-$Xaa_2$ sequence, wherein $Xaa_1$ is aspartic acid, glycine, proline or glutamic acid, and $Xaa_2$ is arginine. The $Xaa_1$-$Xaa_2$ sequence directs cleavage to the junction between the C-terminal $Xaa_2$ residue of the linker and a $Xaa_3$ residue on the N-terminus of the peptide.

A cleavable peptide linker can have the following Formula IV:

$$(Peptide_5)_m\text{-}Xaa_1\text{-}Xaa_2 \quad\quad\quad IV$$

wherein:
n and m are separately an integer ranging from 0 to 50;
$Xaa_1$ is aspartic acid, glycine, proline or glutamic acid; and
$Xaa_2$ is arginine; and
$Peptide_5$ is any single or multiple amino acid residue including but not limited to an inclusion body leader partner.

In some embodiments, use of proline as $Peptide_5$ is preferred.

Many cleavable peptide linker sequences can readily be developed and used by one of skill in the art. A few examples of convenient cleavable peptide linker sequences are provided below.

```
Ala-Phe-Leu-Gly-Pro-Gly-Asp-Arg    (SEQ ID NO:23)

Val-Asp-Arg                         (SEQ ID NO:24)

Gly-Ser-Asp-Arg                     (SEQ ID NO:25)

Ile-Thr-Asp-Arg                     (SEQ ID NO:26)

Pro-Gly-Asp-Arg.                    (SEQ ID NO:27)
```

Other amino acids, peptides, or polypeptides selected by one of skill in the art can also be included in the precursor polypeptide.

GLP-1 Polypeptides

In another embodiment of the invention, the polypeptide can encode one or more copies of GLP-1. An example of a polypeptide encoding one copy of GLP-1 is a polypeptide having the following generalized structure:

$$\text{Tag-Linker-[GLP-1(7-36)-Linker}_2]_q \quad\quad\quad VII$$

wherein Linker is as described above. Preferably, Linker is $Linker_1$, defined herein as $Peptide_5$-Asp-Arg. The variable q is an integer of about 2 to about 20. A preferred value for q in this case is 3. As provided above, the nucleic acid encoding the $Peptide_5$ amino acids can provide convenient restriction sites for cloning purposes so long as an amino acid codon (rather than, for example, a stop codon) is still encoded by the nucleic acid. While any appropriate sequence can be used for $Peptide_5$, a preferred sequence is Ile-Thr.

$Linker_2$ is a cleavable peptide linker having the sequence AFLGPGDR (SEQ ID NO:23). A multi-copy GLP-1(7-36) (SEQ ID NO: 1) polypeptide of this generalized structure with q equal to 3 has the following sequence:

```
                                        (SEQ ID NO:31)
MASMTGGQQMGRGS-Peptide5-Asp-Arg-

HAEGTFTSDVSSYLEGQAAKEFIAWLVKGR-AFLGPGDR

HAEGTFTSDVSSYLEGQAAKEFIAWLVKGR-AFLGPGDR

HAEGTFTSDVSSYLEGQAAKEFIAWLVKGR
```

One mutation that can be made is a substitution of arginine for lysine at position 26 of the GLP-1 peptide, to produce GLP-1(7-36, K26R) having SEQ ID NO:5 or GLP-1(7-37, K26R) having SEQ ID NO:7. This amino acid substitution of arginine for lysine produces a GLP-1 peptide with just one lysine at position 34. In some embodiments, one of skill in the art may chose to derivatize the lysine at position 34, in which case having an arginine at position 26 eliminates the potential for derivatization at two sites.

GLP-2 Polypeptides

In one embodiment of the invention, the polypeptide can encode one or more copies of GLP-2.

Examples of multi-copy GLP-2 polypeptides include polypeptides having the following generalized structures:

Tag-Linker-[GLP-2(1-34)]$_q$     VI

Where GLP-2 (1-34) has SEQ ID NO:9 and q is an integer of about 2 to about 20. A preferred value for q is about 6. The Linker is preferably Peptide$_5$-Asp-Arg or Peptide$_5$-Asp-Arg-Arg. Tag is a translation initiation sequence, for example, SEQ ID NO:17 or 18. A multi-copy GLP-2 polypeptide of this generalized structure with q equal to 6 and with Linker as Peptide$_5$-Asp-Arg (GSDR) has the following sequence:

```
                                          (SEQ ID NO:29)
MASMTGGQQMGR-GSDR-

HADGSFSDGMNTILDNLAARDFINWLIQTKITDR-

HADGSFSDGMNTILDNLAARDFINWLIQTKITDR-

HADGSFSDGMNTILDNLAARDFINWLIQTKITDR-

HADGSFSDGMNTILDNLAARDFINWLIQTKITDR-

HADGSFSDGMNTILDNLAARDFINWLIQTKITDR-

HADGSFSDGMNTILDNLAARDFINWLIQTKITDR.
```

No cleavable peptide linkers are needed between the GLP-2 six peptides present within this precursor polypeptide because GLP-2(1-34) has an Asp-Arg sequence at it C-terminus.

One of skill in the art can modify or mutate these GLP-2 polypeptide sequences as desired so long as the aspartic acid at position 21 of GLP-2 (HADGSFSDGMNTILDN LAARDFINWLIQTKITDR, SEQ ID NO:9) is not changed when arginine is present at position 20. This aspartic acid is on the C-terminal side of an arginine and is therefore at position Xaa$_3$ in the clostripain cleavage site. As described, Xaa$_3$ should not be an acidic amino acid when clostripain cleavage is desired. However, in the GLP-2 polypeptides described above, an acidic amino acid at position 21 (Asp-21) that protects against cleavage at the internal arginine. Recognition that Asp-21 protects against cleavage allows a full-length GLP-2 peptide to be produced in far larger amounts than a GLP-2 fragment containing only amino acids 1-19.

One mutation that can be made is a substitution of glycine for alanine at position 2 of the GLP-2 peptide, to produce GLP-2(1-33, A2G) having SEQ ID NO:13 or GLP-2(1-34, A2G) having SEQ ID NO:15. This amino acid substitution of glycine for alanine produces a GLP-2 peptide which has a very reduced cleavage rate by a eukaryotic endopeptidase that might degrade the peptide upon administration to a mammal. Hence, the GLP-2(1-33, A2G) peptide can have a longer half-life in vivo than the GLP-2(1-33) peptide.

Amidation Conditions

When clipped from a multicopy polypeptide under normal hydrolysis conditions, the recombinant peptide has a C terminal carboxyl group. However, an amidated C-terminus is preferred for use in mammals. Clostripain can be used to amidate the C-terminal residue to make an amidated recombinant peptide. According to that process, ammonia is included in the clostripain cleavage medium. The ammonia is added to the inchoate C-terminus by the clostripain to form the C-terminus amide. Addition of an amino acid to the C-terminus can also be accomplished by substitution of the amino acid for ammonia in such a clostripain cleavage.

Clostripain, like other proteases, will perform transpeptidation reactions in the presence of a nucleophile other than water. Ammonia or other amines can be used as the nucleophile. A polypeptide having an arginine residue can be used as the substrate. The polypeptide may have a leader sequence as well. Transpeptidation will occur at the C-terminal of the arginine.

Adjustment of the conditions to increase the amount of amide formation will produce a high yield of the amide. However, the recombinant peptide amide itself becomes a substrate for hydrolysis as it is formed. To solve this problem, a tangential flow filtration in combination with the enzyme reaction is used. Clostripain simultaneously cleaves multicopy peptide constructs and amidates the C-terminal residue of the single copy cleaved peptide. Use of tangential flow filtration during the enzymatic reaction to remove the amidated peptide produces that peptide in high yield.

For example, use of a 10K diafiltration/tangential flow filtration membrane will enhance the reaction yield. Undigested peptide construct and clostripain are retained on the retentate side of the membrane. The single copy cleaved rGLP-1 passes through the membrane. Continued exposure of rGLP-1 amide to clostripain will result in loss of the amide to OH. Continual removal of amide through the membrane will reduce this unwanted side reaction. Smaller pore sized membranes were not as efficient at removing the newly formed rGLP-1 amide during the reaction time course.

Reaction conditions will enhance the transpeptidation reaction relative to hydrolysis for this particular polypeptide construct. Urea in the clostripain reaction maintains peptide solubility and minimizes membrane fouling. The clostripain digestion/amidation reaction will tolerate higher urea concentrations. The amount of clostripain can be varied to shorten or lengthen the overall reaction time. Fresh buffer can be added to maintain constant volume or after volume reduction.

Production of Precursor polypeptides

A) DNA Constructs and Expression Cassettes

Precursor polypeptides are produced in any convenient manner, for example, by using a recombinant nucleic acid that encodes the desired precursor polypeptide. Nucleic acids encoding the precursor polypeptides of the invention can be inserted into convenient vectors for transformation of an appropriate host cell. Those of skill in the art can readily obtain and clone nucleic acids encoding a selected precursor polypeptide into a variety of commercially available plasmids. One example of a useful plasmid vector is the pET series of plasmids (Stratagene, La Jolla, Calif.). After insertion of the selected nucleic acid into an appropriate vector, the vector can be introduced into a host cell, preferably a bacterial host cell.

Nucleic acid constructs and expression cassettes can be created through use of recombinant methods that are available in the art. [Sambrook and Russell, Molecular Cloning: A Laboratory Manual, 3rd edition (Jan. 15, 2001) Cold Spring Harbor Laboratory Press, ISBN: 0879695765; Ausubel et al., *Current Protocols in Molecular Biology*, Green Publishing Associates and Wiley Interscience, NY (1989)]. Generally, recombinant methods involve preparation of a desired DNA fragment and ligation of that DNA fragment into a preselected position in another DNA vector, such as a plasmid.

In a typical example, a desired DNA fragment is first obtained by synthesizing and/or digesting a DNA that contains the desired DNA fragment with one or more restriction enzymes that cut on both sides of the desired DNA fragment. The restriction enzymes may leave a "blunt" end or a "sticky" end. A "blunt" end means that the end of a DNA fragment does not contain a region of single-stranded DNA. A DNA fragment having a "sticky" end means that the end of the DNA fragment has a region of single-stranded DNA. The sticky end may have a 5' or a 3' overhang. Numerous restriction enzymes are commercially available and conditions for their use are also well known. (USB, Cleveland, Ohio; New England Biolabs, Beverly, Mass.).

The digested DNA fragments may be extracted according to known methods, such as phenol/chloroform extraction, to produce DNA fragments free from restriction enzymes. The restriction enzymes may also be inactivated with heat or other suitable means. Alternatively, a desired DNA fragment may be isolated away from additional nucleic acid sequences and restriction enzymes through use of electrophoresis, such as agarose gel or polyacrylamide gel electrophoresis. Generally, agarose gel electrophoresis is used to isolate large nucleic acid fragments while polyacrylamide gel electrophoresis is used to isolate small nucleic acid fragments. Such methods are used routinely to isolate DNA fragments. The electrophoresed DNA fragment can then be extracted from the gel following electrophoresis through use of many known methods, such as electroelution, column chromatography, or binding of glass beads. Many kits containing materials and methods for extraction and isolation of DNA fragments are commercially available. (Qiagen, Venlo, Netherlands; Qbiogene, Carlsbad, Calif.).

The DNA segment into which the fragment is going to be inserted is then digested with one or more restriction enzymes. Preferably, the DNA segment is digested with the same restriction enzymes used to produce the desired DNA fragment. This will allow for directional insertion of the DNA fragment into the DNA segment based on the orientation of the complimentary ends. For example, if a DNA fragment is produced that has an EcoRI site on its 5' end and a BamHI site at the 3' end, it may be directionally inserted into a DNA segment that has been digested with EcoRI and BamHI based on the complementarity of the ends of the respective DNAs. Alternatively, blunt ended cloning may be used if no convenient restriction sites exist that allow for directional cloning. For example, the restriction enzyme BsaAI leaves DNA ends that do not have a 5' or 3' overhang. Blunt ended cloning may be used to insert a DNA fragment into a DNA segment that was also digested with an enzyme that produces a blunt end. Additionally, DNA fragments and segments may be digested with a restriction enzyme that produces an overhang and then treated with an appropriate enzyme to produce a blunt end. Such enzymes include polymerases and exonucleases. Those of skill in the art know how to use such methods alone or in combination to selectively produce DNA fragments and segments that may be selectively combined.

A DNA fragment and a DNA segment can be combined though conducting a ligation reaction. Ligation links two pieces of DNA through formation of a phosphodiester bond between the two pieces of DNA. Generally, ligation of two or more pieces of DNA occurs through the action of the enzyme ligase when the pieces of DNA are incubated with ligase under appropriate conditions. Ligase and methods and conditions for its use are well known in the art and are commercially available.

The ligation reaction or a portion thereof is then used to transform cells to amplify the recombinant DNA formed, such as a plasmid having an insert. Methods for introducing DNA into cells are well known and are disclosed herein.

Those of skill in the art recognize that many techniques for producing recombinant nucleic acids can be used to produce an expression cassette or nucleic acid construct of the invention.

B) Promoters

The expression cassette of the invention includes a promoter. Any promoter able to direct transcription of the expression cassette may be used. Accordingly, many promoters may be included within the expression cassette of the invention. Some useful promoters include, constitutive promoters, inducible promoters, regulated promoters, cell specific promoters, viral promoters, and synthetic promoters. A promoter is a nucleotide sequence which controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell.

Examples of Promoters Useful in Bacteria

For expression of a leader protein in a bacterium, an expression cassette having a bacterial promoter will be used. A bacterial promoter is any DNA sequence capable of binding bacterial RNA polymerase and initiating the downstream (3") transcription of a coding sequence into mRNA. A promoter will have a transcription initiation region which is usually placed proximal to the 5' end of the coding sequence. This transcription initiation region usually includes an RNA polymerase binding site and a transcription initiation site. A second domain called an operator may be present and overlap an adjacent RNA polymerase binding site at which RNA synthesis begins. The operator permits negatively regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* [Raibaud et al., *Ann. Rev. Genet.*, 18:173 (1984)]. Regulated expression may therefore be positive or negative, thereby either enhancing or reducing transcription. A preferred promoter is the YX *Chlorella* virus promoter. [U.S. Pat. No. 6,316,224].

Sequences encoding metabolic pathway enzymes provide particularly useful promoter sequences. Examples include promoter sequences derived from sugar metabolizing enzymes, such as galactose, lactose (lac) (Chang et al., *Nature*, 198:1056 (1977)], and maltose. Additional examples include promoter sequences derived from biosynthetic enzymes such as tryptophan (trp) [Goeddel et al., *Nuc. Acids Res.*, 8:4057 (1980); Yelverton et al., *Nuc. Acids Res.*, 9:731 (1981); U.S. Pat. No. 4,738,921; and EPO Publ. Nos. 036 776 and 121 775]. The ∃-lactamase (bla) promoter system [Weissmann, "The cloning of interferon and other mistakes", in: Interferon 3 (ed. I. Gresser), 1981], and bacteriophage lambda $P_L$ [Shimatake et al., *Nature*, 292:128 (1981)] and T5 (U.S. Pat. No. 4,689,406) promoter systems also provide useful promoter sequences.

Synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al., *Gene*, 25:167 (1983); de Boer et al., *Proc. Natl. Acad. Sci. USA*, 80:21 (1983)]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., *J. Mol. Biol.*, 189:113 (1986); Tabor et al., *Proc. Natl. Acad. Sci. USA*, 82:1074 (1985)]. In addition, a hybrid promoter can also be comprised of a bacteriophage promoter and an *E. coli* operator region [EPO Publ. No. 267 851].

Examples of Promoters Useful in Insect Cells

An expression cassette having a baculovirus promoter can be used for expression of a leader protein in an insect cell. A baculovirus promoter is any DNA sequence capable of binding a baculovirus RNA polymerase and initiating transcription of a coding sequence into mRNA. A promoter will have a transcription initiation region which is usually placed proximal to the 5' end of the coding sequence. This transcription initiation region usually includes an RNA polymerase binding site and a transcription initiation site. A second domain called an enhancer may be present and is usually distal to the structural gene. A baculovirus promoter may be a regulated promoter or a constitutive promoter. Useful promoter sequences may be obtained from structural genes that are transcribed at times late in a viral infection cycle. Examples include sequences derived from the gene encoding the baculoviral polyhedron protein [Friesen et al., "The Regulation of Baculovirus Gene Expression", in: The Molecular Biology of Baculoviruses (ed. Walter Doerfler), 1986; and EPO Publ. Nos. 127 839 and 155 476] and the gene encoding the baculoviral p10 protein [Vlak et al., *J. Gen. Virol.*, 69:765 (1988)].

Examples of Promoters Useful in Yeast

Promoters that are functional in yeast are known to those of ordinary skill in the art. In addition to an RNA polymerase binding site and a transcription initiation site, a yeast promoter may also have a second region called an upstream activator sequence. The upstream activator sequence permits regulated expression that may be induced. Constitutive expression occurs in the absence of an upstream activator sequence. Regulated expression may be either positive or negative, thereby either enhancing or reducing transcription.

Promoters for use in yeast may be obtained from yeast genes that encode enzymes active in metabolic pathways. Examples of such genes include alcohol dehydrogenase (ADH) (EPO Publ. No. 284 044), enolase, glucokinase, glucose-6-phosphate isomerase, glyceraldehyde-3-phosphatedehydrogenase (GAP or GAPDH), hexokinase, phosphofructokinase, 3-phosphoglyceratemutase, and pyruvate kinase (PyK). [EPO Publ. No. 329 203]. The yeast PHO5 gene, encoding acid phosphatase, also provides useful promoter sequences. [Myanohara et al., *Proc. Natl. Acad. Sci. USA*, 80:1 (1983)].

Synthetic promoters which do not occur in nature may also be used for expression in yeast. For example, upstream activator sequences from one yeast promoter may be joined with the transcription activation region of another yeast promoter, creating a synthetic hybrid promoter. Examples of such hybrid promoters include the ADH regulatory sequence linked to the GAP transcription activation region [U.S. Pat. Nos. 4,876,197 and 4,880,734]. Other examples of hybrid promoters include promoters which consist of the regulatory sequences of either the ADH2, GAL4, GAL10, or PHO5 genes, combined with the transcriptional activation region of a glycolytic enzyme gene such as GAP or PyK [EPO Publ. No. 164 556]. Furthermore, a yeast promoter can include naturally occurring promoters of non-yeast origin that have the ability to bind yeast RNA polymerase and initiate transcription. Examples of such promoters are known in the art. [Cohen et al., *Proc. Natl. Acad. Sci. USA*, 77:1078 (1980); Henikoff et al., *Nature*, 283:835 (1981); Hollenberg et al., *Curr. Topics Microbiol. Immunol.*, 96:119 (1981); Hollenberg et al., "The Expression of Bacterial Antibiotic Resistance Genes in the Yeast *Saccharomyces cerevisiae*", in: Plasmids of Medical, Environmental and Commercial Importance (eds. K. N. Timmis and A. Puhler), 1979; Mercerau-Puigalon et al., *Gene*, 11:163 (1980); Panthier et al., *Curr. Genet.*, 2:109 (1980)].

Examples of Promoters Useful in Mammalian Cells

Many mammalian promoters are known in the art that may be used in conjunction with the expression cassette of the invention. Mammalian promoters often have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter may also contain an upstream promoter element, usually located within 100 to 200 bp upstream of the TATA box. An upstream promoter element determines the rate at which transcription is initiated and can act in either orientation [Sambrook et al., "Expression of Cloned Genes in Mammalian Cells", in: Molecular Cloning: A Laboratory Manual, 2nd ed., 1989].

Mammalian viral genes are often highly expressed and have a broad host range; therefore sequences encoding mammalian viral genes often provide useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallothioneih gene, also provide useful promoter sequences. Expression may be either constitutive or regulated.

A mammalian promoter may also be associated with an enhancer. The presence of an enhancer will usually increase transcription from an associated promoter. An enhancer is a regulatory DNA sequence that can stimulate transcription up to 1000-fold when linked to homologous or heterologous promoters, with synthesis beginning at the normal RNA start site. Enhancers are active when they are placed upstream or downstream from the transcription initiation site, in either normal or flipped orientation, or at a distance of more than 1000 nucleotides from the promoter. [Maniatis et al., *Science*, 236:1237 (1987); Alberts et al., Molecular Biology of the Cell, 2nd ed., 1989]. Enhancer elements derived from viruses are often times useful, because they usually have a broad host range. Examples include the SV40 early gene enhancer [Dijkema et al., *EMBO J.*, 4:761 (1985)] and the enhancer/promoters derived from the long terminal repeat (LTR) of the Rous Sarcoma Virus [Gorman et al., *Proc. Natl. Acad. Sci. USA*, 79:6777 (1982b)] and from human cytomegalovirus [Boshart et al., *Cell*, 41:521 (1985)]. Additionally, some enhancers are regulatable and become active only in the presence of an inducer, such as a hormone or metal ion [Sassone-Corsi and Borelli, *Trends Genet.*, 2:215 (1986); Maniatis et al., *Science*, 236:1237 (1987)].

It is understood that many promoters and associated regulatory elements may be used within the expression cassette of the invention to transcribe an encoded leader protein. The promoters described above are provided merely as examples and are not to be considered as a complete list of promoters that are included within the scope of the invention.

C Translation Initiation Sequence

The expression cassette of the invention may contain a nucleic acid sequence for increasing the translation efficiency of an mRNA encoding a leader protein of the invention. Such increased translation serves to increase production of the leader protein. The presence of an efficient ribosome binding site is useful for gene expression in prokaryotes. In bacterial mRNA a conserved stretch of six nucleotides, the Shine-Dalgarno sequence, is usually found upstream of the initiating AUG codon. [Shine et al., Nature, 254:34 (1975)]. This sequence is thought to promote ribosome binding to the mRNA by base pairing between the ribosome binding site and the 3' end of Escherichia coli 16S rRNA. [Steitz et al., "Genetic signals and nucleotide sequences in messenger RNA", in: Biological Regulation and Development: Gene Expression (ed. R. F. Goldberger), 1979)]. Such a ribosome binding site, or operable derivatives thereof, are included within the expression cassette of the invention.

A translation initiation sequence can be derived from any expressed Escherichia coli gene and can be used within an expression cassette of the invention. Preferably the gene is a highly expressed gene. A translation initiation sequence can be obtained via standard recombinant methods, synthetic techniques, purification techniques, or combinations thereof, which are all well known. [Ausubel et al., Current Protocols in Molecular Biology, Green Publishing Associates and Wiley Interscience, NY. (1989); Beaucage and Caruthers, Tetra. Letts., 22:1859 (1981); VanDevanter et al., Nucleic Acids Res., 12:6159 (1984)]. Alternatively, translational start sequences can be obtained from numerous commercial vendors. (Operon Technologies; Life Technologies Inc, Gaithersburg, Md.). In a preferred embodiment, the T7tag leader sequence is used. The T7tag leader sequence is derived from the highly expressed T7 Gene 10 cistron. Other examples of translation initiation sequences include, but are not limited to, the maltose-binding protein (Mal E gene) start sequence [Guan et al., Gene, 67:21 (1997)] present in the pMalc2 expression vector (New England Biolabs, Beverly, Mass.) and the translation initiation sequence for the following genes: thioredoxin gene (Novagen, Madison, Wis.), Glutathione-S-transferase gene (Pharmacia, Piscataway, N.J.), β-galactosidase gene, chloramphenicol acetyltransferase gene and E. Coli Trp E gene [Ausubel et al., 1989, Current Protocols in Molecular Biology, Chapter 16, Green Publishing Associates and Wiley Interscience, NY].

Eucaryotic mRNA does not contain a Shine-Dalgarno sequence. Instead, the selection of the translational start codon is usually determined by its proximity to the cap at the 5' end of an mRNA. The nucleotides immediately surrounding the start codon in eucaryotic mRNA influence the efficiency of translation. Accordingly, one skilled in the art can determine what nucleic acid sequences will increase translation of a leader protein encoded by the expression cassette of the invention. Such nucleic acid sequences are within the scope of the invention.

D) Vectors

Vectors that may be used include, but are not limited to, those able to be replicated in prokaryotes and eukaryotes. Vectors include, for example, plasmids, phagemids, bacteriophages, viruses, cosmids, and F-factors. The invention includes any vector into which the expression cassette of the invention may be inserted and replicated in vitro or in vivo. Specific vectors may be used for specific cells types. Additionally, shuttle vectors may be used for cloning and replication in more than one cell type. Such shuttle vectors are known in the art. The nucleic acid constructs may be carried extrachromosomally within a host cell or may be integrated into a host cell chromosome. Numerous examples of vectors are known in the art and are commercially available. (Sambrook and Russell, Molecular Cloning: A Laboratory Manual, 3rd edition (Jan. 15, 2001) Cold Spring Harbor Laboratory Press, ISBN: 0879695765; New England Biolabs, Beverly, Mass.; Stratagene, La Jolla, Calif.; Promega, Madison, Wis.; ATCC, Rockville, Md.; CLON-TECH, Palo Alto, Calif.; Invitrogen, Carlsbad, Calif.; Origene, Rockville, Md.; Sigma, St. Louis, Mo.; Pharmacia, Peapack, N.J.; USB, Cleveland, Ohio). These vectors also provide many promoters and other regulatory elements that those of skill in the art may include within the nucleic acid constructs of the invention through use of known recombinant techniques.

Examples of Vectors Useful in Bacteria

A nucleic acid construct for use in a prokaryote host, such as bacteria, will preferably include a replication system allowing it to be maintained in the host for expression or for cloning and amplification. In addition, a nucleic acid construct may be present in the cell in either high or low copy number. Generally, about 5 to about 200, and usually about 10 to about 150 copies of a high copy number nucleic acid construct will be present within a host cell. A host containing a high copy number plasmid will preferably contain at least about 10, and more preferably at least about 20 plasmids. Generally, about 1 to 10, and usually about 1 to 4 copies of a low copy number nucleic acid construct will be present in a host cell. The copy number of a nucleic acid construct may be controlled by selection of different origins of replication according to methods known in the art. Sambrook and Russell, Molecular Cloning: A Laboratory Manual, 3rd edition (Jan. 15, 2001) Cold Spring Harbor Laboratory Press, ISBN: 0879695765.

A nucleic acid construct containing an expression cassette can be integrated into the genome of a bacterial host cell through use of an integrating vector. Integrating vectors usually contain at least one sequence that is homologous to the bacterial chromosome that allows the vector to integrate. Integrations are thought to result from recombinations between homologous DNA in the vector and the bacterial chromosome. For example, integrating vectors constructed with DNA from various Bacillus strains integrate into the Bacillus chromosome [EPO Publ. No. 127 328]. Integrating vectors may also contain bacteriophage or transposon sequences.

Extrachromosomal and integrating nucleic acid constructs may contain selectable markers to allow for the selection of bacterial strains that have been transformed. Selectable markers can be expressed in the bacterial host and may include genes that render bacteria resistant to drugs such as ampicillin, chloramphenicol, erythromycin, kanamycin (neomycin), and tetracycline [Davies et al., Ann. Rev. Microbiol., 32: 469, (1978)]. Selectable markers may also include biosynthetic genes, such as those in the histidine, tryptophan, and leucine biosynthetic pathways.

Numerous vectors, either extra-chromosomal or integrating vectors, have been developed for transformation into many bacteria. For example, vectors have been developed for the following bacteria: B. subtilis [Palva et al., Proc. Natl. Acad. Sci. USA, 79: 5582, (1982); EPO Publ. Nos. 036 259 and 063 953; PCT Publ. No. WO 84/04541], E. coli [Shimatake et al., Nature, 292: 128, (1981); Amann et al., Gene, 40: 183, (1985); Studier et al., J. Mol. Biol., 189: 113, (1986); EPO Publ. Nos. 036 776, 136 829 and 136 907], Streptococcus cremoris [Powell et al., Appl. Environ. Microbiol., 54: 655, (1988)]; Streptococcus lividans [Powell et al., Appl. Environ. Microbiol., 54: 655, (1988)], and Streptomyces lividans [U.S. Pat. No. 4,745,056]. Numerous vectors are also commercially available (New England Biolabs, Beverly, Mass.; Stratagene, La Jolla, Calif.).

Examples of Vectors Useful in Yeast

Many vectors may be used to construct a nucleic acid construct that contains an expression cassette of the invention and that provides for the expression of a leader protein in yeast. Such vectors include, but are not limited to, plasmids and yeast artificial chromosomes. Preferably the vector has two replication systems, thus allowing it to be maintained, for example, in yeast for expression and in a prokaryotic host for cloning and amplification. Examples of such yeast-bacteria shuttle vectors include YEp24 [Botstein, et al., *Gene*, 8:17 (1979)], pCl/l [Brake et al., *Proc. Natl. Acad. Sci. USA*, 81:4642 (1984)], and YRp17 [Stinchcomb et al., *J. Mol. Biol.*, 158:157 (1982)]. A vector may be maintained within a host cell in either high or low copy number. For example, a high copy number plasmid will generally have a copy number ranging from about 5 to about 200, and usually about 10 to about 150. A host containing a high copy number plasmid will preferably have at least about 10, and more preferably at least about 20. Either a high or low copy number vector may be selected, depending upon the effect of the vector and the leader protein on the host. [Brake et al., *Proc. Natl. Acad. Sci. USA*, 81:4642 (1984)].

A nucleic acid construct may also be integrated into the yeast genome with an integrating vector. Integrating vectors usually contain at least one sequence homologous to a yeast chromosome that allows the vector to integrate, and preferably contain two homologous sequences flanking an expression cassette of the invention. Integrations appear to result from recombinations between homologous DNA in the vector and the yeast chromosome. [Orr-Weaver et al., *Methods in Enzymol.*, 101:228 (1983)]. An integrating vector may be directed to a specific locus in yeast by selecting the appropriate homologous sequence for inclusion in the vector. One or more nucleic acid constructs may integrate, which may affect the level of recombinant protein produced. [Rine et al., *Proc. Natl. Acad. Sci. USA*, 80:6750 (1983)]. The chromosomal sequences included in the vector can occur either as a single segment in the vector, which results in the integration of the entire vector, or two segments homologous to adjacent segments in the chromosome and flanking an expression cassette included in the vector, which can result in the stable integration of only the expression cassette.

Extrachromosomal and integrating nucleic acid constructs may contain selectable markers that allow for selection of yeast strains that have been transformed. Selectable markers may include, but are not limited to, biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a selectable marker may also provide yeast with the ability to grow in the presence of toxic compounds, such as metal. For example, the presence of CUP1 allows yeast to grow in the presence of copper ions. [Butt et al., *Microbiol. Rev.*, 51:351 (1987)].

Many vectors have been developed for transformation into many yeasts. For example, vectors have been developed for the following yeasts: *Candida albicans* [Kurtz et al., *Mol. Cell. Biol.*, 6:142 (1986)], *Candida maltose* [Kunze et al., *J. Basic Microbiol.*, 25:141 (1985)], *Hansenula polymorpha* [Gleeson et al., *J. Gen. Microbiol.*, 132:3459 (1986); Roggenkamp et al., *Mol. Gen. Genet.*, 202:302 (1986)], *Kluyveromyces fragilis* [Das et al., *J. Bacteriol.*, 158: 1165 (1984)], *Kluyveromyces lactis* [De Louvencourt et al., *J. Bacteriol.*, 154:737 (1983); van den Berg et al., *Bio/Technology*, 8:135 (1990)], *Pichia guillerimondii* [Kunze et al., *J. Basic Microbiol.*, 25:141 (1985)], *Pichia pastoris* [Cregg et al., *Mol. Cell. Biol.*, 5: 3376, (1985); U.S. Pat. Nos. 4,837,148 and 4,929,555], *Saccharomyces cerevisiae* [Hinnen et al., *Proc. Natl. Acad. Sci. USA*, 75:1929 (1978); Ito et al., *J. Bacteriol.*, 153:163 (1983)], *Schizosaccharomyces pombe* [Beach and Nurse, *Nature*, 300:706 (1981)], and *Yarrowia lipolytica* [Davidow et al., *Curr. Genet.*, 10:39 (1985); Gaillardin et al., *Curr. Genet.*, 10:49 (1985)].

Examples of Vectors Useful in Insect Cells

Baculovirus vectors have been developed for infection into several insect cells and may be used to produce nucleic acid constructs that contain an expression cassette of the invention. For example, recombinant baculoviruses have been developed for *Aedes aegypti, Autographa californica, Bombyx mori, Drosophila melanogaster, Spodoptera frugiperda*, and *Trichoplusia ni* [PCT Pub. No. WO 89/046699; Carbonell et al., *J. Virol.*, 56:153 (1985); Wright, *Nature*, 321: 718 (1986); Smith et al., *Mol. Cell. Biol.*, 3: 2156 (1983); and see generally, Fraser et al., *In Vitro Cell. Dev. Biol.*, 25:225 (1989)]. Such a baculovirus vector may be used to introduce an expression cassette into an insect and provide for the expression of a leader protein within the insect cell.

Methods to form a nucleic acid construct having an expression cassette of the invention inserted into a baculovirus vector are well known in the art. Briefly, an expression cassette of the invention is inserted into a transfer vector, usually a bacterial plasmid which contains a fragment of the baculovirus genome, through use of common recombinant methods. The plasmid may also contain a polyhedrin polyadenylation signal [Miller et al., *Ann. Rev. Microbiol.*, 42:177 (1988)] and a prokaryotic selection marker, such as ampicilling resistance, and an origin of replication for selection and propagation in *Escherichia coli*. A convenient transfer vector for introducing foreign genes into AcNPV is pAc373. Many other vectors, known to those of skill in the art, have been designed. Such a vector is pVL985 [Luckow and Summers, *Virology*, 17:31 (1989)].

A wild-type baculoviral genome and the transfer vector having an expression cassette insert are transfected into an insect host cell where the vector and the wild-type viral genome recombine. Methods for introducing an expression cassette into a desired site in a baculovirus virus are known in the art. [Summers and Smith, Texas Agricultural Experiment Station Bulletin No. 1555, 1987. Smith et al., *Mol. Cell. Biol.*, 3:2156 (1983); and Luckow and Summers, *Virology*, 17:31 (1989)]. For example, the insertion can be into a gene such as the polyhedrin gene, by homologous double crossover recombination; insertion can also be into a restriction enzyme site engineered into the desired baculovirus gene [Miller et al., *Bioessays*, 4:91 (1989)]. The expression cassette, when cloned in place of the polyhedrin gene in the nucleic acid construct, will be flanked both 5' and 3' by polyhedrin-specific sequences. An advantage of inserting an expression cassette into the polyhedrin gene is that inclusion bodies resulting from expression of the wild-type polyhedrin gene may be eliminated. This may decrease contamination of leader proteins produced through expression and formation of inclusion bodies in insect cells by wild-type proteins that would otherwise form inclusion bodies in an insect cell having a functional copy of the polyhedrin gene.

The packaged recombinant virus is expressed and recombinant plaques are identified and purified. Materials and methods for baculovirus and insect cell expression systems are commercially available in kit form. (Invitrogen, San Diego, Calif., USA ("MaxBac" kit)). These techniques are generally known to those skilled in the art and fully described in Summers and Smith, Texas Agricultural Experiment Station Bulletin No. 1555, 1987.

Plasmid-based expression systems have also been developed the may be used to introduce an expression cassette of the invention into an insect cell and produce a leader protein. [McCarroll and King, *Curr. Opin. Biotechnol.*, 8:590 (1997)]. These plasmids offer an alternative to the production of a recombinant virus for the production of leader proteins.

Examples of Vectors Useful in Mammalian Cells

An expression cassette of the invention may be inserted into many mammalian vectors that are known in the art and are commercially available. (CLONTECH, Carlsbad, Calif.; Promega, Madision, Wis.; Invitrogen, Carlsbad, Calif.). Such vectors may contain additional elements such as enhancers and introns having functional splice donor and acceptor sites.

Nucleic acid constructs may be maintained extrachromosomally or may integrate in the chromosomal DNA of a host cell. Mammalian vectors include those derived from animal viruses, which require trans-acting factors to replicate. For example, vectors containing the replication systems of papovaviruses, such as SV40 [Gluzman, *Cell*, 23:175 (1981)] or polyomaviruses, replicate to extremely high copy number in the presence of the appropriate viral T antigen. Additional examples of mammalian vectors include those derived from bovine papillomavirus and Epstein-Barr virus. Additionally, the vector may have two replication systems, thus allowing it to be maintained, for example, in mammalian cells for expression and in a prokaryotic host for cloning and amplification. Examples of such mammalian-bacteria shuttle vectors include pMT2 [Kaufman et al., *Mol. Cell. Biol.*, 9:946 (1989)] and pHEBO [Shimizu et al., *Mol. Cell. Biol.*, 6:1074 (1986)].

E) Host Cells

Host cells producing the recombinant precursor polypeptides for the methods of the invention include prokaryotic and eukaryotic cells of single and multiple cell organisms. Bacteria, fungi, plant, insect, vertebrate and its subclass mammalian cells and organisms may be employed. Single cell cultures from such sources as well as functional tissue and whole organisms can operate as production hosts according to the invention. Examples include *E. Coli*, tobacco plant culture, maize, soybean, fly larva, mice, rats, hamsters, as well as CHO cell cultures, immortal cell lines and the like.

In a preferred embodiment, bacteria are used as host cells. Examples of bacteria include, but are not limited to, Gram-negative and Gram-positive organisms. *Escherichia coli* is a preferred organism for expression of preselected polypeptides and amplification of nucleic acid constructs. Many publicly available *E. coli* strains include K-strains such as MM294 (ATCC 31, 466); X1776 (ATCC 31, 537); KS 772 (ATCC 53, 635); JM109; MC1061; HMS174; and the B-strain BL21. Recombination minus strains may be used for nucleic acid construct amplification to avoid recombination events. Such recombination events may remove concatemers of open reading frames as well as cause inactivation of an expression cassette. Furthermore, bacterial strains that do not express a select protease may also be useful for expression of preselected polypeptides to reduce proteolytic processing of expressed polypeptides. Such strains include, for example, Y1090hsdR, which is deficient in the Ion protease.

Eukaryotic cells may also be used to produce a preselected polypeptide and for amplifying a nucleic acid construct. Eukaryotic cells are useful for producing a preselected polypeptide when additional cellular processing is desired. For example, a preselected polypeptide may be expressed in a eukaryotic cell when glycosylation of the polypeptide is desired. Examples of eukaryotic cell lines that may be used include, but are not limited to: AS52, H187, mouse L cells, NIH-3T3, HeLa, Jurkat, CHO-K1, COS-7, BHK-21, A-431, HEK293, L6, CV-1, HepG2, HC11, MDCK, silkworm cells, mosquito cells, and yeast.

F) Transformation

Methods for introducing exogenous DNA into bacteria are available in the art, and usually include either the transformation of bacteria treated with $CaCl_2$ or other agents, such as divalent cations and DMSO. DNA can also be introduced into bacterial cells by electroporation, use of a bacteriophage, or ballistic transformation. Transformation procedures usually vary with the bacterial species to be transformed [see, e.g., Masson et al., *FEMS Microbiol. Lett.*, 60: 273 (1989); Palva et al., *Proc. Natl. Acad. Sci. USA*, 79: 5582 (1982); EPO Publ. Nos. 036 259 and 063 953; PCT Publ. No. WO 84/04541 [*Bacillus*], Miller et al., *Proc. Natl. Acad. Sci. USA*, 8: 856 (1988); Wang et al., *J. Bacteriol.*, 172: 949 (1990) [*Campylobacter*], Cohen et al., *Proc. Natl. Acad. Sci. USA*, 69: 2110 (1973); Dower et al., *Nuc. Acids Res.*, 16: 6127 (1988); Kushner, "An improved method for transformation of *Escherichia coli* with ColE1-derived plasmids", in: *Genetic Engineering: Proceedings of the International Symposium on Genetic Engineering* (eds. H. W. Boyer and S. Nicosia), (1978); Mandel et al., *J. Mol. Biol.*, 53: 159 (1970); Taketo, *Biochim. Biophys. Acta*, 949: 318 (1988) [*Escherichia*], Chassy et al., *FEMS Microbiol. Lett.*, 44: 173 (1987) [*Lactobacillus*], Fiedler et al., *Anal. Biochem*, 170: 38 (1988) [*Pseudomonas*], Augustin et al., *FEMS Microbiol. Lett.*, 66: 203 (1990) [*Staphylococcus*], Barany et al., *J. Bacteriol.*, 144: 698 (1980); Harlander, "Transformation of *Streptococcus lactis* by electroporation", in: *Streptococcal Genetics* (ed. J. Ferretti and R. Curtiss III), (1987); Perry et al., *Infec. Immun.*, 32: 1295 (1981); Powell et al., *Appl. Environ. Microbiol.* 54: 655 (1988); Somkuti et al., *Proc. 4th Eur. Cong. Biotechnology*, 1: 412 (1987) [*Streptococcus]*].

Methods for introducing exogenous DNA into yeast hosts are well-known in the art, and usually include either the transformation of spheroplasts or of intact yeast cells treated with alkali cations. Transformation procedures usually vary with the yeast species to be transformed [see, e.g., Kurtz et al., *Mol. Cell. Biol.*, 6:142 (1986); Kunze et al., *J. Basic Microbiol.*, 25:141 (1985) [*Candida*], Gleeson et al., *J. Gen. Microbiol.*, 132:3459 (1986); Roggenkamp et al., *Mol. Gen. Genet.*, 202:302 (1986) [*Hansenula*], Das et al., *J. Bacteriol.*, 158: 1165 (1984); De Louvencourt et al., *J. Bacteriol.*, 754:737 (1983); Van den Berg et al., *Bio/Technology*, 8:135 (1990) [*Kluyveromyces*], Cregg et al., *Mol. Cell. Biol.*, 5:3376 (1985); Kunze et al., *J. Basic Microbiol.*, 25:141 (1985); U.S. Pat. Nos. 4,837,148 and 4,929,555 [*Pichia*], Hinnen et al., *Proc. Natl. Acad. Sci. USA*, 75:1929 (1978); Ito et al., *J. Bacteriol.*, 153:163 (1983) [*Saccharomyces*], Beach and Nurse, *Nature*, 300:706 (1981) [*Schizosaccharomyces*], and Davidow et al., *Curr. Genet.*, 10:39 (1985); Gaillardin et al., *Curr. Genet.*, 10:49 (1985) [*Yarrowia]*].

Exogenous DNA is conveniently introduced into insect cells through use of recombinant viruses, such as the baculoviruses described herein.

Methods for introduction of heterologous polynucleotides into mammalian cells are known in the art and include lipid-mediated transfection, dextran-mediated transfection, calcium phosphate precipitation, polybrene-mediated transfection, protoplast leader, electroporation, encapsulation of the polynucleotide(s) in liposomes, biollistics, and direct microinjection of the DNA into nuclei. The choice of method depends on the cell being transformed as certain transformation methods are more efficient with one type of cell than another. [Felgner et al., *Proc. Natl. Acad. Sci.*, 84:7413 (1987); Felgner et al., *J. Biol. Chem.*, 269:2550 (1994); Graham and van der Eb, *Virology*, 52:456 (1973); Vaheri and Pagano, *Virology*, 27:434 (1965); Neuman et al., *EMBO J.*, 1:841 (1982); Zimmerman, *Biochem. Biophys. Acta.*, 694: 227 (1982); Sanford et al., *Methods Enzymol.*, 217:483 (1993); Kawai and Nishizawa, *Mol. Cell. Biol.*, 4:1172 (1984); Chaney et al., *Somat. Cell Mol. Genet.*, 12:237 (1986); Aubin et al., *Methods Mol. Biol.*, 62:319 (1997)]. In addition, many commercial kits and reagents for transfection of eukaryotic are available.

Following transformation or transfection of a nucleic acid into a cell, the cell may be selected for through use of a selectable marker. A selectable marker is generally encoded on the nucleic acid being introduced into the recipient cell. However, co-transfection of selectable marker can also be used during introduction of nucleic acid into a host cell. Selectable markers that can be expressed in the recipient host cell may include, but are not limited to, genes which render the recipient host cell resistant to drugs such as actinomycin C₁, actinomycin D, amphotericin, ampicillin, bleomycin, carbenicillin, chloramphenicol, geneticin, gentamycin, hygromycin B, kanamycin monosulfate, methotrexate, mitomycin C, neomycin B sulfate, novobiocin sodium salt, penicillin G sodium salt, puromycin dihydrochloride, rifampicin, streptomycin sulfate, tetracycline hydrochloride, and erythromycin. [Davies et al., *Ann. Rev. Microbiol.*, 32: 469, (1978)]. Selectable markers may also include biosynthetic genes, such as those in the histidine, tryptophan, and leucine biosynthetic pathways. Upon transfection or tranformation of a host cell, the cell is placed into contact with an appropriate selection marker.

For example, if a bacterium is transformed with a nucleic acid construct that encodes resistance to ampicillin, the transformed bacterium may be placed on an agar plate containing ampicillin. Thereafter, cells into which the nucleic acid construct was not introduced would be prohibited from growing to produce a colony while colonies would be formed by those bacteria that were successfully transformed.

EXAMPLES

The following series of Examples illustrates procedures for cloning, expression and detection of a precursor polypeptide that can be used to generate a peptide of interest. Examples 1 though 5 provide the protocol and experimental procedures used for preparing a peptide of interest using the clostripain cleavage techniques of the present invention. Example 6 provides the application of these protocols and procedures to a specific peptide. The peptide chosen is GLP-2(1-34). Example 7 provides data showing the parameters for affecting selectivity of the clostripain cleavage. This series of examples are intended to illustrate certain aspects of the invention and are not intended to be limiting thereof.

Example 1

Figure 1:
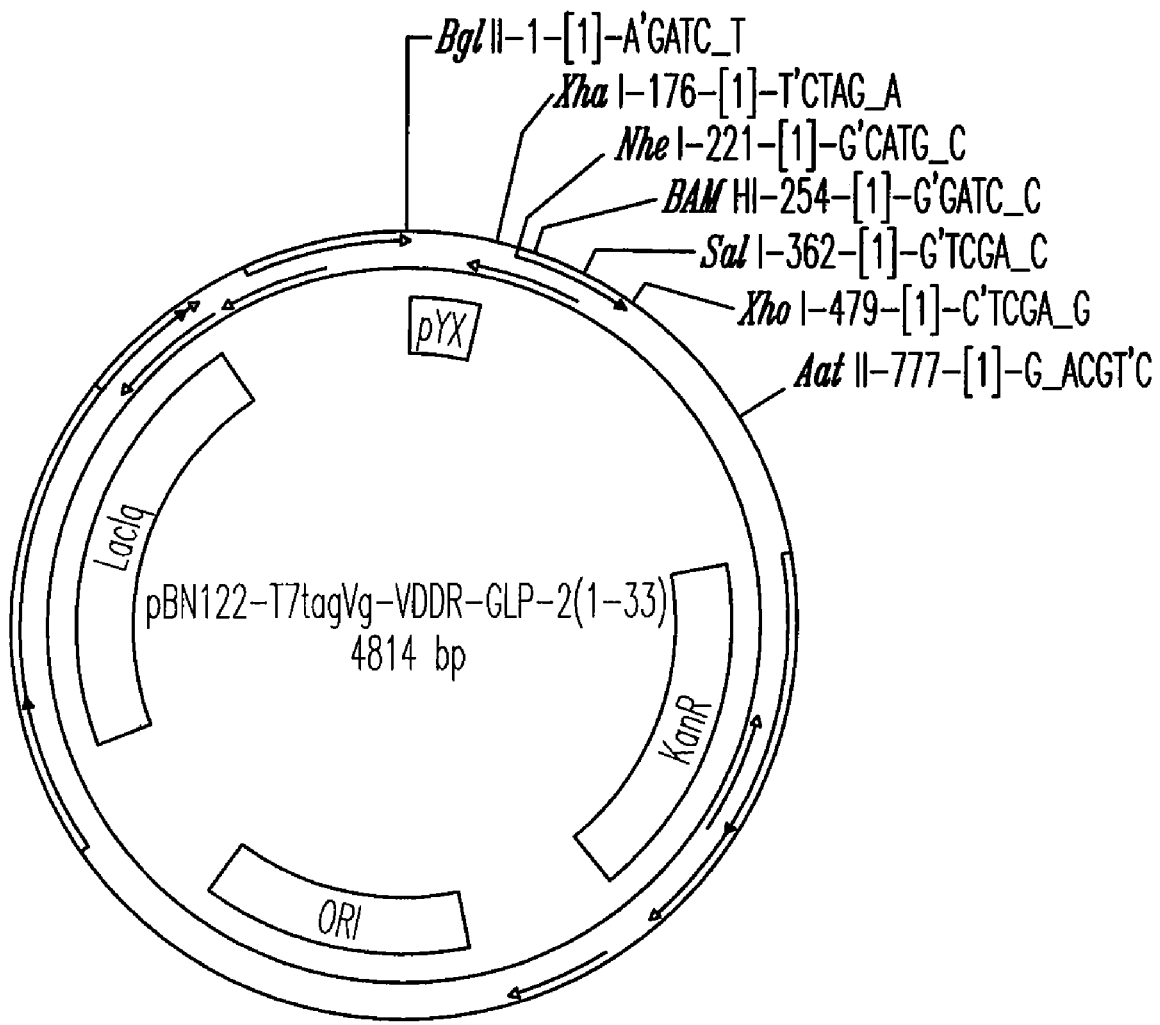
FIG. 1 provides a schematic diagram of a pBN122 vector containing a DNA segment encoding the precursor polypeptide. PYX; *chlorella* virus promoter.

Construction of a Vector that Contains DNA which Encodes a Desired Precursor Polypeptide In order to express the desired precursor polypeptide, a preferred expression vector, pBN122, was constructed through use of PCR, restriction enzyme digestion, DNA ligation, transformation into a bacterial host, and screening procedures according to procedures described, for example, in Sambrook et al., Molecular Cloning ($2^{nd}$ edition). Preferably the vector contains regulatory elements that provide for high level expression of a desired precursor polypeptide. Examples of such regulatory elements include, but are not limited to: an inducible promoter such as the *chlorella* virus promoter [U.S. Pat. No. 6,316,224]; an origin of replication for maintaining the vector in high copy number such as a modified pMB1 promoter; a LaqIq gene for promoter suppression; an aminophophotransferase gene for kanamycin resistance; and a GST terminator for terminating mRNA synthesis. (FIG. 1).

*E. Coli* is a preferred host. To clone the expression cassette of T7tag-Vg-VDDR-GLP-2(1-33), PCR or multiple PCR extension was performed to synthesize DNA encoding T7tag, Vg, and GLP-2 gene using preferred codons for *E. coli*. DNA providing the T7 gene 10 ribosome binding site and the first twelve amino acids (T7tag) after initiation codon was cloned into plasmid pBN122 at XbaI-SalI sites between the promoter and the terminator. DNA encoding the hydrophobic core of the Vestigial (Vg) gene [Williams et al., *Control of Drosophila wing and haltere development by the nuclear vestigial gene product, Genes Dev. Dec.* 5, (12B:2481-95 (1991)] was cloned into the plasmid at BamHI-SalI sites. DNA encoding GLP-2(1-33) was cloned into the above plasmid at SalI-XhoI sites. Plasmids were transformed into *E. coli* using heat shock or electroporation procedures ($2^{nd}$ edition, Sambrook et. al).

Cells were streaked onto LB+Kanamycin+agar plates, cultures were grown in LB+Kanamycin media from single colonies. Plasmids from these cultures were prepared, screened by restriction enzyme digestion, and sequenced using DNA sequencers. The cultures with the correct plasmid sequence were saved in glycerol stock at −80° C. or below.

Alternative peptides can be cloned by this method using different combinations of restriction enzymes and restriction sites according to methods known in the art.

Example 2

Expression of the Precursor Polypeptide

A shaking flask was inoculated from a glycerol stock of an *E. coli* strain containing a pBN122 plasmid encoding the desired polypeptide. A complex media containing 1% tryptone was employed that was supplemented with glucose and kanamycin. The shaking culture was grown in a rotary shaker at 37° C. until the optical density was 1.5±0.5 at 540 nm. The contents of the shaking flask culture were then used to inoculate a 5 L fermentation tank containing a defined minimal media containing magnesium, calcium, phosphate and an assortment of trace metals. Glucose served as the carbon source. Kanamycin was added to maintain selection of the recombinant plasmid. During fermentation, dissolved oxygen was controlled at 40% by cascading agitation and areation with additional oxygen. A solution of ammonium hydroxide was used to control the pH at about pH 6.9.

Figure 2:
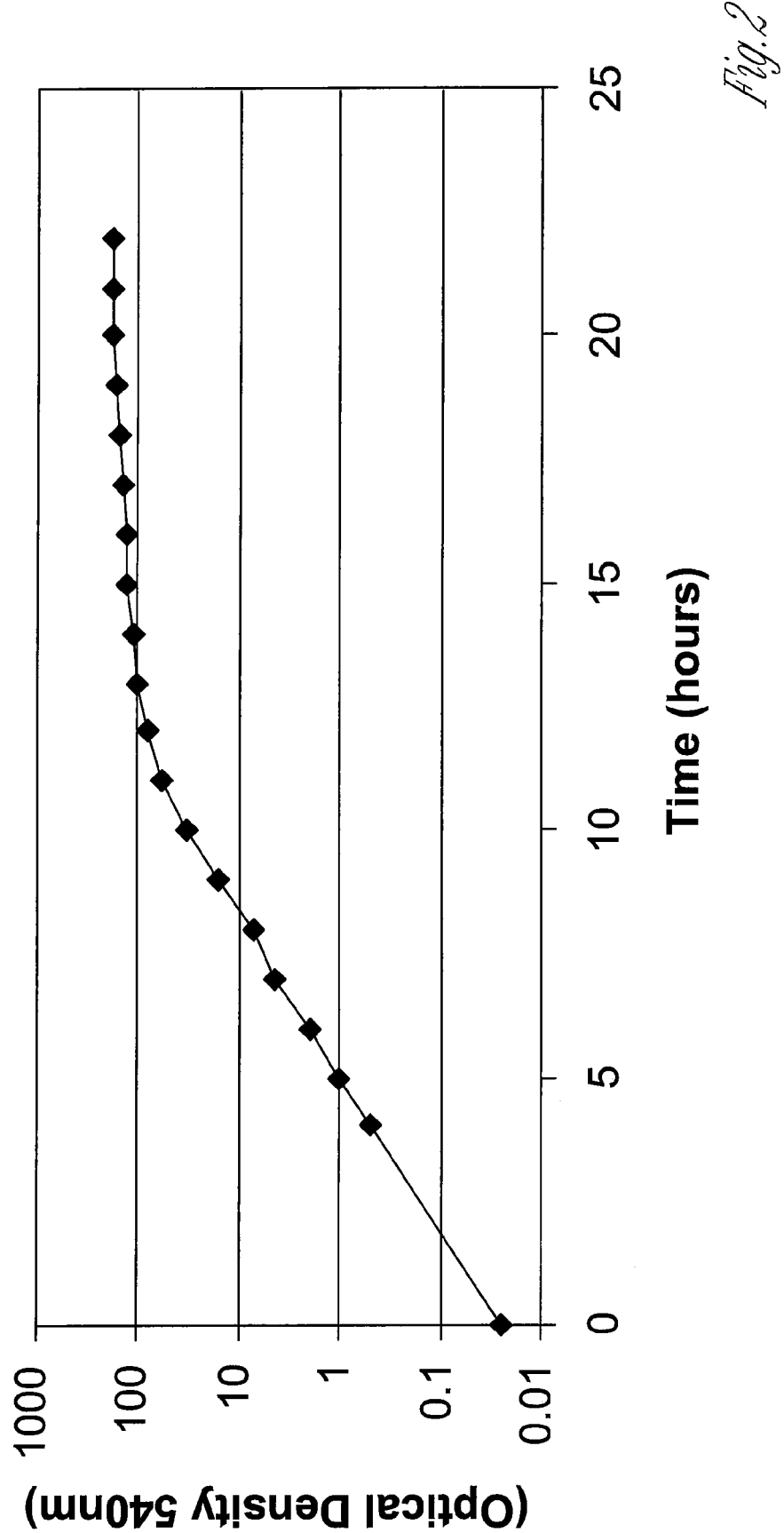
FIG. 2 illustrates a typical growth curve of recombinant *E. coli*. Addition of IPTG for induction generally occurs between 10 and 11 hours. Cells are harvested 6-10 hours after IPTG induction. Growth as evidenced by the increase in optical density at 540 nm.

Cell growth was monitored at 540 nm until a target optical density of between about 75 OD, was reached and isopropyl-βD-thiogalatoside (IPTG at between 0.1 and 1.0 mM) was added to induce expression of the desired polypeptide (FIG. 2). When induction was complete, the cells were cooled in the fermenter and harvested with a continuous flow solid bowl centrifuge. The sedimented cells were frozen until used.

The frozen cell pellet was thawed and homogenized in 50 mM Tris, 2.5 mM EDTA, pH 7.8. Inclusion bodies were washed in water and were collected by solid bowl centrifugation. Alternatively, cells were suspended in 8 M urea then lysed by conventional means and then centrifuged. The supernatant fluid contained the precursor peptide.

Example 3

Detection of Precursor Polypeptides

To monitor the production of the precursor polypeptide preparation, 100 μL of sample (fermentation culture or from a purification process step) was dissolved in 1 mL 71% phenol, 0.6 M citric acid, vortexed and bath sonicated briefly. The dissolved sample was diluted 12.5-fold to 50-fold in 50% acetonitrile, 0.09% TFA, and centrifuged to render it compatible with the chromatography system to be employed. The dissolved precursor polypeptide and *E. coli* cell products remain soluble in the diluted solution, while other insoluble matters are removed.

The samples were then analyzed using a tapered, 5 micron Magic Bullet C4 column (Michrom BioResources). The absolute peak area of the precursor polypeptide was obtained by recording the absorbance at 280 nm as a function of time. The HPLC method was as follows:
1. Mobile phase: A-0.1% TFA in water, B-0.08% TFA in acetonitrile.
2. Detection: 280 nm.
3. Gradient: 1 mL/min. at 50° C., using 10-90% B(2.5 min.), 90-10% B(0.1 min.), 10% B(1.4 min.). The gradient may be modified for better separation of different precursor peptides.

4. Injection: 1-10 µL.

Figure 3B:
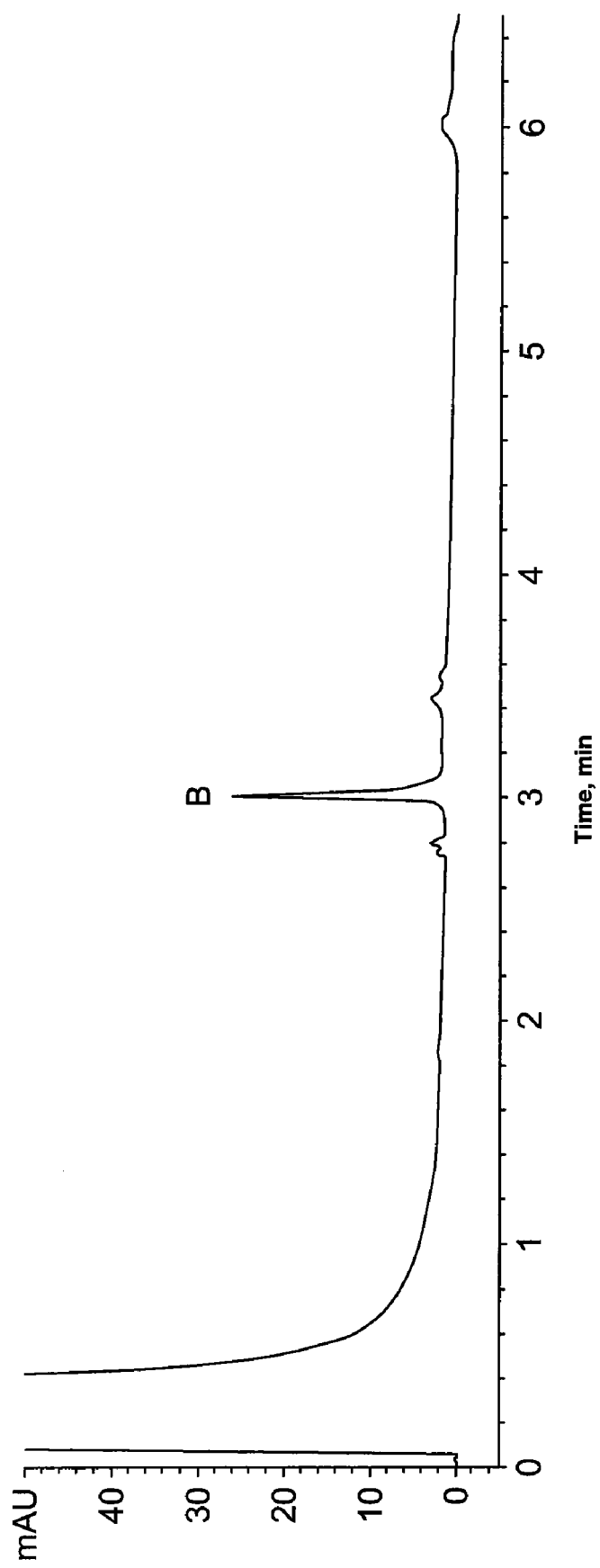
FIG. 3 illustrates HPLC analysis of cell free extracts from typical fermentations producing either A: T7tag-Vg-VDDR-GLP-2(1-33)A2G (SEQ ID NO:30) (8.7 gm/L); or B: T7tag-GSDR-GLP-1(1-33) A2G-PGDR-GLP-2(1-33) A2G (10.4 gm/L). In each case cell samples were taken after 10 hours of induction and prepared for analysis as described in the text.

The precursor polypeptide peak area is compared to the peak area from a reference polypeptide standard chromatographed under the same conditions. The precursor polypeptide concentration is determined by normalizing for the different calculated molar absorptivities ($\epsilon_{280nm}$) of a standard and the precursor polypeptide, injection volumes, and dilution factors. Alternatively, the molar absorbtivity of the precursor peptide can be estimated from the proportional contributions of the molar absorbtivities at 280 nm of the constituent amino acids. Multiplying the polypeptide concentration times the process step volume yields the total quantity of polypeptide. (FIG. 3).

Example 4

Cleavage of Precursor Polypeptides

Approximately 100 grams of E. coli cells containing the desired precursor polypeptide were lysed by combining them with approximately two liters of 8 M urea containing 0.1 M $NH_4OH$, pH 10.0 (adjusted with reagent grade HCl). This treatment caused the cells to lyse and produce a cell free extract. Alternatively, cells can be lysed with 8 M urea at neutral pH. Lysis methods utilizing urea are preferably used to lyse cells that express soluble precursor polypeptides.

Recombinant clostripain was prepared as 1400 unit/mL solution. Dilutions were made, when necessary, in 25 mM HEPES buffer at pH 7.1 with 10 mM DTT and 5 mM $CaCl_2$ and were stored at 4° C. or in an ice bucket before use.

Wild type clostripain (different from recombinant clostripain) was purchased from a vendor (200 u/mg dry weight, Worthington). The dried enzyme was kept at 4° C. A stock solution was made by resolubilization of the dried enzyme in 25 mM HEPES buffer at pH 7.1 with 10 mM DTT and 5 mM $CaCl_2$ and was stored at 4° C. or in an ice bucket before use. Wild-type and recombinant clostripain produced equivalent results.

In one example, the lysate was homogenized for 3 minutes using a commercial homogenizer. The suspension was then centrifuged for 45 minutes at 16,900×g. The supernatant fluid was diluted to a final protein concentration of from 0.1 to 2 mg/ml in 50 mM HEPES buffer, containing 1 mM $CaCl_2$ and 1 mM cysteine. Alternately the lysate was subjected to tangential flow filtration (TFF) using an 8 kD exclusion membrane. The loss in the filtered volume was replaced with 50 mM HEPES containing 0-3 M urea, 1 mM $CaCl_2$, and 1 mM cysteine, pH 6.0-6.9.

For cells that express precursor polypeptides in inclusion bodies, cell lysis was preferably performed by sonication in 50 mM Tris, 2.5 mM EDTA, pH 7.5. Centrifugation was then performed to sediment and wash the inclusion bodies. After the supernatant fluid was decanted, the pellet was dissolved in 8 M urea, mechanically homogenized for 2 min then centrifuged to remove the insoluble material. The supernatant fluid was treated as above to reduce the urea concentration.

Figure 4:
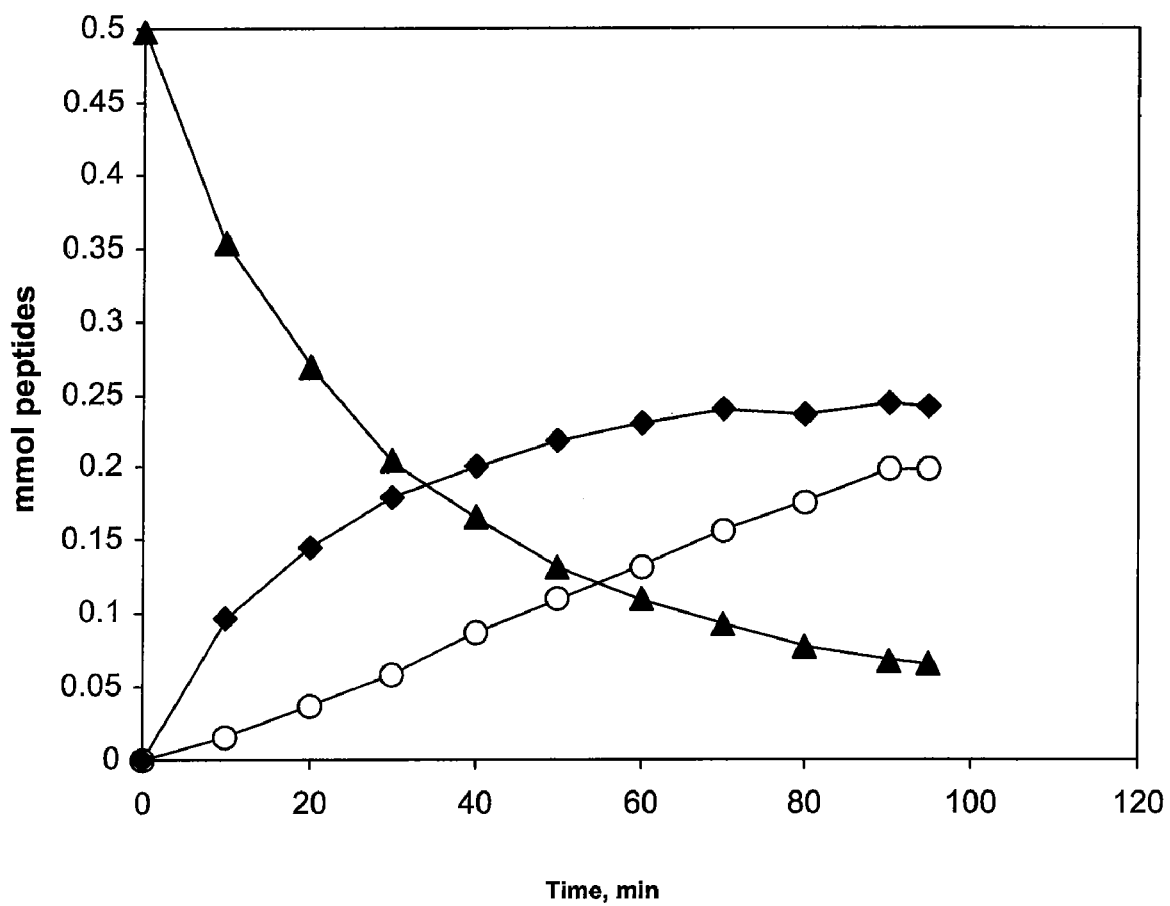
FIG. 4 illustrates the digestion of a precursor polypeptide, T7tag-Vg-VDDR-GLP-2(1-33) A2G, in a cell free extract with clostripain to produce GLP-2(1-33) A2G and a GLP-2 fragment (21-33). The digestion was conducted by combining 0.2 units of clostripain per mg of the precursor polypeptide. The precursor polypeptide was present in the digestion mixture at a concentration of about 0.45 mg/ml. (closed triangle) T7tag-Vg-VDDR-GLP-2(1-33) A2G; (closed diamond) GLP-2(1-33) A2G; (closed circle) GLP-2 fragment (21-33).
Figure 5C:
FIG. 5 illustrates typical liquid chromatography-mass spectroscopy (LC-MS) analysis of the reaction products of a clostripain digestion of a precursor polypeptide. Panel (A) shows the relative abundance chromatogram. Panel (B)
Figure 5D:
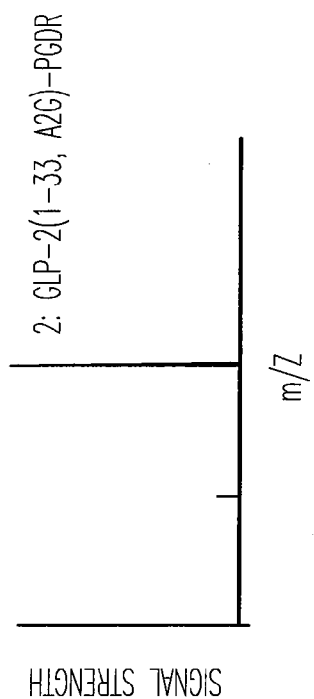
Figure 5A:
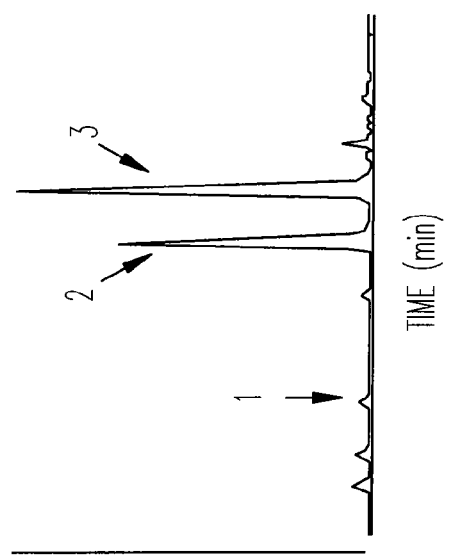
Figure 5B:
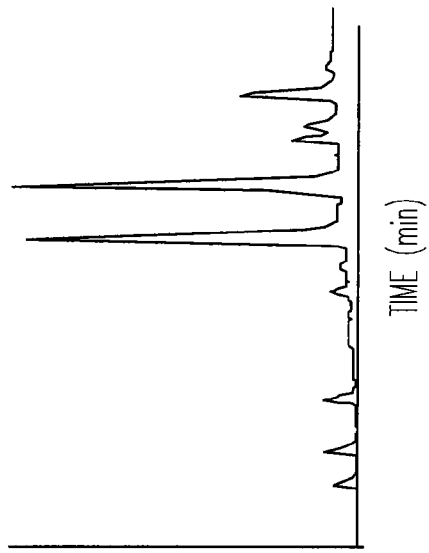
Figure 5E:
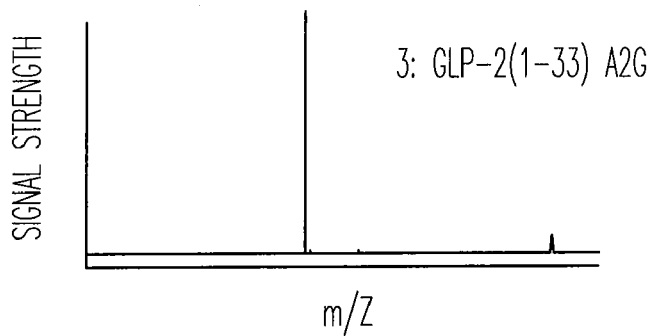

Enzymatic digestion of the precursor polypeptide was initiated by combining about 0.01 to 2 U/mg of precursor polypeptide and clostripain. In this example, the reaction contained 0.45 mg/ml of precursor polypeptide and 0.2 units clostripain per mg precursor polypeptide. The digest was allowed to proceed for up to 3 hr (FIG. 4). Both wild-type and recombinant clostripain produced equivalent results.

Example 5

Identification of Reactants and Products Following Digestion of a Precursor Polypeptide by Clostripain The identity of products produced by cleavage of a precursor polypeptide by clostripain was determined by liquid chromatography/mass spectroscopy (LC/MS) analysis. In one example, a cleavage reaction containing clostripain and a T7tag-GSDR-GLP-2(1-33)A2G-PGDR-GLP-2(1-33)A2G precursor polypeptide was assembled that contained 3 mg/ml precursor polypeptide and 0.4 Units clostripain per mg of precursor peptide. The cleavage reaction was conducted for 80 minutes and resulted in a 90% conversion to the indicated products. A 30 µl aliquot was obtained from the cleavage reaction and mixed with 100 µl of a solution containing 8 M urea to which 20 µl of 0.1 M EDTA (pH 6.5) was added. Samples were clarified by centrifugation if needed.

Prepared samples (5 µl) were injected into a Finnigan LCQ DUO ion trap mass spectrometer equipped with a Waters Symmetry C18 column operating in a positive ion electrospray mode for analysis. During the sampling period, molecular weight determination was performed by full scan mass spectrometry. Typical MS conditions included a scan range of 300-2000 Da/e.

LC analysis was performed on a system consisting of a Xcaliber software, ThermoQuest Surveyor MS pumps, a ThermoQuest Surveyor UV spectrophotometric PDA detector and a ThermoQuest Surveyor autosampler. The parameters of the chromotagraphic column are indicated below.

| Column Manufacturer: | Waters Company |
|---|---|
| Packing support: | Symmetry C18 |
| Particle size: | 3.5 µm |
| Pore size: | 100 Å |
| Column size: | 2.1 × 150 mm |
| Guard column: | 3.5 µm, 2.1 × 10 mm |

Chromatographic conditions were: flow-rate 300 ul/min and buffers A: 0.1% TFA, B: acetonitrile, 0.08% TFA. The gradient was from 15% B to 30% B in 3 min, to 55% B in 19 min, to 90% B in 3 min, temperature 50° C. Detection was over the range 210-320 nm on the PDA detector, Channel A 214 nm, channel B 280 nm. Mass detection was over the 300-2000 Da/e range. All the samples were analyzed on an LCQ-DUO EST mass spectrometer. Usually, the masses observed with significant relative abundance are the doubly or triply charged ions, i.e. $[M+2H]^{2+}/2$ or $[M+3H]^{3+}/3$. The complete mass spectrum as a function of time could be evaluated following the chromatographic procedure through use of the system software. This allows for analysis of individual peaks that eluted from the column.

The results shown in FIG. 5 illustrate that the identity of peptides produced in a cleavage reaction can be identified. FIG. 5 also shows that cleavage at DRH (FIG. 5, peaks 2 and 3) is nearly quantitative (90% yield), while the cleavage at ARD (FIG. 5, peak 1) was minimal. A purified preparation of GLP-2(1-33)A2G was subjected to complete amino acid sequence analysis which confirmed the structure of this peptide.

Example 6

Effects of pH and Urea on the Digestion of a Precursor Polypeptide by Clostripain A. Influence of pH on the Cleavage of a Precursor Polypeptide by Clostripain The pH was varied in a series of clostripain cleavage reactions using the soluble six-copy GLP-2 polypeptide as substrate (T7tag-GSDR-GLP-2(1-34)$_6$). In the first set of reactions, the buffer utilized was varied with the pH of the reaction mixture, as follows:

For pH 6.28: 50 mM of piperazine-NN'-bis(2-ethanesulfonic acid) (PIPES);
For pH 6.55: 4-(2-hydroxyethyl)-1-piperazineethanesulfonic acid) (HEPES);
For pH 7.50: 4-(2-hydroxyethyl)-1-piperazineethanesulfonic acid) (HEPES);
For pH 7.94: 3-(cyclohexylamino)-2-hydroxy-1-propanesulfonic acid) (CAPSO); For pH 8.82: 3-(cyclohexylamino)-2-hydroxy-1-propanesulfonic acid) (CAPSO).

The reaction mixture contained 0.33 mg/mL soluble six-copy GLP-2 precursor polypeptide in a cleavage reaction containing 5 mM $CaCl_2$, 10 mM DTT, 4.2 units clostripain per mg of precursor polypeptide, and an appropriate buffer at pH 6.28, 6.55, 7.50, 7.94 or 8.82. The reaction temperature was 20° C. The pH of the cleavage reaction was measured just before addition of clostripain to initiate the reaction. Aliquots of the cleavage reaction were removed at selected time intervals (3, 10, 20 and 40 min) and quenched in a volume of a solution containing 7.2 M urea and 1.2 M HCl that was three times the volume of the aliquot. The quenched aliquot was centrifuged before injection into the HPLC. Peptide cleavage products were detected by the HPLC at 214 nm and 280 nm. As illustrated in FIG. 6A, the fastest cleavage velocity was observed at a pH range between about 6.0 and about 7.0. However, loss of the GLP-2 monomer by continued internal cleavage was minimized by use of buffer at pH 6.5. Product yield was typically greater than 70% using the described protocol.

B. Influence of Urea on the Cleavage of a Precursor Polypeptide by Clostripain

The effect of urea on the cleavage of a precursor polypeptide by clostripain was tested by cleaving a T7tag-Vg-VDDR-GLP-2(1-33)A2G precursor polypeptide in the presence of various urea concentrations. The precursor polypeptide (0.4 mg/ml) was cleaved with clostripain (3.3 Units per mg of precursor polypeptide) in a reaction mixture containing 50 mM HEPES buffer (pH 6.3), 1 mM $CaCl_2$, 1 mM cysteine, and various concentrations of urea at 25° C. The urea concentrations tested were 0, 0.5, 1.0 and 1.5 M. Aliquots of the cleavage reaction were removed at one minute intervals for 10 minutes and quenched by addition of EDTA to a final concentration of 10 mM. Peptide cleavage products were analyzed by the HPLC at 214 nm and 280 nm as previously described. As illustrated in FIG. 6B, the fastest cleavage velocity was observed in the absence of urea. Concentrations of urea above 1.5 M caused a decreasing yield to about 20% at 6.5 M urea.

Example 7

Effect of Organic Solvents on the Digestion of a Precursor Polypeptide by Clostripain The effect of organic solvents on the cleavage of a precursor polypeptide by clostripain was tested by cleaving a T7tag-Vg-VDDR-GLP-2(1-33)A2G precursor polypeptide in the presence of various concentrations of ethanol or acetonitrile (FIGS. 7A and 7B).

In one example, the precursor polypeptide (1.2 mg/mL) was cleaved with clostripain (5.0 units per mg of precursor polypeptide) in a reaction mixture containing 50 mM HEPES buffer (pH 6.7), 1 mM $CaCl_2$, 1 mM cysteine, and 4.8 M urea at 25° C. The ethanol concentrations tested were 10, 20 and 35% ethanol. The reaction was initiated by the addition of clostripain and allowed to proceed for 30 minutes. The reaction was terminated by the addition of EDTA to a final concentration of 17 mM. The products of the cleavage reaction were resolved by C4 reverse phase chromatography. Briefly, a 40 μL sample containing the cleavage products was injected into a Vydac C4 protein column and eluted from the column through application of a gradient composed of Buffer A (5% acetonitrile and 0.1% TFA) and Buffer B (95% acetonitrile and 0.1% TFA). The following gradient was used: time (minutes) 0, % B: 30; time 7.5, % B: 50; time 8.5, % B: 70; time 8.6, % B: 30; and time 11, % B: 30.

FIG. 7A illustrates the elution position of the major products of digestion (peak 1: (GLP-2(21-33)), peak 2: GLP-2(1-33)A2G, peak 3: precursor polypeptide). It can be seen that increasing concentrations of ethanol cause a) an increase in the rate of disappearance of the precursor polypeptide (peak 3), b) a concomitant increase in the rate of the appearance of the product (peak 2), and c) a decrease in the appearance of an undesired product (peak 1) produced by cleavage of a secondary cleavage site within the precursor polypeptide.

FIG. 7B illustrates the effects of ethanol and acetonitrile on the cleavage rate, and the extent of cleavage, of a precursor polypeptide by clostripain. It can be seen from the figure that the presence of ethanol or acetonitrile in the cleavage reaction increases the rate of cleavage of a precursor polypeptide as well as increases the yield of cleaved product. Another surprising result is that production of an undesired product produced by cleavage of a second cleavage site within the precursor polypeptide is decreased at increased ethanol or acetonitrile concentrations. These results show that the specificity of clostripain cleavage can be influenced by the presence or absence of an organic solvent in the cleavage reaction. Thus, the discovery that organic solvents can influence clostripain cleavage rate and specificity be used in conjunction with the methods to design clostripain cleavage sites, as disclosed herein, to produce precursor polypeptides that are selectively cleaved to yield desired products in high yield (in excess of 90%).

The complete amino acid sequence of a purified preparation of GLP-2(1-33)A2G prepared according to the above method was determined to confirm the composition of the peptide product.

Example 8

The Effect of Precursor Polypeptide and Clostripain Concentration

A. The Effect of Precursor Polypeptide Concentration

The concentration of the soluble six-copy GLP-2 polypeptide (T7tag-GSDR-[GLP-2(1-34)]$_6$) was varied in a series of cleavage reactions to ascertain how much precursor polypeptide can optimally be cleaved in a single reaction.

A stock solution of the soluble six-copy GLP-2 polypeptide was prepared in 10 mM Tris, 1 mM EDTA, 5 mM of $CaCl_2$, pH 8.0 buffer. Aliquots of the substrate stock solution were withdrawn and added to various reaction mixtures as needed. In this series of experiments the substrate concentration was varied within the reaction mixture as follows: 0.6, 1.2, 2.4 and 4.28 mg/mL. The buffer utilized was a phosphate-based buffer at 150 mM (ionic strength about 0.45 M), pH: 6.60±0.01. As before, 10 mM DTT was utilized in the reaction mixture. The reaction temperature was 21° C. and was initiated by the addition of clostripain. Hydrolysis was terminated at 25 minutes by the addition of 3 volumes of 7.2 M urea in 1.2 M HCl. Products of the reaction were analyzed by HPLC according to the procedure described in example 7. The results of the reaction are shown in FIG. 8A. The yield of GLP-2(1-34) was in excess of 90%.

The identity of the peptide product prepared according to the described method was confirmed by amino acid sequence analysis by LC-MS-MS as being GLP-2(1-34). It was determined that the product had a mass of 3921.6 ([M+3H+]=1308.3 m/z). The designated peak was further fragmented to yield the MS/MS data contained in Table 1. The calculated masses are from monoisotopes. The charges of the fragments were also indicated as (M+n H+), where n is the number of additional hydrogen ions.

were as follows: A: 5% acetonitrile and 0.1% TFA; B: 95% acetonitrile and 0.1% TFA. The injection volume was 20 μl for each sample. The products of the cleavage reaction were amidated on the C-terminus and were produced with a 25%

TABLE I

Observed Mass of Peptides from the LC-MS Chromatogram

| Fragments | Calc. Mass | Obs. Mass | Conv. Mass | n |
|---|---|---|---|---|
| HADGS FSDEM NTILD NLAAR DFINW LIQTK ITDR | 3920.9 | 1308.3 | 3922.08 | 3 |
| ADGS FSDEM NTILD NLAAR DFINW LIQTK ITDR | 3783.84 | 1262.37 | 3784.11 | 3 |
| DGS FSDEM NTILD NLAAR DFINW LIQTK ITDR | 3712.8 | 1238.97 | 3713.91 | 3 |
| GS FSDEM NTILD NLAAR DFINW LIQTK ITDR* | 3597.77 | 1200.64 | 3598.92 | 3 |
| FSDEM NTILD NLAAR DFINW LIQTK ITDR | 3410.72 | 1138.16 | 3411.48 | 3 |
| SDEM NTILD NLAAR DFINW LIQTK ITDR* | 3263.65 | 817.22 | 3264.88 | 4 |
| DGS FSDEM NTILD NLAAR DFINW LIQTK ITDR | 3712.8 | 1857.81 | 3713.91 | 2 |
| GS FSDEM NTILD NLAAR DFINW LIQTK ITDR | 3597.77 | 1799.95 | 3598.92 | 2 |
| SDEM NTILD NLAAR DFINW LIQTK ITDR* | 3263.65 | 1634.43 | 3266.8 | 2 |
| EM NTILD NLAAR DFINW LIQTK ITDR | 3104.59 | 1553.41 | 3104.82 | 2 |
| ILD NLAAR DFINW LIQTK ITDR | 2629.42 | 1315.68 | 2629.36 | 2 |
| NLAAR DFINW LIQTK ITDR | 2288.23 | 1144.92 | 2287.84 | 2 |

*These peptides had lost a $CN_2H_3$ fragment (43 g/mole) from an arginine side chain.

B. The Effect of Clostripain Concentration

The effect of clostripain concentration on the cleavage of a precursor polypeptide was determined by combining clostripain with T7tag-GSDR-[GLP-2(1-34)]$_6$ at various ratios of clostripain to the precursor polypeptide in a cleavage reaction. The tested ratios were 1, ½, ¼, ⅛ units of clostripain per mg of precursor polypeptide. The concentration of the precursor polypeptide was kept constant at 1.2 mg/ml. The cleavage reaction was conducted in buffer containing 10 mM Tris, 1 mM EDTA, and 5 mM of $CaCl_2$ (pH 8.0) at 21° C. The cleavage reactions were initiated by addition of clostripain to the cleavage reactions. Aliquots were withdrawn at selected time intervals, quenched, and analyzed by HPLC.

As shown in FIG. 8B, the slowest reaction containing a ratio of 1 unit clostripain per 8 mg of precursor polypeptide was three times slower than the fastest reaction containing a ratio of 1 unit clostripain per 1 mg of substrate. As shown in FIGS. 8A and 8B, a 180 min reaction at 40° C. containing a ratio of 1 unit clostripain per 20 mg of substrate was approximately equivalent to a 20 min reaction with 1 unit clostripain per 1 mg of substrate at room temperature. It is noteworthy that a reaction containing only 1 unit clostripain per 100 mg of substrate produced a higher ratio of full length GLP-2 (1-34) to truncated GLP-2 (21-34). It is also noteworthy that a reaction containing 1 unit clostripain per 20 mg of precursor polypeptide at the ambient room temperature was almost complete at 10 hr and produced less GLP-2(21-34) than did the same reaction at 40° C. after about 3.5 hr.

Example 9

Preparation of Amidated Cleavage Products from a Multicopy Precursor Polypeptide A reaction mixture was prepared by combining clostripain with T7tag-GS-[GPGDR-GLP-1(7-36)-AFL]$_3$ (6.66 mg/ml) in a cleavage reaction containing 2.8 M $NH_4Cl$-1.0 M $NH_4OH$ buffer with 1 mM $CaCl_2$ and 1 mM cysteine at pH 9.0 and 45° C. The cleavage reaction was initiated by the addition of clostripain (12 units per mg of precursor polypeptide) to the cleavage reaction. The reaction was quenched by diluting the cleavage reaction 10-fold in 60% acetic acid. The products of the reaction were analyzed with an HPLC that was equipped with a Vydac C4 column (FIG. 9). The following gradient was used: 30% buffer B for 7.5 minutes and 50-70% buffer B in 1 minute at a flow rate of 2.0 mL/min. The buffers yield at pH 8.6 to 8.8. It is noted that $NH_4Cl$ may be substituted as a source of ammonia in order to cause C-terminal amidation of the cleavage products. A purified preparation of GLP-1(7-36)-$NH_2$ was subjected to complete amino acid sequence analysis which confirmed the structure of this peptide.

Example 10

Production of a Peptide Produced Through Transpeptidation

Figure 10A:
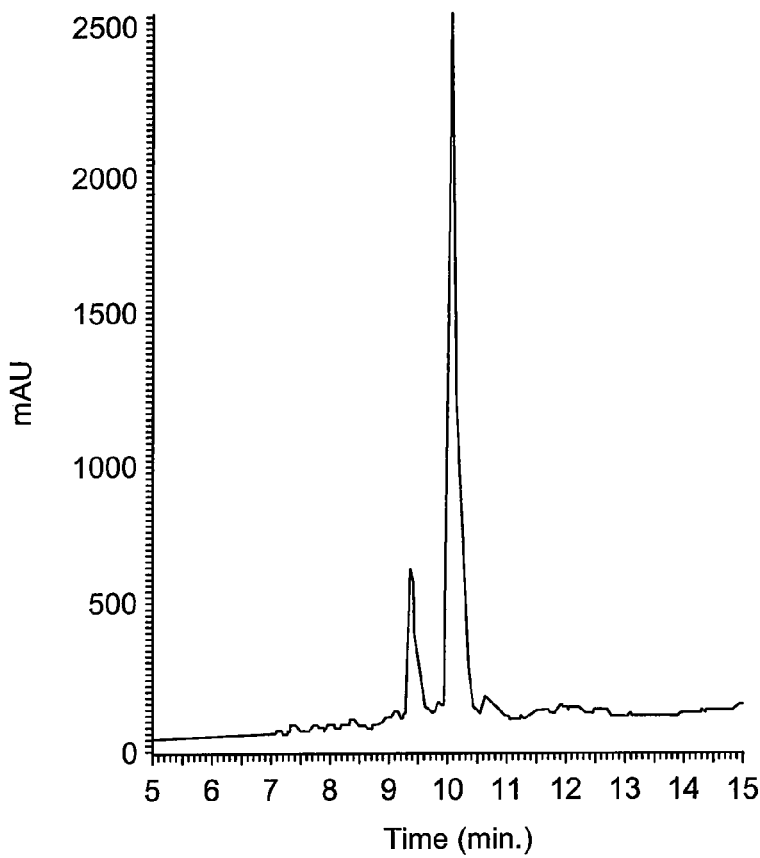
Figure 10B:
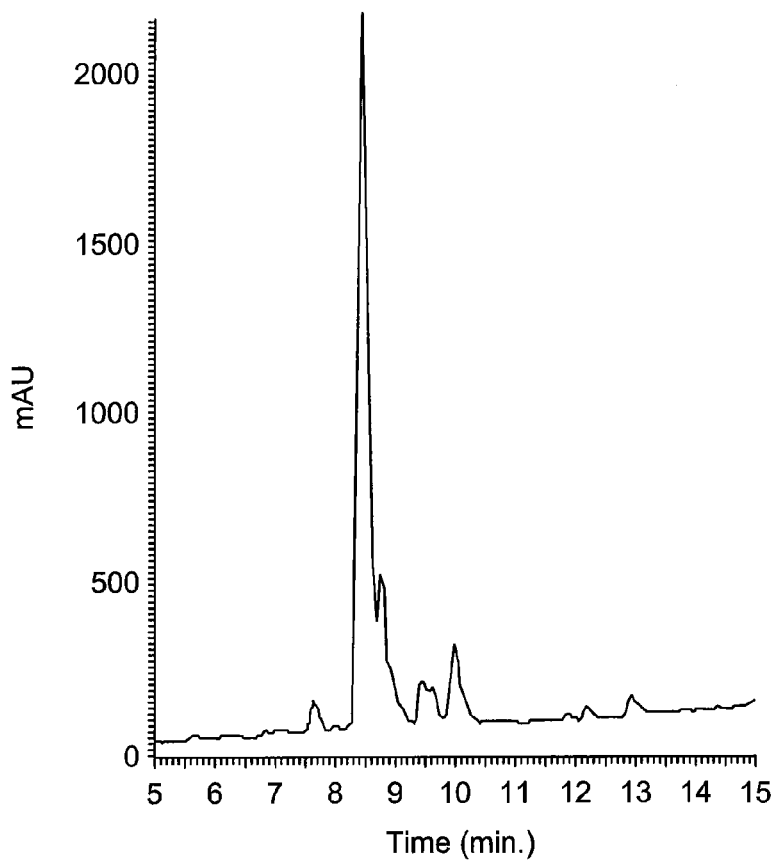
Figure 10C:
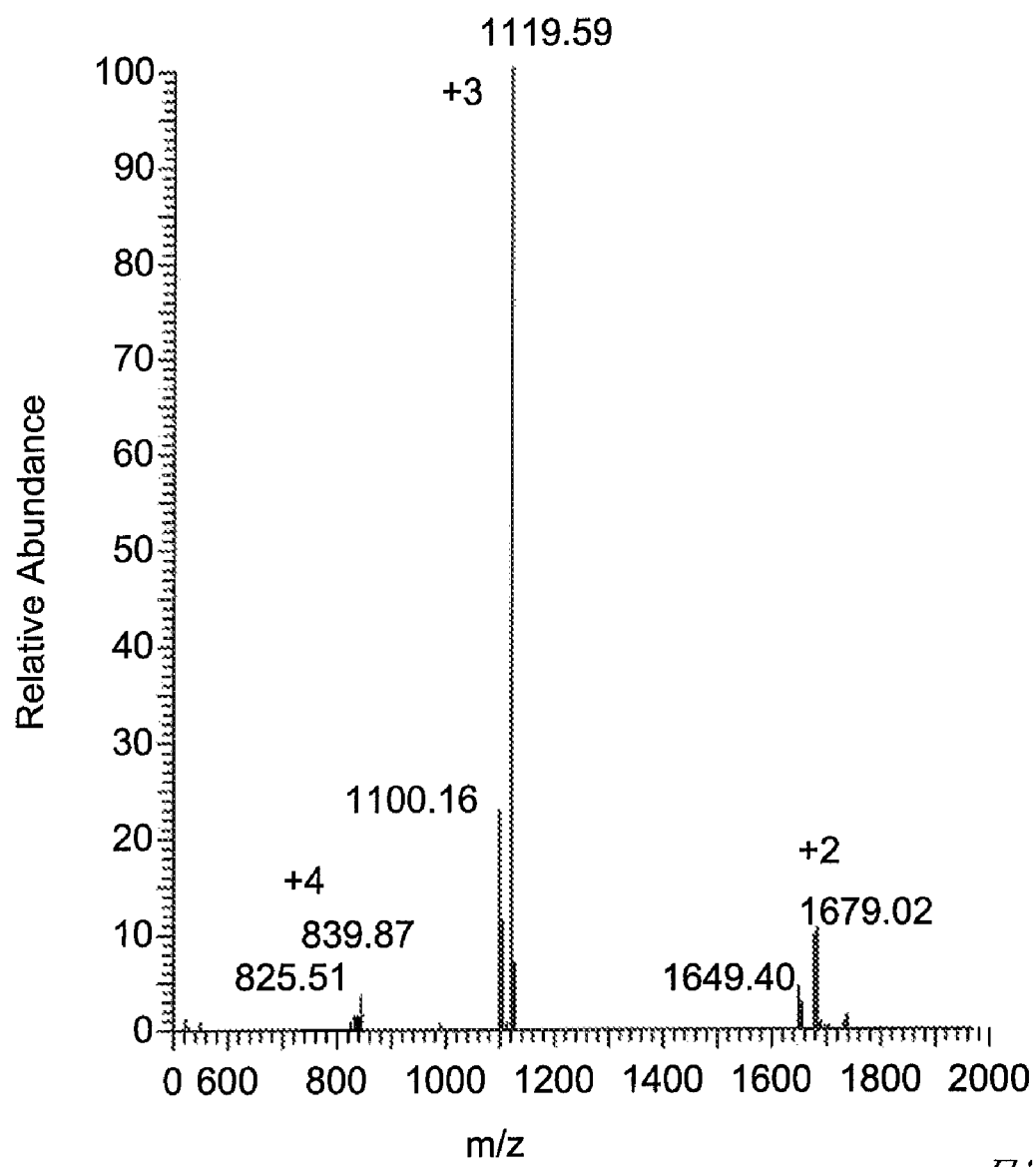

GLP-1(7-36)AFAHSe was expressed from a recombinant construct (MASMTGGQQMGSLQG$_5$[GLP-1(7-36)AFM]$_7$ GLP-1(7-36)AFAMHAE) and was then prepared by CNBr cleavage of the expression product from the expression construct. To perform the clostripain catalyzed cleavage and transpeptidation reaction, the following were combined in a 1 ml reaction mixture: 1 mg of the GLP-1(7-36)AFAHSe (free acid and lactone mixture), 0.2 mM $CaCl_2$, 1 mM cysteine, 0.5 M glycine, 1.25 M $NH_4OH$ and 1 unit of clostripain. The mixture was incubated for 30 minutes at pH 10.0 and 45° C. The reaction was terminated by diluting an aliquot of the reaction mixture 10-fold into 60% acetic acid. The sample was then subjected to analysis by LC/MS as described above. The data in FIG. 10A shows HPLC analysis of the GLP-1(7-36)AFAHSe. The constituents at about 10.09 minutes and about 9.4 minutes were GLP-1(7-36)AFAHSe and GLP-1(7-36)AFAHSe-lactone. After 30 minutes of incubation, the single major component that eluted at about 8.3 minutes (FIG. 10B) was detected with the concomitant disappearance of the two constituents of the unreacted material. The mass of the main constituent of FIG. 10B was 3356 (FIG. 10C) which was identical to the molecular weight of GLP-1(7-37). The yield was in excess of 60%.

Example 11

Preparation of Peptide Product Having a C-Terminal Arginine Group from a Precursor Polypeptide A precursor polypeptide containing Human fibrinopeptide (HFPA) (ADSGEGDFLAEGGGVR) (SEQ ID NO: 39) can be produced by expression of a recombinant T7tag-GSDR-[HFPA]x construct where x can be any integer between 1 and 32. The precursor polypeptide can be isolated according to the methods described herein. Such a precursor polypeptide can be cleaved into multiple individual peptides corresponding to HFPA though the action of clostripain. Furthermore, the peptide product may be C-terminally amidated by cleavage under conditions also described herein. For example, the cleavage reaction may be conducted at a pH of about 8.9. Alternatively, the precursor polypeptide may be cleaved at a pH of about 6 to produce a peptide product having a C-terminal carboxylate group. The precursor polypeptide may also be transpeptidated according to the method of Example 10. Those of skill in the art recognize that many peptides having a C-terminal arginine may be produced in an analogous fashion. The peptide product may also be extended though the use of primary amines, peptides and amino acids. Examples of peptides having a C-terminal arginine include, but are not limited to, amyloid P component and urechistachykinin II.

Example 12

Preparation of Peptide Product Lacking an Arginine from a Precursor Polypeptide

A peptide product that lacks an arginine residue can be produced through use of the methods of the invention. Such a peptide is exemplified by porcine valosin (PoV) (VQYPVEHPDKFLKFGMTPSKGVLFY) (SEQ ID NO: 40) which can be produced by expression of a recombinant T7tag-GSDR-[PoV]x construct where x can be an integer from 1 to 32. The precursor polypeptide can be isolated according to the methods described herein. Such a precursor polypeptide can be cleaved into multiple individual peptides corresponding to PoV though the action of clostripain. Furthermore, the peptide product may be C-terminally amidated by cleavage under conditions also described herein. For example, the cleavage reaction may be conducted at a pH of about 8.9. Alternatively, the precursor polypeptide may be cleaved at a pH of about 6 to produce a peptide product having a C-terminal carboxylate group. The precursor polypeptide may also be transpeptidated according to the method of Example 10. Those of skill in the art recognize that many peptides that lack an arginine residue may be produced in an analogous fashion. The peptide product may also be extended though the use of primary amines, peptides and amino acids. Examples of peptides that lack an arginine residue include, but are not limited to, camel Э-endorphin, alpha-endorphin, vasoactive intestinal contractile peptide from mouse, amyloid Э-protein (12-28), and magainin (GIGKFLKKAKKFGKAFVKILKK-NH$_2$) (SEQ ID NO: 41). In the case of magainin, a cysteine can be added to the C-terminus which allows the peptide to be amidated according to reported methods. [Catsimpoolas and Wood, *J. Biol. Chem.*, (1979)].

REFERENCES

Alberts et al., Molecular Biology of the Cell, 2nd ed., 1989
Amann et al., *Gene*, 25:167 (1983)
Amann et al., *Gene*, 40: 183, (1985)
Aubin et al., *Methods Mol. Biol.*, 62:319 (1997)
Augustin et al., *FEMS Microbiol. Lett.*, 66: 203 (1990)
Ausubel et al., *Current Protocols in Molecular Biology*, Green Publishing Associates and Wiley Interscience, NY (1989)
Barany et al., *J. Bacteriol.*, 144: 698 (1980)
Beach and Nurse, *Nature*, 300:706 (1981)
Beaucage and Caruthers, *Tetra. Letts.*, 22:1859 (1981)
Boshart et al., *Cell*, 41:521 (1985)
Botstein, et al., *Gene*, 8:17 (1979)
Brake et al., *Proc. Natl. Acad. Sci. USA*, 81:4642 (1984)
Butt et al., *Microbiol. Rev.*, 51:351 (1987)
Carbonell et al., *Gene*, 73: 409 (1988)
Carbonell et al., *J. Virol.*, 56:153 (1985)
Catsimpoolas and Wood, *J. Biol. Chem.*, (1979)
Chaney et al., *Somat. Cell Mol. Genet.*, 12:237 (1986)
Chang et al., *Nature*, 198:1056 (1977)
Chassy et al., *FEMS Microbiol. Lett.*, 44: 173 (1987)
Cohen et al., *Proc. Natl. Acad. Sci. USA*, 69: 2110 (1973)
Cohen et al., *Proc. Natl. Acad. Sci. USA*, 77:1078 (1980)
Cregg et al., *Mol. Cell. Biol.*, 5: 3376, (1985)
Das et al., *J. Bacteriol.*, 158: 1165 (1984)
Davidow et al., *Curr. Genet.*, 10:39 (1985)
Davies et al., *Ann. Rev. Microbiol.*, 32: 469, 1978
Dayhoff et al., Atlas of Protein Sequence and Structure, Natl. Biomed. Res. Found., Washington, C.D. (1978)
de Boer et al., *Proc. Natl. Acad. Sci. USA*, 80:21 (1983)
De Louvencourt et al., *J. Bacteriol.*, 154:737 (1983)
Dijkema et al., *EMBO J.*, 4:761 (1985)
Dower et al., *Nuc. Acids Res.*, 16: 6127 (1988)
Dykes et al., *Eur. J. Biochem.*, 174: 411 (1988)
EPO Publ. Nos. 036 259 and 063 953
EPO Publ. Nos. 036 776, 136 829 and 136 907
EPO Publ. No. 121 775
EPO Publ. No. 127 328
EPO Publ. Nos. 127 839 and 155 476
EPO Publ. No. 164 556
EPO Publ. No. 267 851
EPO Publ. No. 329 203
Felgner et al., *Proc. Natl. Acad. Sci.*, 84:7413 (1987)
Felgner et al., *J. Biol. Chem.*, 269:2550 (1994)
Fiedler et al., *Anal. Biochem*, 170: 38 (1988)
Forsberg et al., *Biofactors*, 2: 105-112, (1989)
Forsberg et al., *Int. J. Protein Chem.*, 11: 201-211, (1992)
Franke and Hruby, *J. Gen. Virol.*, 66:2761 (1985)
Fraser et al., *In Vitro Cell. Dev. Biol.*, 25:225 (1989)
Freifelder, Physical Biochemistry: Applications to Biochemistry and Molecular Biology, W.H. Freeman and Co., 2nd edition, New York, N.Y. (1982).
Friesen et al., "The Regulation of Baculovirus Gene Expression", in: The Molecular Biology of Baculoviruses (ed. Walter Doerfler), 1986
Gaillardin et al., *Curr. Genet.*, 10:49 (1985)
Ghrayeb et al., *EMBO J.*, 3: 2437 (1984)
Gleeson et al., *J. Gen. Microbiol.*, 132:3459 (1986)
Gluzman, *Cell*, 23:175 (1981)
Goeddel et al., *Nuc. Acids Res.*, 8:4057 (1980)
Gorman et al., *Proc. Natl. Acad. Sci. USA*, 79:6777 (1982b)
Graham and van der Eb, *Virology*, 52:456 (1973)
Gram et al., *Bio/Technology*, 12: 1017-1023, (1994)
Guan et al., *Gene*, 67:21 (1997)
Harlander, "Transformation of *Streptococcus lactis* by electroporation", in: *Streptococcal Genetics* (ed. J. Ferretti and R. Curtiss III), (1987)
Henikoff et al., *Nature*, 283:835 (1981); Hollenberg et al., *Curr. Topics Microbiol. Immunol.*, 96:119 (1981)
Hinnen et al., *Proc. Natl. Acad. Sci. USA*, 75:1929 (1978)
Hollenberg et al., "The Expression of Bacterial Antibiotic Resistance Genes in the Yeast *Saccharomyces cerevisiae*", in: Plasmids of Medical, Environmental and Commercial Importance (eds. K. N. Timmis and A. Puhler), 1979
Ito et al., *J. Bacteriol.*, 153:163 (1983)
Kaufman et al., *Mol. Cell. Biol.*, 9:946 (1989)
Kawai and Nishizawa, *Mol. Cell. Biol.*, 4:1172 (1984)
Knott et al., *Eur. J. Biochem.*, 174: 405-410, (1988)
Kunkel, *Proc. Natl. Acad. Sci. USA*, 82:488, (1985)
Kunkel et al., *Methods in Enzymol.*, 154:367 (1987)
Kunze et al., *J. Basic Microbiol.*, 25:141 (1985)

Kurtz et al., *Mol. Cell. Biol.*, 6:142 (1986)
Kushner, "An improved method for transformation of *Escherichia coli* with ColE1-derived plasmids", in: *Genetic Engineering: Proceedings of the International Symposium on Genetic Engineering* (eds. H. W. Boyer and S, Nicosia), (1978)
Labouesses B., *Bull. Soc. Chim. Biol.*, 42: 1293, (1960)
Lebacq-Verheyden et al., *Mol. Cell. Biol.*, 8: 3129 (1988)
Luckow and Summers, *Virology*, 17:31 (1989)
Maeda et al., *Nature*, 315:592 (1985)
Mandel et al., *J. Mol. Biol.*, 53: 159 (1970);
Maniatis et al., *Science*, 236:1237 (1987)
Marcus, *Int. J. Peptide Protein Res.*, 25: 542-546, (1985)
Martin et al., *DNA*, 7: 99 (1988)
Marumoto et al., *J. Gen. Virol.*, 68:2599 (1987)
Masson et al., *FEMS Microbiol. Lett.*, 60: 273 (1989)
Masui et al., in: Experimental Manipulation of Gene Expression, (1983)
McCarroll and King, *Curr. Opin. Biotechnol.*, 8:590 (1997)
Mercerau-Puigalon et al., *Gene*, 11:163 (1980)
Miller et al., *Ann. Rev. Microbiol.*, 42:177 (1988)
Miller et al., *Proc. Natl. Acad. Sci. USA*, 8: 856 (1988)
Miller et al., *Bioessays*, 4:91 (1989)
Mitchell W., *Meth. of Enzymol.*, 47: 165-170 (1977)
Mitchell, W. M, Harrington, W. F. *J. of Biol. Chem.*, 243 (18): 4683-4692 (1968)
Miyajima et al., *Gene*, 58: 273 (1987)
Moks et al., *Bio/Technology*, 5: 379-382, (1987)
Myanohara et al., *Proc. Natl. Acad. Sci. USA*, 80:1 (1983)
Neuman et al., *EMBO J.*, 1:841 (1982)
Oka et al., *Proc. Natl. Acad. Sci. USA*, 82: 7212 (1985)
Orr-Weaver et al., *Methods in Enzymol.*, 101:228 (1983)
Palva et al., *Proc. Natl. Acad. Sci. USA*, 79: 5582 (1982)
Panthier et al., *Curr. Genet.*, 2:109 (1980)
Perry et al., *Infec. Immun.*, 32: 1295 (1981)
PCT Publ. No. WO 84/04541
PCT Pub. No. WO 89/046699
Piers et al., *Gene*, 134: 7, (1993)
Pilon et al., *Biotechnol. Prog.*, 13, 374-379 (1997)
Powell et al., *Appl. Environ. Microbiol.*, 54: 655, (1988)
Raibaud et al., *Ann. Rev. Genet.*, 18:173 (1984)
Ray et al., *Bio/Technology*, 11: 64 (1993)
Rine et al., *Proc. Natl. Acad. Sci. USA*, 80:6750 (1983)
Roggenkamp et al., *Mol. Gen. Genet.*, 202:302 (1986)
Sambrook and Russell, Molecular Cloning: A Laboratory Manual, 3rd edition (Jan. 15, 2001) Cold Spring Harbor Laboratory Press, ISBN: 0879695765
Sanford et al., *Methods Enzymol.*, 217:483 (1993)
Sassone-Corsi and Borelli, *Trends Genet.*, 2:215 (1986)
Schellenberger et al., *Int. J. Peptide Protein Res.*, 41: 326 (1993)
Shen, *Proc. Nat'l. Acad. Sci. (USA)*, 281: 4627 (1984)
Shimatake et al., *Nature*, 292:128 (1981)
Shimizu et al., *Mol. Cell. Biol.*, 6:1074 (1986)
Shine et al., *Nature*, 254: 34, (1975)
Smith et al., *Proc. Natl. Acad. Sci. USA*, 82: 8404 (1985)
Smith et al., *Mol. Cell. Biol.*, 3:2156 (1983)
Somkuti et al., *Proc. 4th Eur. Cong. Biotechnology*, 1: 412 (1987)
Steitz et al., "Genetic signals and nucleotide sequences in messenger RNA", in: Biological Regulation and Development: Gene Expression (ed. R. F. Goldberger) (1979)
Studier et al., *J. Mol. Biol.*, 189:113 (1986)
Stinchcomb et al., *J. Mol. Biol.*, 158:157 (1982)
Summers and Smith, Texas Agricultural Experiment Station Bulletin No. 1555, 1987.
Tabor et al., *Proc. Natl. Acad. Sci. USA*, 82:1074 (1985)
Taketo, *Biochim. Biophys. Acta*, 949: 318 (1988)
U.S. Pat. No. 4,336,336
U.S. Pat. No. 4,551,433
U.S. Pat. No. 4,689,406
U.S. Pat. No. 4,738,921
U.S. Pat. No. 4,745,056
U.S. Pat. Nos. 4,837,148 and 4,929,555
U.S. Pat. No. 4,873,192
U.S. Pat. Nos. 4,876,197 and 4,880,734
U.S. Pat. No. 5,595,887 to Coolidge et al.
U.S. Pat. No. 5,707,826 to Wagner et al.
U.S. Pat. No. 6,316,224
Vaheri and Pagano, *Virology*, 27:434 (1965)
Van den Berg et al., *Bio/Technology*, 8:135 (1990)
VanDevanter et al., *Nucleic Acids Res.*, 12:6159 (1984)
Vlak et al., *J. Gen. Virol.*, 69:765 (1988)
Walker and Gaastra, eds., Techniques in Molecular Biology, MacMillan Publishing Company, New York (1983)
Wang et al., *J. Bacteriol.*, 172: 949 (1990)
Watson, Molecular Biology of the Gene, 4th edition, Benjamin/Cummings Publishing Company, Inc., Menlo Park, Calif. (1987)
Weissmann, "The cloning of interferon and other mistakes", in: Interferon 3 (ed. I. Gresser), 1981
Williams et al., *Control of Drosophila wing and haltere development by the nuclear vestigial gene product, Genes Dev.* Dec. 5, (12B):2481-95 (1991)
Wright, *Nature*, 321: 718 (1986)
Yelverton et al., *Nuc. Acids Res.*, 9:731 (1981)
Zimmerman, *Biochem. Biophys. Acta.*, 694:227 (1982)

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A method for producing a desired peptide from a polypeptide, comprising:
   combining the polypeptide and clostripain, wherein the polypeptide comprises Formula (II)

$$(Xaa_3\text{-Peptide}_1\text{-}Xaa_1\text{-}Xaa_2)_n\text{-}Xaa_3\text{-Peptide}_1\text{-}Xaa_1\text{-}Xaa_2 \quad (II);$$

the desired peptide comprises $Xaa_3$-Peptide$_1$-$Xaa_1$-$Xaa_2$;
   Peptide$_1$ is any amino acid sequence other than $Xaa_1$-$Xaa_2$;
   n is an integer ranging from 0 to 50;
   $Xaa_1$ is aspartic acid, glycine, proline or glutamic acid;
   $Xaa_2$ is arginine; and
   $Xaa_3$ is not an acidic amino acid;
   wherein the peptide bond between $Xaa_2$ and the amino acid on the C-terminal side of $Xaa_2$ is cleaved; and
   wherein the cleavage occurs selectively over cleavage at other arginine or lysine residues within the polypeptide.

2. The method of claim 1, wherein the polypeptide is a soluble polypeptide.

3. The method of claim 1, wherein the cleavage is performed at about 18° C. to about 25° C.

4. The method of claim 1, wherein the cleavage is performed between a pH of about 5 and about 11.

5. The method of claim 1, wherein the concentration of clostripain is about 0.01 to about 3.0 units of clostripain per about 2 to about 5 mg polypeptide.

6. The method of claim 1, wherein the cleavage is performed in the presence of about 0.5 mM to about 10 mM $CaCl_2$.

7. The method of claim 1, wherein the desired peptide comprises any one of SEQ ID NO:1-16.

8. The method of claim 1, wherein the polypeptide comprises four or six copies of GLP-2(1-34) sequence.

9. The method of claim 1, wherein the polypeptide comprises four or six copies of GLP-1(7-36) sequence.

* * * * *

SEQUENCE LISTING

<160> NUMBER OF SEQ ID NOS: 58

<210> SEQ ID NO 1
<211> LENGTH: 30
<212> TYPE: PRT
<213> ORGANISM: Artificial Sequence
<220> FEATURE:
<223> OTHER INFORMATION: A synthetic peptide -continued

```
<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: A synthetic  peptide
<220> FEATURE:
<221> NAME/KEY: SITE
<222> LOCATION: 30
<223> OTHER INFORMATION: Xaa = Arg-NH2

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Xaa
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: A synthetic peptide

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 31
<223> OTHER INFORMATION: Xaa = Gly-NH2

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: A synthetic peptide

<400> SEQUENCE: 5

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg
            20                  25                  30
```

```
<210> SEQ ID NO 6
<211> LENGTH: 30
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 30
<223> OTHER INFORMATION: Xaa = Arg-NH2

<400> SEQUENCE: 6

His Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Lys Gly Xaa
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: A synthetic peptide

<400> SEQUENCE: 7

His Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Lys Gly Arg Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 31
<223> OTHER INFORMATION: Xaa = Gly-NH2

<400> SEQUENCE: 8

His Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Lys Gly Arg Xaa
            20                  25                  30

<210> SEQ ID NO 9
<211> LENGTH: 34
<212> TYPE: PRT
<213> ORGANISM: Artificial Sequence
<220> FEATURE:
<223> OTHER INFORMATION: A synthetic peptide

<400> SEQUENCE: 9

His Ala Asp Gly Ser Phe Ser Asp Gly Met Asn Thr Ile Leu Asp Asn
 1               5                  10                  15

Leu Ala Ala Arg Asp Phe Ile Asn Trp Leu Ile Gln Thr Lys Ile Thr
            20                  25                  30

Asp Arg

<210> SEQ ID NO 10
<211> LENGTH: 34
<212> TYPE: PRT
```

<213> ORGANISM: Artificial Sequence
<220> FEATURE:
<223> OTHER INFORMATION: A synthetic peptide
<220> FEATURE:
<221> NAME/KEY: SITE
<222> LOCATION: 34
<223> OTHER INFORMATION: Xaa = Arg-NH2

<400> SEQUENCE: 10

His Ala Asp Gly Ser Phe Ser Asp Gly Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Xaa

<210> SEQ ID NO 11
<211> LENGTH: 33
<212> TYPE: PRT
<213> ORGANISM: Artificial Sequence
<220> FEATURE:
<223> OTHER INFORMATION: A synthetic peptide

<400> SEQUENCE: 11

His Ala Asp Gly Ser Phe Ser Asp Gly Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 12
<211> LENGTH: 33
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 33
<223> OTHER INFORMATION: Xaa = Asp-NH2

<400> SEQUENCE: 12

His Ala Asp Gly Ser Phe Ser Asp Gly Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Xaa

<210> SEQ ID NO 13
<211> LENGTH: 33
<212> TYPE: PRT
<213> ORGANISM: Artificial Sequence
<220> FEATURE:
<223> OTHER INFORMATION: A synthetic peptide

<400> SEQUENCE: 13

His Gly Asp Gly Ser Phe Ser Asp Gly Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 14
<211> LENGTH: 33

```
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 33
<223> OTHER INFORMATION: Xaa = Asp-NH2

<400> SEQUENCE: 14

His Gly Asp Gly Ser Phe Ser Asp Gly Met Asn Thr Ile Leu Asp Asn
 1               5                  10                  15

Leu Ala Ala Arg Asp Phe Ile Asn Trp Leu Ile Gln Thr Lys Ile Thr
            20                  25                  30

Xaa

<210> SEQ ID NO 15
<211> LENGTH: 34
<212> TYPE: PRT
<213> ORGANISM: Artificial Sequence
<220> FEATURE:
<223> OTHER INFORMATION: A synthetic peptide

<400> SEQUENCE: 15

His Gly Asp Gly Ser Phe Ser Asp Gly Met Asn Thr Ile Leu Asp Asn
 1               5                  10                  15

Leu Ala Ala Arg Asp Phe Ile Asn Trp Leu Ile Gln Thr Lys Ile Thr
            20                  25                  30

Asp Arg

<210> SEQ ID NO 16
<211> LENGTH: 34
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 34
<223> OTHER INFORMATION: Xaa = Arg-NH2

<400> SEQUENCE: 16

His Gly Asp Gly Ser Phe Ser Asp Gly Met Asn Thr Ile Leu Asp Asn
 1               5                  10                  15

Leu Ala Ala Arg Asp Phe Ile Asn Trp Leu Ile Gln Thr Lys Ile Thr
            20                  25                  30

Asp Xaa

<210> SEQ ID NO 17
<211> LENGTH: 11
<212> TYPE: PRT
<213> ORGANISM: Artificial Sequence
<220> FEATURE:
<223> OTHER INFORMATION: A synthetic T7 tag

<400> SEQUENCE: 17

Ala Ser Met Thr Gly Gly Gln Gln Met Gly Arg
 1               5                  10

<210> SEQ ID NO 18
<211> LENGTH: 12
<212> TYPE: PRT
<213> ORGANISM: Artificial Sequence
<220> FEATURE:
<223> OTHER INFORMATION: A synthetic T7 tag
```

```
<400> SEQUENCE: 18

Met Ala Ser Met Thr Gly Gly Gln Gln Met Gly Arg
1               5                   10

<210> SEQ ID NO 19
<211> LENGTH: 29
<212> TYPE: PRT
<213> ORGANISM: Artificial Sequence
<220> FEATURE:
<223> OTHER INFORMATION: A synthetic inclusion body leader partner

<400> SEQUENCE: 19

Gly Ser Gly Gln Gly Gln Ala Gln Tyr Leu Ser Ala Ser Cys Val Val
1               5                   10                  15

Phe Thr Asn Tyr Ser Gly Asp Thr Ala Ser Gln Val Asp
            20                  25

<210> SEQ ID NO 20
<211> LENGTH: 38
<212> TYPE: PRT
<213> ORGANISM: Artificial Sequence
<220> FEATURE:
<223> OTHER INFORMATION: A synthetic inclusion body leader partner
      (a part of the Drosophilavestigial polypeptide (Vg))

<400> SEQUENCE: 20

Gly Ser Gly Gln Gly Gln Ala Gln Tyr Leu Ala Ala Ser Leu Val Val
1               5                   10                  15

Phe Thr Asn Tyr Ser Gly Asp Thr Ala Ser Gln Val Asp Val Asn Gly
            20                  25                  30

Pro Arg Ala Met Val Asp
        35

<210> SEQ ID NO 21
<211> LENGTH: 35
<212> TYPE: PRT
<213> ORGANISM: Artificial Sequence
<220> FEATURE:
<223> OTHER INFORMATION: A synthetic inclusion body leader partner
      (a part of the polyhedrin polypeptide (Ph))

<400> SEQUENCE: 21

Gly Ser Ala Glu Glu Glu Ile Leu Leu Glu Val Ser Leu Val Phe
1               5                   10                  15

Lys Val Lys Glu Phe Ala Pro Asp Ala Pro Leu Phe Thr Gly Pro Ala
            20                  25                  30

Tyr Val Asp
        35

<210> SEQ ID NO 22
<211> LENGTH: 22
<212> TYPE: PRT
<213> ORGANISM: Artificial Sequence
<220> FEATURE:
<223> OTHER INFORMATION: A synthetic inclusion body leader partner
      (a part of the lactamase polypeptide)

<400> SEQUENCE: 22

Ser Ile Gln His Phe Arg Val Ala Leu Ile Pro Phe Phe Ala Ala Phe
1               5                   10                  15

Ser Leu Pro Val Phe Ala
            20
```

```
<210> SEQ ID NO 23
<211> LENGTH: 8
<212> TYPE: PRT
<213> ORGANISM: Artificial Sequence
<220> FEATURE:
<223> OTHER INFORMATION: A synthetic cleavable peptide linker sequence

<400> SEQUENCE: 23

Ala Phe Leu Gly Pro Gly Asp Arg
 1               5

<210> SEQ ID NO 24
<211> LENGTH: 4
<212> TYPE: PRT
<213> ORGANISM: Artificial Sequence
<220> FEATURE:
<223> OTHER INFORMATION: A synthetic cleavable peptide linker sequence

<400> SEQUENCE: 24

Val Asp Asp Arg
 1

<210> SEQ ID NO 25
<211> LENGTH: 4
<212> TYPE: PRT
<213> ORGANISM: Artificial Sequence
<220> FEATURE:
<223> OTHER INFORMATION: A synthetic cleavable peptide linker sequence

<400> SEQUENCE: 25

Gly Ser Asp Arg
 1

<210> SEQ ID NO 26
<211> LENGTH: 4
<212> TYPE: PRT
<213> ORGANISM: Artificial Sequence
<220> FEATURE:
<223> OTHER INFORMATION: A synthetic cleavable peptide linker sequence

<400> SEQUENCE: 26

Ile Thr Asp Arg
 1

<210> SEQ ID NO 27
<211> LENGTH: 4
<212> TYPE: PRT
<213> ORGANISM: Artificial Sequence
<220> FEATURE:
<223> OTHER INFORMATION: A synthetic cleavable peptide linker sequence

<400> SEQUENCE: 27

Pro Gly Asp Arg
 1

<210> SEQ ID NO 28
<211> LENGTH: 117
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Xaa = T7 tag

<400> SEQUENCE: 28
```

```
Xaa Gly Ser Gly Pro Gly Asp Arg His Ala Glu Gly Thr Phe Thr Ser
 1               5                   10                  15

Asp Val Ser Ser Tyr Leu Glu Gly Gln Ala Ala Lys Glu Phe Ile Ala
                20                  25                  30

Trp Leu Val Lys Gly Arg Ala Phe Leu Gly Pro Gly Asp Arg His Ala
            35                  40                  45

Glu Gly Thr Phe Thr Ser Asp Val Ser Ser Tyr Leu Glu Gly Gln Ala
 50                  55                  60

Ala Lys Glu Phe Ile Ala Trp Leu Val Lys Gly Arg Ala Phe Leu Gly
65                   70                  75                  80

Pro Gly Asp Arg His Ala Glu Gly Thr Phe Thr Ser Asp Val Ser Ser
                85                  90                  95

Tyr Leu Glu Gly Gln Ala Ala Lys Glu Phe Ile Ala Trp Leu Val Lys
                100                 105                 110

Gly Arg Ala Phe Leu
        115
```

<210> SEQ ID NO 29
<211> LENGTH: 220
<212> TYPE: PRT
<213> ORGANISM: Artificial Sequence
<220> FEATURE:
<223> OTHER INFORMATION: A synthetic peptide

<400> SEQUENCE: 29

```
Met Ala Ser Met Thr Gly Gly Gln Gln Met Gly Arg Gly Ser Asp Arg
 1               5                   10                  15

His Ala Asp Gly Ser Phe Ser Asp Gly Met Asn Thr Ile Leu Asp Asn
                20                  25                  30

Leu Ala Ala Arg Asp Phe Ile Asn Trp Leu Ile Gln Thr Lys Ile Thr
            35                  40                  45

Asp Arg His Ala Asp Gly Ser Phe Ser Asp Gly Met Asn Thr Ile Leu
 50                  55                  60

Asp Asn Leu Ala Ala Arg Asp Phe Ile Asn Trp Leu Ile Gln Thr Lys
65                   70                  75                  80

Ile Thr Asp Arg His Ala Asp Gly Ser Phe Ser Asp Gly Met Asn Thr
                85                  90                  95

Ile Leu Asp Asn Leu Ala Ala Arg Asp Phe Ile Asn Trp Leu Ile Gln
                100                 105                 110

Thr Lys Ile Thr Asp Arg His Ala Asp Gly Ser Phe Ser Asp Gly Met
            115                 120                 125

Asn Thr Ile Leu Asp Asn Leu Ala Ala Arg Asp Phe Ile Asn Trp Leu
        130                 135                 140

Ile Gln Thr Lys Ile Thr Asp Arg His Ala Asp Gly Ser Phe Ser Asp
145                 150                 155                 160

Gly Met Asn Thr Ile Leu Asp Asn Leu Ala Ala Arg Asp Phe Ile Asn
                165                 170                 175

Trp Leu Ile Gln Thr Lys Ile Thr Asp Arg His Ala Asp Gly Ser Phe
                180                 185                 190

Ser Asp Gly Met Asn Thr Ile Leu Asp Asn Leu Ala Ala Arg Asp Phe
            195                 200                 205

Ile Asn Trp Leu Ile Gln Thr Lys Ile Thr Asp Arg
        210                 215                 220
```

<210> SEQ ID NO 30
<211> LENGTH: 38

```
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Xaa = T7tag-Vg (Vg = vestigial)

<400> SEQUENCE: 30

Xaa Val Asp Asp Arg His Gly Asp Gly Ser Phe Ser Asp Gly Met Asn
 1               5                  10                  15

Thr Ile Leu Asp Asn Leu Ala Ala Arg Asp Phe Ile Asn Trp Leu Ile
            20                  25                  30

Gln Thr Lys Ile Thr Asp
        35

<210> SEQ ID NO 31
<211> LENGTH: 123
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 15
<223> OTHER INFORMATION: Xaa = Peptide5

<400> SEQUENCE: 31

Met Ala Ser Met Thr Gly Gly Gln Gln Met Gly Arg Gly Ser Xaa Asp
 1               5                  10                  15

Arg His Ala Glu Gly Thr Phe Thr Ser Asp Val Ser Ser Tyr Leu Glu
            20                  25                  30

Gly Gln Ala Ala Lys Glu Phe Ile Ala Trp Leu Val Lys Gly Arg Ala
        35                  40                  45

Phe Leu Gly Pro Gly Asp Arg His Ala Glu Gly Thr Phe Thr Ser Asp
    50                  55                  60

Val Ser Ser Tyr Leu Glu Gly Gln Ala Ala Lys Glu Phe Ile Ala Trp
65                  70                  75                  80

Leu Val Lys Gly Arg Ala Phe Leu Gly Pro Gly Asp Arg His Ala Glu
                85                  90                  95

Gly Thr Phe Thr Ser Asp Val Ser Ser Tyr Leu Glu Gly Gln Ala Ala
            100                 105                 110

Lys Glu Phe Ile Ala Trp Leu Val Lys Gly Arg
        115                 120

<210> SEQ ID NO 32
<211> LENGTH: 37
<212> TYPE: PRT
<213> ORGANISM: Artificial Sequence
<220> FEATURE:
<223> OTHER INFORMATION: A synthetic peptide

<400> SEQUENCE: 32

His Gly Asp Gly Ser Phe Ser Asp Gly Met Asn Thr Ile Leu Asp Asn
 1               5                  10                  15

Leu Ala Ala Arg Asp Phe Ile Asn Trp Leu Ile Gln Thr Lys Ile Thr
            20                  25                  30

Asp Pro Gly Asp Arg
        35

<210> SEQ ID NO 33
```

```
<211> LENGTH: 75
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Xaa = T7 tag

<400> SEQUENCE: 33

Xaa Gly Ser Asp Arg His Gly Asp Gly Ser Phe Ser Asp Gly Met Asn
 1               5                  10                  15

Thr Ile Leu Asp Asn Leu Ala Ala Arg Asp Phe Ile Asn Trp Leu Ile
            20                  25                  30

Gln Thr Lys Ile Thr Asp Pro Gly Asp Arg His Gly Asp Gly Ser Phe
        35                  40                  45

Ser Asp Gly Met Asn Thr Ile Leu Asp Asn Leu Ala Ala Arg Asp Phe
    50                  55                  60

Ile Asn Trp Leu Ile Gln Thr Lys Ile Thr Asp
65                  70                  75

<210> SEQ ID NO 34
<211> LENGTH: 209
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Xaa = T7 tag

<400> SEQUENCE: 34

Xaa Gly Ser Asp Arg His Ala Asp Gly Ser Phe Ser Asp Gly Met Asn
 1               5                  10                  15

Thr Ile Leu Asp Asn Leu Ala Ala Arg Asp Phe Ile Asn Trp Leu Ile
            20                  25                  30

Gln Thr Lys Ile Thr Asp Arg His Ala Asp Gly Ser Phe Ser Asp Gly
        35                  40                  45

Met Asn Thr Ile Leu Asp Asn Leu Ala Ala Arg Asp Phe Ile Asn Trp
    50                  55                  60

Leu Ile Gln Thr Lys Ile Thr Asp Arg His Ala Asp Gly Ser Phe Ser
65                  70                  75                  80

Asp Gly Met Asn Thr Ile Leu Asp Asn Leu Ala Ala Arg Asp Phe Ile
                85                  90                  95

Asn Trp Leu Ile Gln Thr Lys Ile Thr Asp Arg His Ala Asp Gly Ser
            100                 105                 110

Phe Ser Asp Gly Met Asn Thr Ile Leu Asp Asn Leu Ala Ala Arg Asp
        115                 120                 125

Phe Ile Asn Trp Leu Ile Gln Thr Lys Ile Thr Asp Arg His Ala Asp
    130                 135                 140

Gly Ser Phe Ser Asp Gly Met Asn Thr Ile Leu Asp Asn Leu Ala Ala
145                 150                 155                 160

Arg Asp Phe Ile Asn Trp Leu Ile Gln Thr Lys Ile Thr Asp Arg His
                165                 170                 175

Ala Asp Gly Ser Phe Ser Asp Gly Met Asn Thr Ile Leu Asp Asn Leu
            180                 185                 190

Ala Ala Arg Asp Phe Ile Asn Trp Leu Ile Gln Thr Lys Ile Thr Asp
        195                 200                 205
```

Arg

<210> SEQ ID NO 35
<211> LENGTH: 39
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Xaa = T7tag-Vg (Vg = vestigial)

<400> SEQUENCE: 35

Xaa Val Asp Asp Arg His Ala Asp Gly Ser Phe Ser Asp Gly Met Asn
 1               5                  10                  15

Thr Ile Leu Asp Asn Leu Ala Ala Arg Asp Phe Ile Asn Trp Leu Ile
             20                  25                  30

Gln Thr Lys Ile Thr Asp Arg
         35

<210> SEQ ID NO 36
<211> LENGTH: 34
<212> TYPE: PRT
<213> ORGANISM: Artificial Sequence
<220> FEATURE:
<223> OTHER INFORMATION: A synthetic peptide

<400> SEQUENCE: 36

His Ala Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
             20                  25                  30

Asp Arg

<210> SEQ ID NO 37
<211> LENGTH: 33
<212> TYPE: PRT
<213> ORGANISM: Artificial Sequence
<220> FEATURE:
<223> OTHER INFORMATION: A synthetic peptide

<400> SEQUENCE: 37

Ala Asp Gly Ser Phe Ser Asp Glu Met Asn Thr Ile Leu Asp Asn Leu
 1               5                  10                  15

Ala Ala Arg Asp Phe Ile Asn Trp Leu Ile Gln Thr Lys Ile Thr Asp
             20                  25                  30

Arg

<210> SEQ ID NO 38
<211> LENGTH: 32
<212> TYPE: PRT
<213> ORGANISM: Artificial Sequence
<220> FEATURE:
<223> OTHER INFORMATION: A synthetic peptide

<400> SEQUENCE: 38

Asp Gly Ser Phe Ser Asp Glu Met Asn Thr Ile Leu Asp Asn Leu Ala
 1               5                  10                  15

Ala Arg Asp Phe Ile Asn Trp Leu Ile Gln Thr Lys Ile Thr Asp Arg
             20                  25                  30

<210> SEQ ID NO 39
<211> LENGTH: 16
<212> TYPE: PRT
<213> ORGANISM: Artificial Sequence
<220> FEATURE:
<223> OTHER INFORMATION: A synthetic precursor peptide containing human
      fibrinopeptide (HFPA)

<400> SEQUENCE: 39

Ala Asp Ser Gly Glu Gly Asp Phe Leu Ala Glu Gly Gly Gly Val Arg
 1               5                  10                  15

<210> SEQ ID NO 40
<211> LENGTH: 25
<212> TYPE: PRT
<213> ORGANISM: Artificial Sequence
<220> FEATURE:
<223> OTHER INFORMATION: A synthetic peptide

<400> SEQUENCE: 40

Val Gln Tyr Pro Val Glu His Pro Asp Lys Phe Leu Lys Phe Gly Met
 1               5                  10                  15

Thr Pro Ser Lys Gly Val Leu Phe Tyr
            20                  25

<210> SEQ ID NO 41
<211> LENGTH: 22
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 22
<223> OTHER INFORMATION: Xaa = Lys-NH2

<400> SEQUENCE: 41

Gly Ile Gly Lys Phe Leu Lys Lys Ala Lys Lys Phe Gly Lys Ala Phe
 1               5                  10                  15

Val Lys Ile Leu Lys Xaa
            20

<210> SEQ ID NO 42
<211> LENGTH: 43
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 6
<223> OTHER INFORMATION: Xaa = GLP-1(1-33) A2G
<220> FEATURE:
<221> NAME/KEY: SITE
<222> LOCATION: 1
<223> OTHER INFORMATION: Xaa = T7 tag

<400> SEQUENCE: 42

Xaa Gly Ser Asp Arg Xaa Pro Gly Asp Arg His Gly Asp Gly Ser Phe
 1               5                  10                  15

Ser Asp Gly Met Asn Thr Ile Leu Asp Asn Leu Ala Ala Arg Asp Phe
            20                  25                  30

Ile Asn Trp Leu Ile Gln Thr Lys Ile Thr Asp
            35                  40

<210> SEQ ID NO 43
<211> LENGTH: 31

```
<212> TYPE: PRT
<213> ORGANISM: Artificial Sequence
<220> FEATURE:
<223> OTHER INFORMATION: A synthetic peptide

<400> SEQUENCE: 43

Gly Ser Phe Ser Asp Glu Met Asn Thr Ile Leu Asp Asn Leu Ala Ala
 1               5                  10                  15

Arg Asp Phe Ile Asn Trp Leu Ile Gln Thr Lys Ile Thr Asp Arg
            20                  25                  30

<210> SEQ ID NO 44
<211> LENGTH: 29
<212> TYPE: PRT
<213> ORGANISM: Artificial Sequence
<220> FEATURE:
<223> OTHER INFORMATION: A synthetic peptide

<400> SEQUENCE: 44

Phe Ser Asp Glu Met Asn Thr Ile Leu Asp Asn Leu Ala Ala Arg Asp
 1               5                  10                  15

Phe Ile Asn Trp Leu Ile Gln Thr Lys Ile Thr Asp Arg
            20                  25

<210> SEQ ID NO 45
<211> LENGTH: 28
<212> TYPE: PRT
<213> ORGANISM: Artificial Sequence
<220> FEATURE:
<223> OTHER INFORMATION: A synthetic peptide

<400> SEQUENCE: 45

Ser Asp Glu Met Asn Thr Ile Leu Asp Asn Leu Ala Ala Arg Asp Phe
 1               5                  10                  15

Ile Asn Trp Leu Ile Gln Thr Lys Ile Thr Asp Arg
            20                  25

<210> SEQ ID NO 46
<211> LENGTH: 32
<212> TYPE: PRT
<213> ORGANISM: Artificial Sequence
<220> FEATURE:
<223> OTHER INFORMATION: A synthetic peptide

<400> SEQUENCE: 46

Asp Gly Ser Phe Ser Asp Glu Met Asn Thr Ile Leu Asp Asn Leu Ala
 1               5                  10                  15

Ala Arg Asp Phe Ile Asn Trp Leu Ile Gln Thr Lys Ile Thr Asp Arg
            20                  25                  30

<210> SEQ ID NO 47
<211> LENGTH: 31
<212> TYPE: PRT
<213> ORGANISM: Artificial Sequence
<220> FEATURE:
<223> OTHER INFORMATION: A synthetic peptide

<400> SEQUENCE: 47

Gly Ser Phe Ser Asp Glu Met Asn Thr Ile Leu Asp Asn Leu Ala Ala
 1               5                  10                  15

Arg Asp Phe Ile Asn Trp Leu Ile Gln Thr Lys Ile Thr Asp Arg
            20                  25                  30

<210> SEQ ID NO 48
```

```
<211> LENGTH: 28
<212> TYPE: PRT
<213> ORGANISM: Artificial Sequence
<220> FEATURE:
<223> OTHER INFORMATION: A synthetic peptide

<400> SEQUENCE: 48

Ser Asp Glu Met Asn Thr Ile Leu Asp Asn Leu Ala Ala Arg Asp Phe
 1               5                  10                  15

Ile Asn Trp Leu Ile Gln Thr Lys Ile Thr Asp Arg
            20                  25

<210> SEQ ID NO 49
<211> LENGTH: 26
<212> TYPE: PRT
<213> ORGANISM: Artificial Sequence
<220> FEATURE:
<223> OTHER INFORMATION: A synthetic peptide

<400> SEQUENCE: 49

Glu Met Asn Thr Ile Leu Asp Asn Leu Ala Ala Arg Asp Phe Ile Asn
 1               5                  10                  15

Trp Leu Ile Gln Thr Lys Ile Thr Asp Arg
            20                  25

<210> SEQ ID NO 50
<211> LENGTH: 22
<212> TYPE: PRT
<213> ORGANISM: Artificial Sequence
<220> FEATURE:
<223> OTHER INFORMATION: A synthetic peptide

<400> SEQUENCE: 50

Ile Leu Asp Asn Leu Ala Ala Arg Asp Phe Ile Asn Trp Leu Ile Gln
 1               5                  10                  15

Thr Lys Ile Thr Asp Arg
            20

<210> SEQ ID NO 51
<211> LENGTH: 19
<212> TYPE: PRT
<213> ORGANISM: Artificial Sequence
<220> FEATURE:
<223> OTHER INFORMATION: A synthetic peptide

<400> SEQUENCE: 51

Asn Leu Ala Ala Arg Asp Phe Ile Asn Trp Leu Ile Gln Thr Lys Ile
 1               5                  10                  15

Thr Asp Arg

<210> SEQ ID NO 52
<211> LENGTH: 118
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Xaa = T7 tag

<400> SEQUENCE: 52

Xaa Gly Ser Gly Pro Gly Asp Arg His Ala Glu Gly Thr Phe Thr Ser
 1               5                  10                  15

Asp Val Ser Ser Tyr Leu Glu Gly Gln Ala Ala Lys Glu Phe Ile Ala
```

-continued

```
                    20                  25                  30
Trp Leu Val Lys Gly Arg Ala Phe Leu Gly Pro Gly Asp Arg Gly His
        35                  40                  45

Ala Glu Gly Thr Phe Thr Ser Asp Val Ser Ser Tyr Leu Glu Gly Gln
50                  55                  60

Ala Ala Lys Glu Phe Ile Ala Trp Leu Val Lys Gly Arg Ala Phe Leu
65                  70                  75                  80

Gly Pro Gly Asp Arg His Ala Glu Gly Thr Phe Thr Ser Asp Val Ser
                85                  90                  95

Ser Tyr Leu Glu Gly Gln Ala Ala Lys Glu Phe Ile Ala Trp Leu Val
            100                 105                 110

Lys Gly Arg Ala Phe Leu
        115

<210> SEQ ID NO 53
<211> LENGTH: 35
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 35
<223> OTHER INFORMATION: Xaa = Se

<400> SEQUENCE: 53

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Ala Phe
            20                  25                  30

Ala His Xaa
        35

<210> SEQ ID NO 54
<211> LENGTH: 35
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 35
<223> OTHER INFORMATION: Xaa = Se-lactone

<400> SEQUENCE: 54

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Ala Phe
            20                  25                  30

Ala His Xaa
        35

<210> SEQ ID NO 55
<211> LENGTH: 287
<212> TYPE: PRT
<213> ORGANISM: Artificial Sequence
<220> FEATURE:
<223> OTHER INFORMATION: A synthetic peptide

<400> SEQUENCE: 55

Met Ala Ser Met Thr Gly Gly Gln Gln Met Gly Ser Leu Gln Gly Gly
1               5                   10                  15
```

-continued

Gly Gly Gly His Ala Glu Gly Thr Phe Thr Ser Asp Val Ser Ser Tyr
            20                  25                  30

Leu Glu Gly Gln Ala Ala Lys Glu Phe Ile Ala Trp Leu Val Lys Gly
            35                  40                  45

Arg Ala Phe Met His Ala Glu Gly Thr Phe Thr Ser Asp Val Ser Ser
 50                  55                  60

Tyr Leu Glu Gly Gln Ala Ala Lys Glu Phe Ile Ala Trp Leu Val Lys
 65                  70                  75                  80

Gly Arg Ala Phe Met His Ala Glu Gly Thr Phe Thr Ser Asp Val Ser
                 85                  90                  95

Ser Tyr Leu Glu Gly Gln Ala Ala Lys Glu Phe Ile Ala Trp Leu Val
                100                 105                 110

Lys Gly Arg Ala Phe Met His Ala Glu Gly Thr Phe Thr Ser Asp Val
            115                 120                 125

Ser Ser Tyr Leu Glu Gly Gln Ala Ala Lys Glu Phe Ile Ala Trp Leu
130                 135                 140

Val Lys Gly Arg Ala Phe Met His Ala Glu Gly Thr Phe Thr Ser Asp
145                 150                 155                 160

Val Ser Ser Tyr Leu Glu Gly Gln Ala Ala Lys Glu Phe Ile Ala Trp
                165                 170                 175

Leu Val Lys Gly Arg Ala Phe Met His Ala Glu Gly Thr Phe Thr Ser
            180                 185                 190

Asp Val Ser Ser Tyr Leu Glu Gly Gln Ala Ala Lys Glu Phe Ile Ala
            195                 200                 205

Trp Leu Val Lys Gly Arg Ala Phe Met His Ala Glu Gly Thr Phe Thr
 210                 215                 220

Ser Asp Val Ser Ser Tyr Leu Glu Gly Gln Ala Ala Lys Glu Phe Ile
225                 230                 235                 240

Ala Trp Leu Val Lys Gly Arg Ala Phe Met His Ala Glu Gly Thr Phe
                245                 250                 255

Thr Ser Asp Val Ser Ser Tyr Leu Glu Gly Gln Ala Ala Lys Glu Phe
            260                 265                 270

Ile Ala Trp Leu Val Lys Gly Arg Ala Phe Ala Met His Ala Glu
            275                 280                 285

<210> SEQ ID NO 56
<211> LENGTH: 6
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Xaa = T7 tag
<220> FEATURE:
<221> NAME/KEY: SITE
<222> LOCATION: 6
<223> OTHER INFORMATION: Xaa = [HFPA], where HFPA = human fibrinopeptide
      and x is any integer between 1 and 32

<400> SEQUENCE: 56

Xaa Gly Ser Asp Arg Xaa
 1               5

<210> SEQ ID NO 57
<211> LENGTH: 6
<212> TYPE: PRT
<213> ORGANISM: Artificial Sequence
<220> FEATURE:

```
<223> OTHER INFORMATION: A synthetic peptide
<220> FEATURE:
<221> NAME/KEY: SITE
<222> LOCATION: 1
<223> OTHER INFORMATION: Xaa = T7 tag
<220> FEATURE:
<221> NAME/KEY: SITE
<222> LOCATION: 6
<223> OTHER INFORMATION: Xaa = [PoV]x, where PoV = porcine valosin and x
      is an integer from 1 to 32

<400> SEQUENCE: 57

Xaa Gly Ser Asp Arg Xaa
 1               5

<210> SEQ ID NO 58
<211> LENGTH: 4
<212> TYPE: PRT
<213> ORGANISM: Artificial Sequence
<220> FEATURE:
<223> OTHER INFORMATION: A synthetic peptide

<400> SEQUENCE: 58

Gly Ser Asp Arg
 1
```